US012680136B2

(12) United States Patent
Elnitski et al.

(10) Patent No.: US 12,680,136 B2
(45) Date of Patent: Jul. 14, 2026

(54) CANCER DETECTION METHODS

(71) Applicant: The United States of America, as represented by the Secretary, Department of Health and Human Services (the Government), Bethesda, MD (US)

(72) Inventors: Laura L. Elnitski, Gaithersburg, MD (US); Gennady Margolin, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1418 days.

(21) Appl. No.: 17/179,298

(22) Filed: Feb. 18, 2021

(65) Prior Publication Data

US 2021/0180139 A1 Jun. 17, 2021

Related U.S. Application Data

(62) Division of application No. 15/759,452, filed as application No. PCT/US2016/051905 on Sep. 15, 2016, now Pat. No. 10,961,590.

(60) Provisional application No. 62/220,041, filed on Sep. 17, 2015.

(51) Int. Cl.
    *C12Q 1/6886* (2018.01)

(52) U.S. Cl.
    CPC ..... *C12Q 1/6886* (2013.01); *C12Q 2600/154* (2013.01)

(58) Field of Classification Search
    None
    See application file for complete search history.

(56) References Cited

U.S. PATENT DOCUMENTS

2013/0041047 A1 2/2013 Orntoft et al.
2015/0118681 A1 4/2015 Kanai et al.

FOREIGN PATENT DOCUMENTS

WO WO 2009/153667 12/2009
WO WO 2013/168644 11/2013

OTHER PUBLICATIONS

Schwarzenbach et al. (Nature Reviews Cancer (2011) vol. 11:426-437).*
Arai et al., "Single-CpG-resolution methylome analysis identifies clinicopathologically aggressive CpG island methylator phenotype clear cell renal cell carcinomas," *Carcinogenesis* 33.8: 1487-1493, 2012.

Beygo et al., "Deep bisulfite sequencing of aberrantly methylated loci in a patient with multiple methylation defects," *PLoS One* 8.10: e76953, Oct. 2013 (13 pages).
Chan et al., "Noninvasive detection of cancer-associated genome-wide hypomethylation and copy number aberrations by plasma DNA bisulfite sequencing," *Proceedings of the National Academy of Sciences* 110.47: 18761-18768, 2013.
Delpu et al., "DNA Methylation and Cancer Diagnosis," *Int J Mol Sci.*, 14.7: 15029-15058, Jul. 2013.
Esposito et al., "Monitoring Tumor-Derived Cell-Free DNA in Patients with Solid Tumors: Clinical Perspectives and Research Opportunities," *Cancer Treat Rev.*, 40.5: 648-655, Jun. 2014.
Feil et al., "Methylation analysis on individual chromosomes: improved protocol for bisulphite genomic sequencing," *Nucleic Acids Research* 22.4: 695, 1994.
Frommer et al., "A genomic sequencing protocol that yields a positive display of 5-methylcytosine residues in individual DNA strands," *Proceedings of the National Academy of Sciences* 89.5: 1827-1831, 1992.
International Search Report and Written Opinion from Parent International Application No. PCT/US2016/051905, European Searching Authority, mailed Dec. 6, 2016 (11 pages).
Kolbe et al., "Differential analysis of ovarian and endometrial cancers identifies a methylator phenotype," *PLoS One* 7.3: e32941, 2012 (10 pages).
Lemire et al., "Long-range epigenetic regulation is conferred by genetic variation located at thousands of independent loci," *Nature Communications* 6: 6326, 2015, 12 pages.
Margolin et al., "Robust detection of DNA hypermethylation of ZNF154 as a pan-cancer locus with in silico modeling for blood-based diagnostic development," *The Journal of Molecular Diagnostics* 18.2: 283-298, 2016.
Masser et al., "Targeted DNA methylation analysis by next-generation sequencing," *Journal of Visualized Experiments* 96: 52488, Feb. 2015 (11 pages).
Masser et al., "Focused, high accuracy 5-methylcytosine quantitation with base resolution by benchtop next-generation sequencing," *Epigenetics & Chromatin* 6.1: 33, 2013, 12 pages.

(Continued)

*Primary Examiner* — Lori A. Clow
(74) *Attorney, Agent, or Firm* — Klarquist Sparkman, LLP

(57) ABSTRACT

The present application provides methods for the detection and diagnosis of cancer. In one aspect, the application provides methods for detecting the presence of cancer in an individual by detecting the methylation state of a region in the promoter of the ZNF154 gene. Methods are provided for detection and diagnosis of cancer from circulating tumor DNA which are minimally invasive and have diagnostic utility across different types and sub-types of cancer. In a further aspect, bioinformatics methods are provided to analyze the methylation state of the ZNF154 promoter and relate the methylation state to the likelihood of cancer in the individual.

6 Claims, 34 Drawing Sheets

Specification includes a Sequence Listing.

(56) References Cited

OTHER PUBLICATIONS

Okamoto et al., "Abstract LB-87: Methylated-Mediated Repression of ZNF154 in Ovarian Cancer is Associated with Poor Overall Survival," *AACR Cancer Res*. 72.8 Suppl: Abstract nr LB-87, Apr. 2012 (4 pages).

Reinert et al., "Comprehensive genome methylation analysis in bladder cancer; identification and validation of novel methylated genes and application of these as urinary tumor markers," *Clinical Cancer Research*: clincanres-2659, 2011, 12 pages.

Reinert et al., "Diagnosis of bladder cancer recurrence based on urinary levels of EOMES, HOXA9, POU4F2, TWIST1, VIM, and ZNF154 hypermethylation," *PloS One* 7.10: e46297, 2012 (9 pages).

Sánchez-Vega, et al. "Pan-cancer stratification of solid human epithelial tumors and cancer cell lines reveals commonalities and tissue-specific features of the CpG island methylator phenotype." *Epigenetics & Chromatin* 8, No. 1 (2015): 14, 24 pages.

Sánchez-Vega, et al. "Recurrent patterns of DNA methylation in the ZNF154, CASP8, and VHL promoters across a wide spectrum of human solid epithelial tumors and cancer cell lines." *Epigenetics* 8, No. 12 (2013): 1355-1372.

\* cited by examiner

FIG. 3B
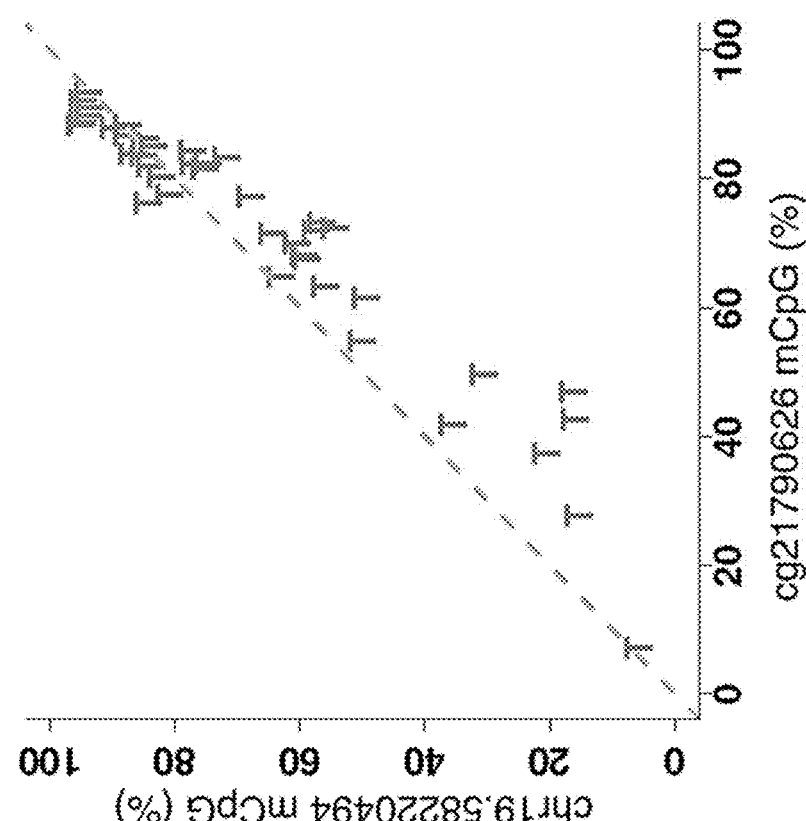
FIG. 3A
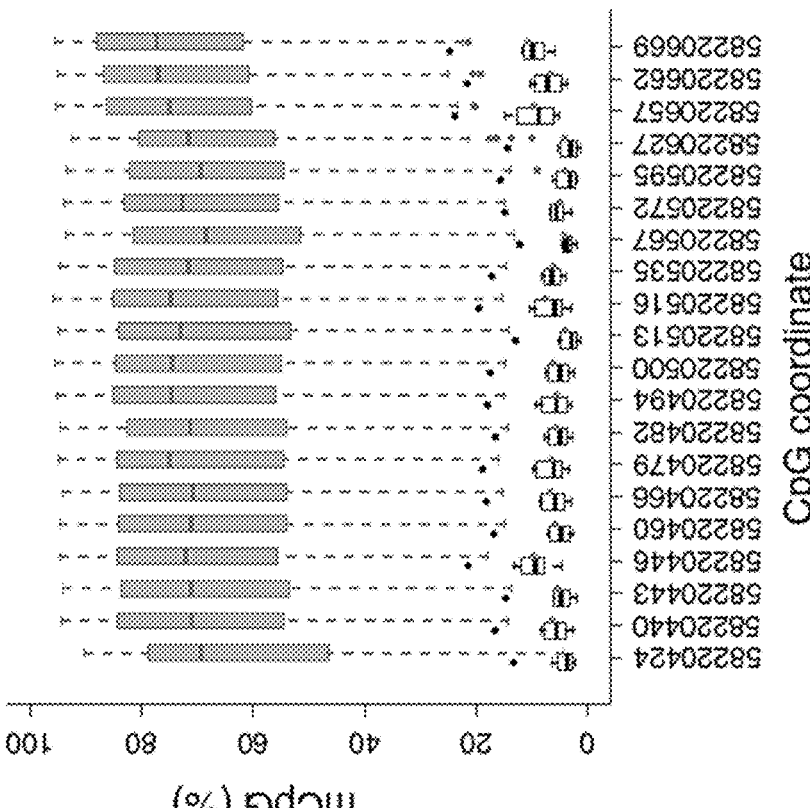

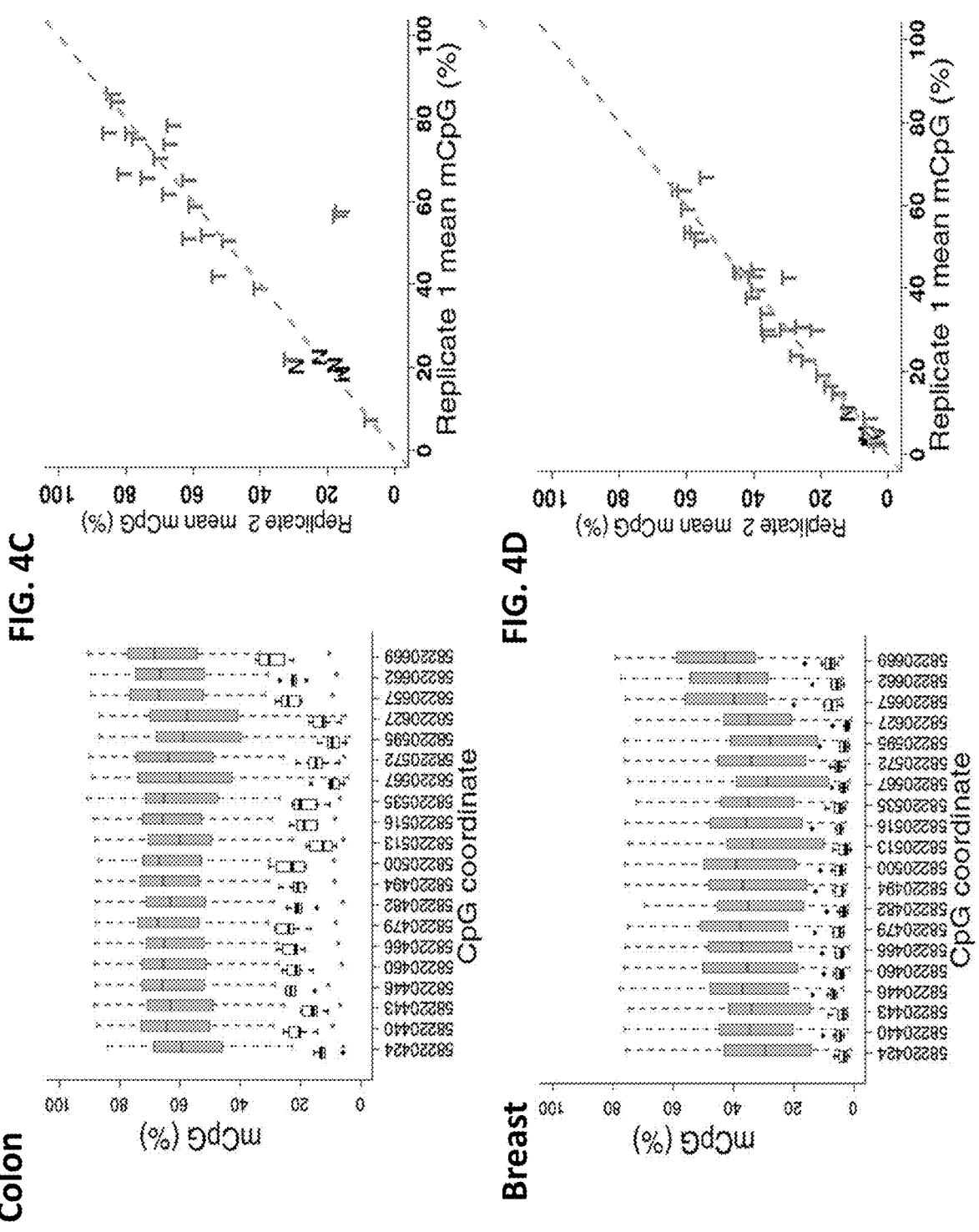

AUC = 0.936 , *P* = 7.25x10⁻¹⁶
95% CI: 0.905–0.967
Maximum(TPR–FPR) cutoff =
0.24 TPR = 0.83 , FPR = 0

AUC = 0.959 , *P* = 1.97x10⁻¹⁷
95% CI: 0.934–0.984
Maximum(TPR–FPR) cutoff = 0.05ᶜ
TPR = 0.81 , FPR = 0

FIG. 7C                    FIG. 7D
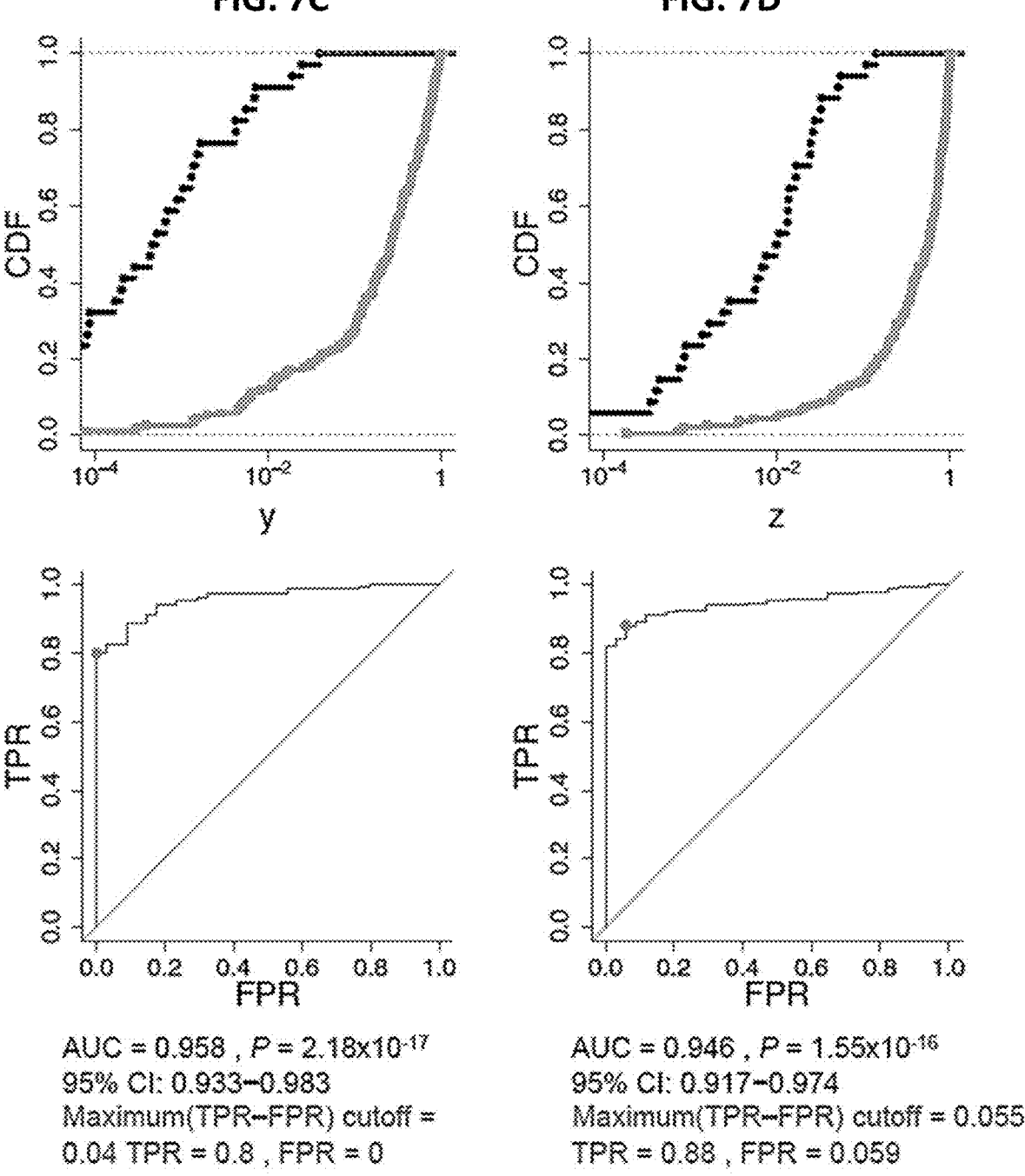
AUC = 0.958 , $P$ = 2.18x10$^{-17}$
95% CI: 0.933–0.983
Maximum(TPR–FPR) cutoff =
0.04 TPR = 0.8 , FPR = 0
AUC = 0.946 , $P$ = 1.55x10$^{-16}$
95% CI: 0.917–0.974
Maximum(TPR–FPR) cutoff = 0.055
TPR = 0.88 , FPR = 0.059

FIG. 9A                    FIG. 9B
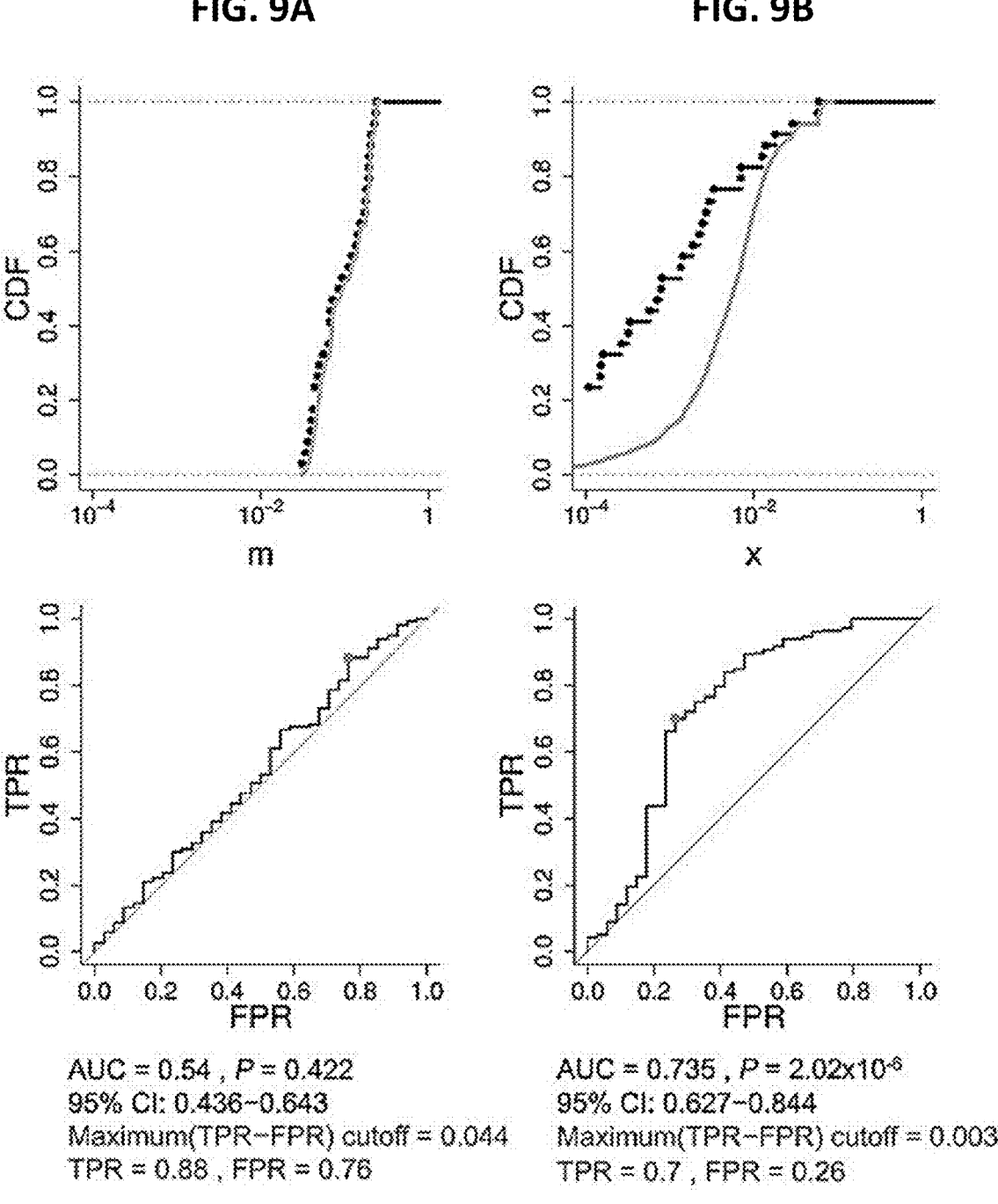
AUC = 0.54 , *P* = 0.422
95% CI: 0.436~0.643
Maximum(TPR~FPR) cutoff = 0.044
TPR = 0.88 , FPR = 0.76
AUC = 0.735 , *P* = 2.02x10$^{-6}$
95% CI: 0.627~0.844
Maximum(TPR~FPR) cutoff = 0.003
TPR = 0.7 , FPR = 0.26

FIG. 9C                    FIG. 9D
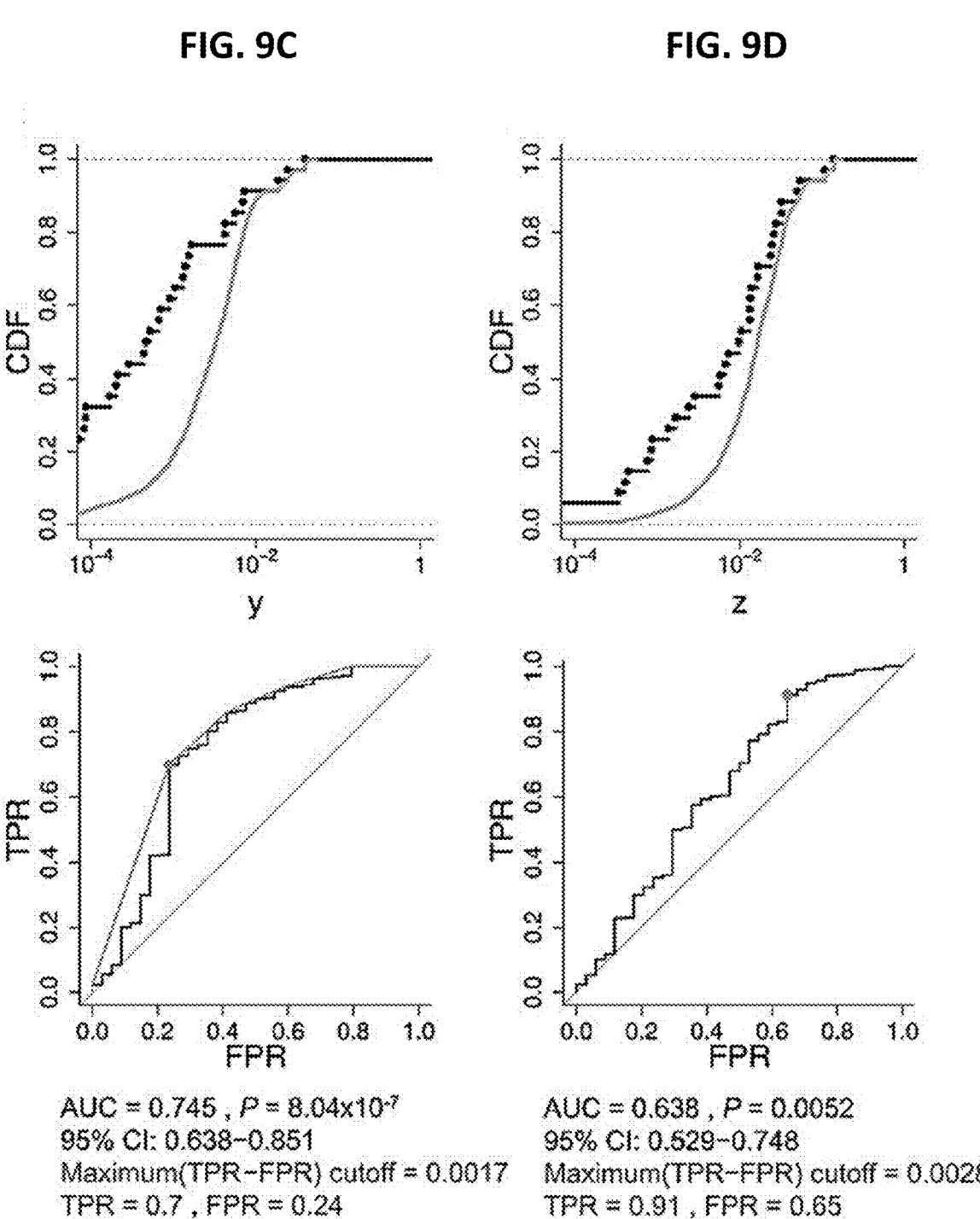
AUC = 0.745 , P = 8.04x10⁻⁷          AUC = 0.638 , P = 0.0052
95% CI: 0.638–0.851                  95% CI: 0.529–0.748
Maximum(TPR–FPR) cutoff = 0.0017     Maximum(TPR–FPR) cutoff = 0.0028
TPR = 0.7 , FPR = 0.24               TPR = 0.91 , FPR = 0.65
AUC of convex hull = 0.787

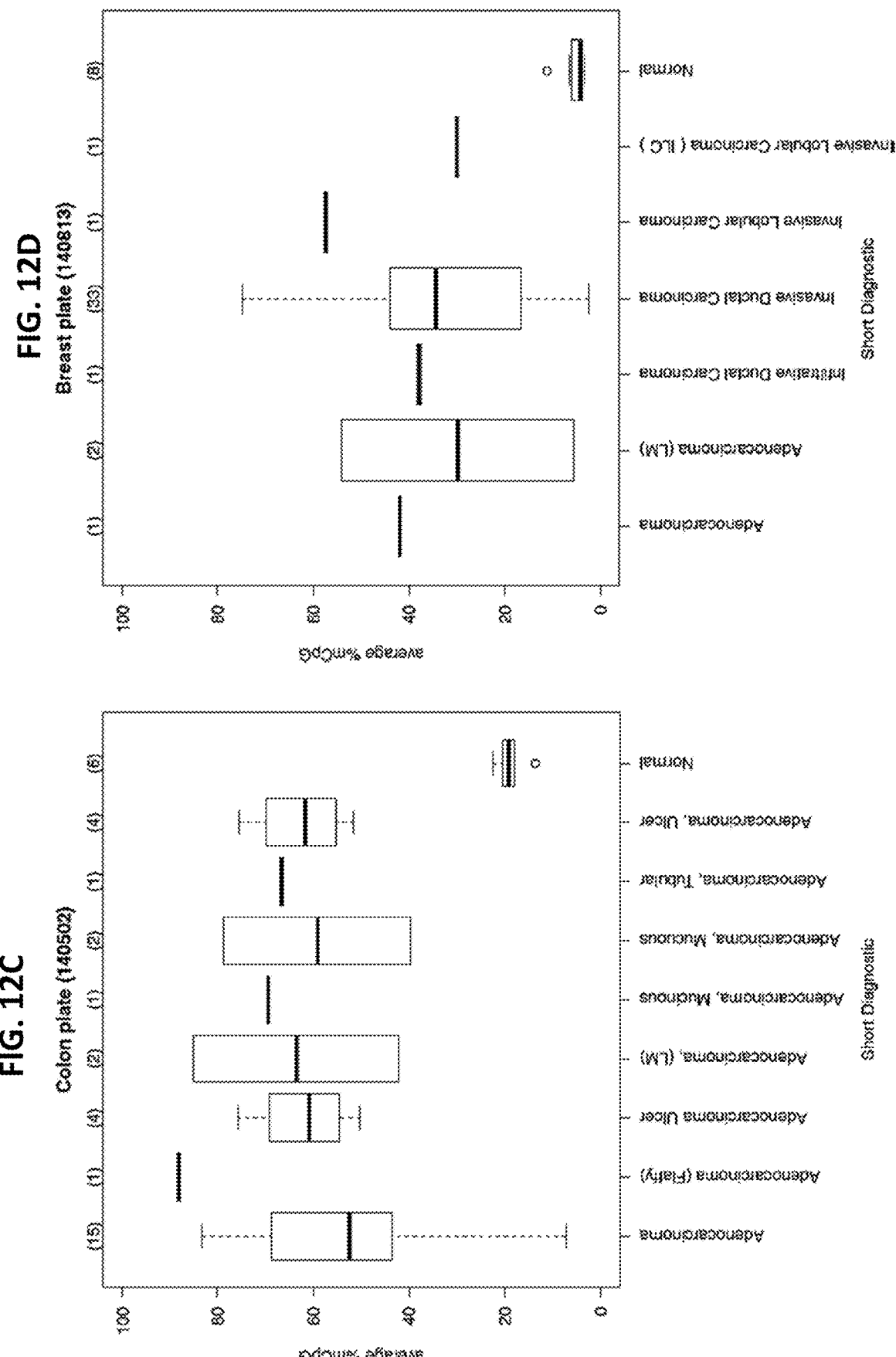

FIG. 14A
All
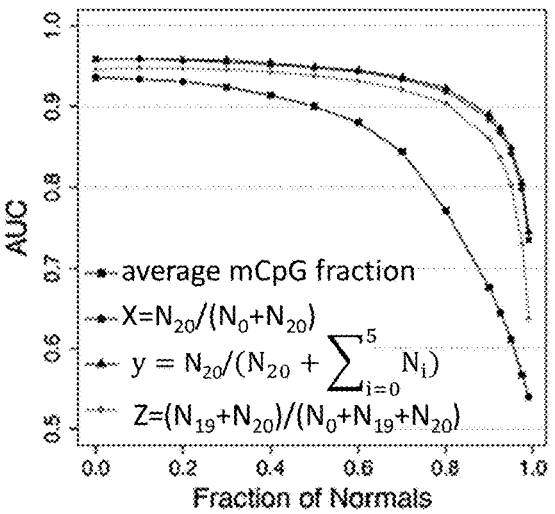
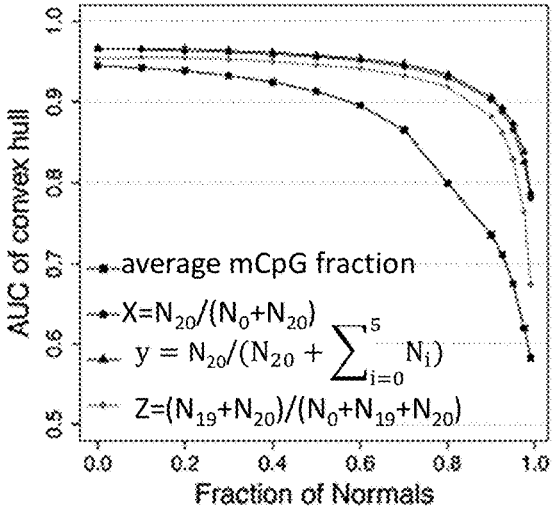
FIG. 14B
Endometrial
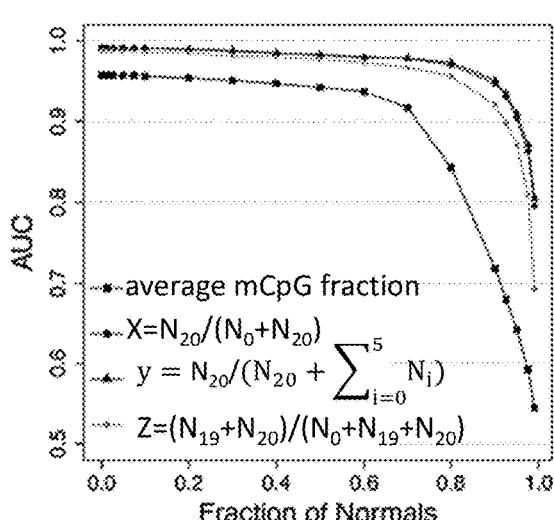
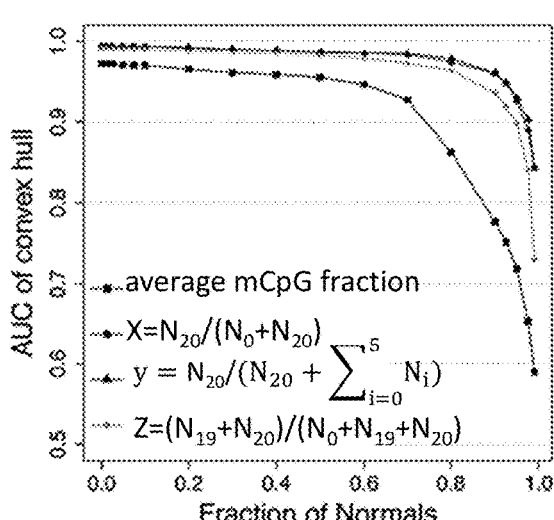

FIG. 14C
Lung
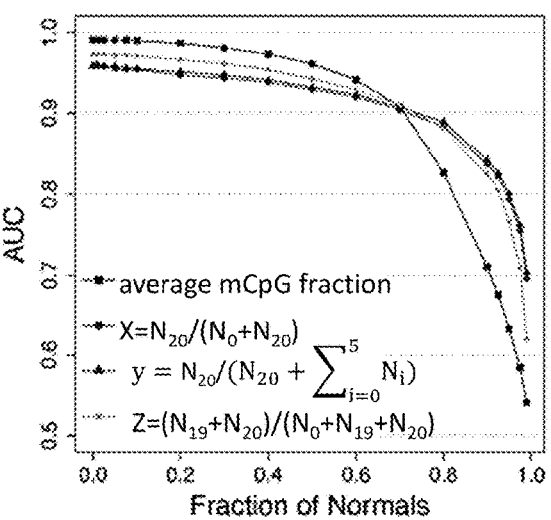
FIG. 14D
Stomach
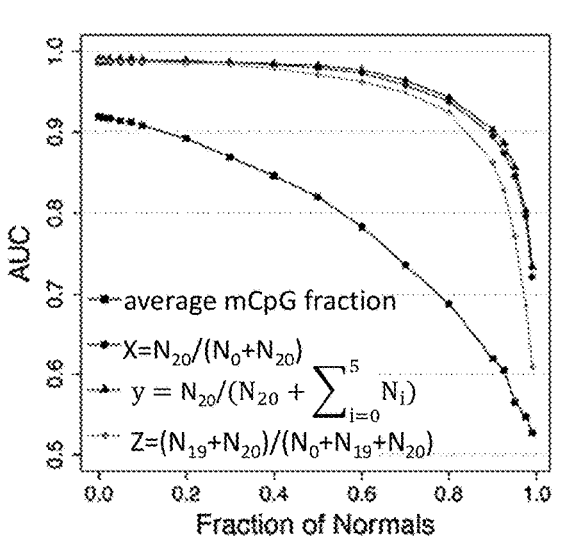
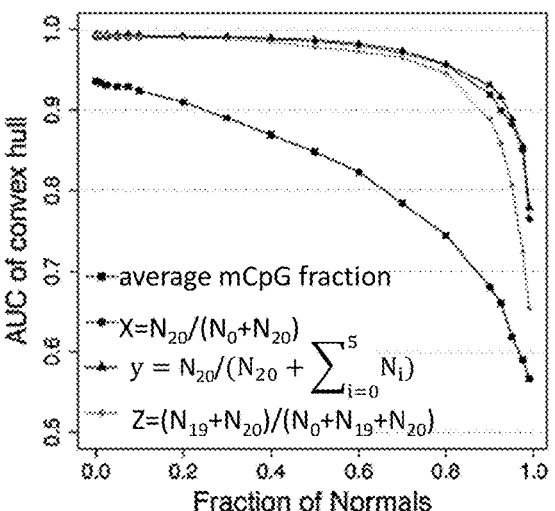

FIG. 14E

Colon

FIG. 14F

Breast

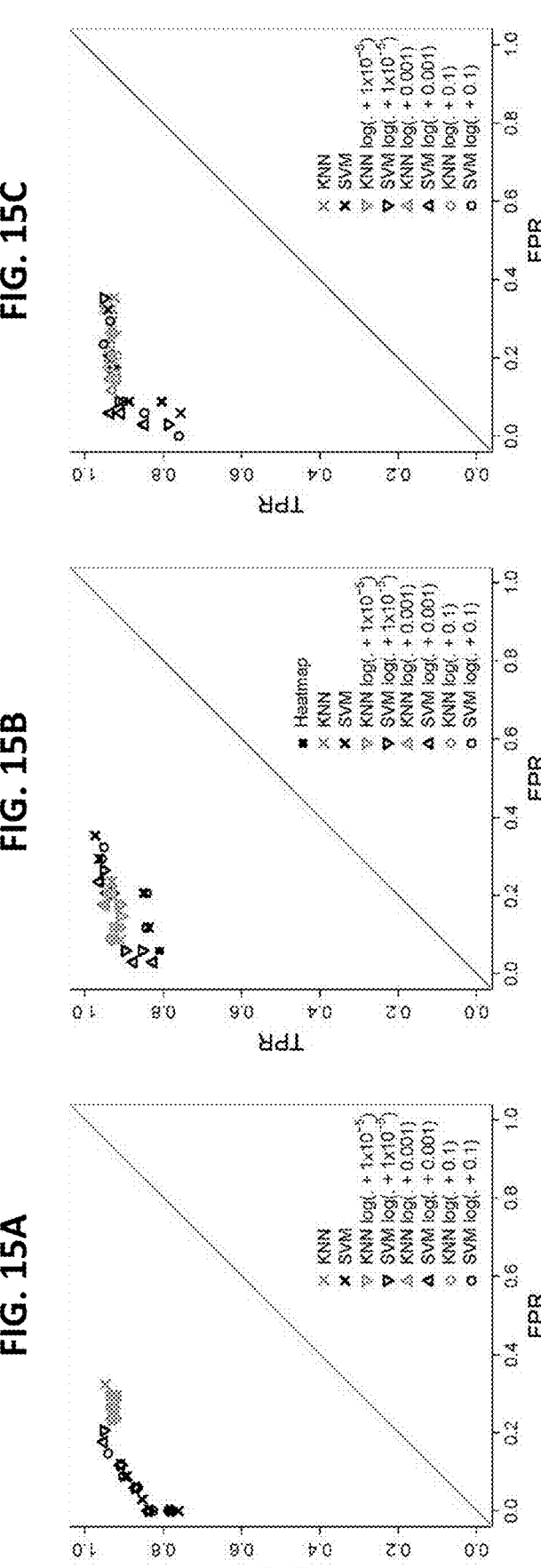

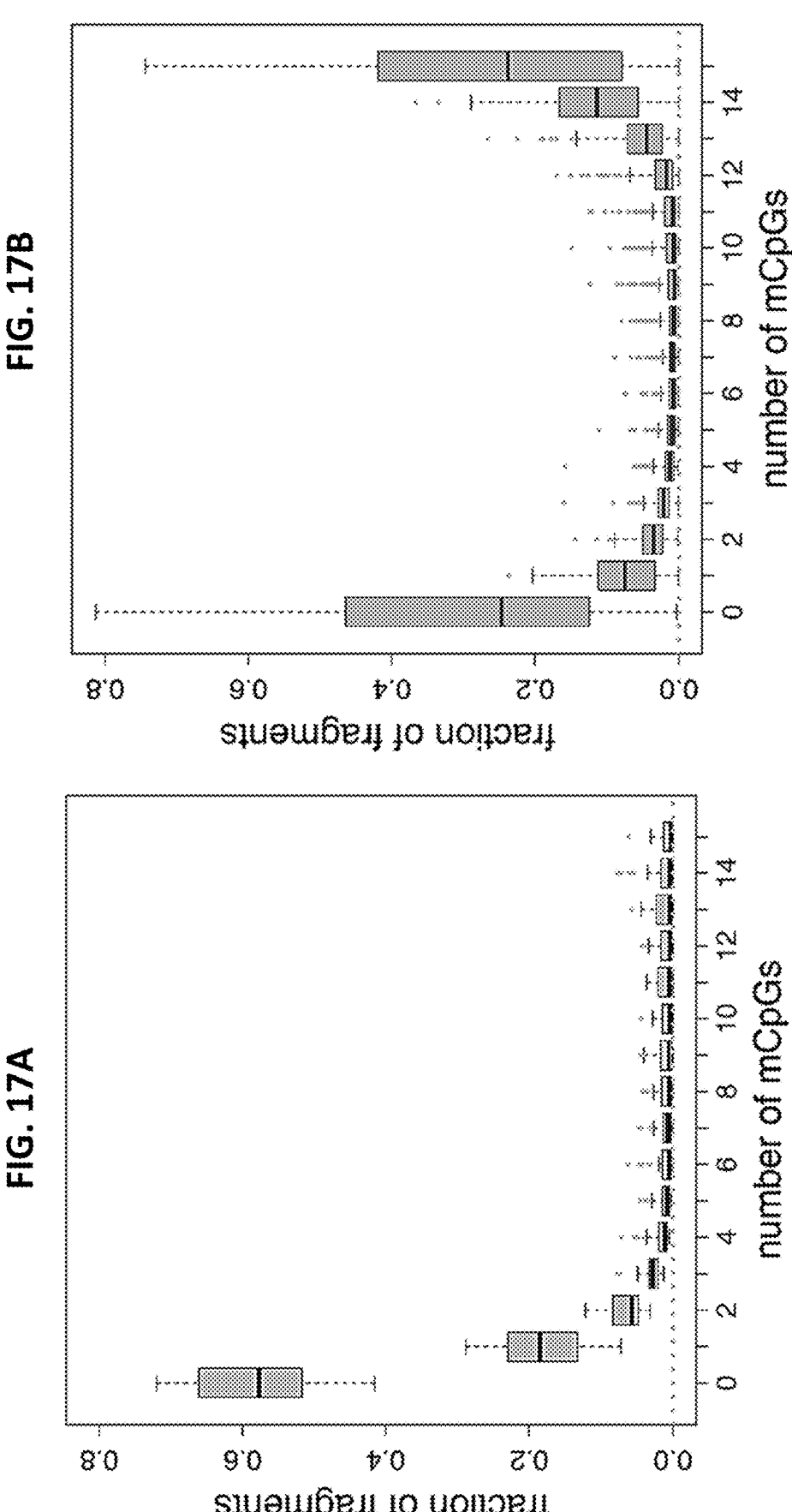

FIG. 21

The ZNF154 promoter is hypermethylated across early stage tumors

SOFTWARE 180 IMPLEMENTING TECHNOLOGIES

CANCER DETECTION METHODS

CROSS REFERENCE TO RELATED APPLICATIONS

This is a divisional of U.S. patent application Ser. No. 15/759,452, filed Mar. 12, 2018, which is the U.S. National Stage of International Application No. PCT/US2016/051905, filed Sep. 15, 2016, which was published in English under PCT Article 21(2), which in turn claims the benefit of U.S. Provisional Application No. 62/220,041, filed Sep. 17, 2015. Each of the above-identified applications is incorporated by reference herein in its entirety.

FIELD OF THE DISCLOSURE

The present disclosure relates to methods and processes for the detection of cancer and more particularly to minimally invasive cancer detection methods. The disclosure further relates to methods for detection of cancer using samples of in whole blood, such as serum or plasma. Several embodiments relate to characterization of differentially methylated genomic CpG dinucleotide sequences.

BACKGROUND

One in four deaths in the United States is due to cancer. This is despite the strong emphasis on prevention, early detection, and treatment that has lowered U.S. cancer death rates in the past two decades by 20% from their peak rates. It is important to detect cancer at earlier stages to further improve survival. The percent of cancer cases localized within a tissue, at diagnosis, differ by cancer type: for each tissue 61% female breast, 68% endometrial, 40% colorectal, 26% stomach, and 15% lung and bronchus cancers are confined to the primary site. Presently, diagnosis is made from a cadre of screening and diagnostic tools that may include physical examination, radiographic imaging, sputum cytology, blood tests, endoscopy, and/or biopsies. New technologies are changing the outlook for future testing strategies, relying heavily on genomic information. In addition to genetic mutations, epigenetic markers such as DNA methylation are also emerging as tools for disease detection. However, despite the promising and compelling aspects of DNA methylation as a diagnostic marker, there remains a general lack of consensus for an agreed upon methodology providing a principle reason for its slow implementation into clinical diagnostics.

SUMMARY

Described herein is the surprising finding that methylation of cytosines of genomic CpG dinucleotide sequences within nucleotides 58,220,424 to 58,220,670 of chromosome 19 (genome version GRCh37/hg19) occurs in multiple types of cancer, and particularly that methylation of these cytosines is highly indicative that an individual has or will have cancer.

Thus, disclosed herein are methods for diagnosing and/or prognosing an individual with cancer. In one embodiment, the methods include obtaining a biological sample containing genomic DNA from the individual, and measuring methylation of the genomic CpG dinucleotides within nucleotides 58,220,424 to 58,220,670 of chromosome 19 in the sample, wherein an increase in the level of methylation of the CpG dinucleotides in the sample compared to a control indicates an individual with cancer.

In some embodiments, a method for detecting the presence of cancer in a human individual is provided. The method comprises treating genomic DNA from a biological sample from the individual with bisulfite to detect methylation of CpG sites within the genomic DNA, and detecting the methylated CpG sites within nucleotides 58,220,424 to 58,220,670 of chromosome 19 of the genome. Detection of hypermethylation of the CpG sites within nucleotides 58,220,424 to 58,220,670 of chromosome 19 of the genomic DNA compared to a control is indicative of the presence of cancer in the individual.

In some embodiments, detecting the methylation of the CpG sites within nucleotides 58,220,424 to 58,220,670 of chromosome 19 of the genomic DNA comprises detecting the methylation status the cytosines of the 20 CpG sites are located at nucleotides 58220424, 58220440, 58220443, 58220446, 58220460, 58220466, 58220479, 58220482, 58220494, 58220500, 58220513, 58220516, 58220535, 58220567, 58220572, 58220595, 58220627, 58220657, 58220662, and 58220669 of chromosome 19.

In some embodiments, detecting the methylation of CpG sites within nucleotides 58,220,424 to 58,220,670 of chromosome 19 of the genomic DNA comprises amplifying a target nucleic acid molecule comprising the nucleotides 58,220,424 to 58,220,670 of chromosome 19 from bisulfite-treated genomic DNA to produce amplicons. The amplicons are sequenced to produce a plurality of sequence reads. The sequence reads are analyzed to determine which, if any, of the CpG sites in the corresponding genomic DNA were methylated. In some embodiments, detecting the methylation status of the 20 CpG sites comprises calculating a ratio X: $X=N_{20}/(N_0+N_{20})$, wherein $N_0$ and $N_{20}$ are frequencies of sequence reads in the plurality where 0 or 20 of the 20 CpG sites within the nucleotides 58,220,424 to 58,220,670 of chromosome 19 of the genomic DNA are methylated, respectively. Detecting an increase in the ratio X as compared with a control is indicative of cancer in the individual. In some embodiments, detecting the methylation status of the 20 CpG sites comprises calculating a ratio Y: $Y=N_{20}/(N_0+N_1+N_2+N_3+N_4+N_5+N_{20})$, wherein $N_0$, $N_1$, $N_2$, $N_3$, $N_4$, $N_5$, and $N_{20}$, are frequencies of sequence reads in the plurality where 0, 1, 2, 3, 4, 5 or 20 of the 20 CpG sites within nucleotides 58,220,424 to 58,220,670 of chromosome 19 of the genomic DNA are methylated, respectively. Detecting an increase in the ratio Y as compared with a control is indicative of cancer in the individual.

The biological sample from the individual can be, for example, a whole blood, serum, plasma, buccal epithelium, saliva, urine, stools, or bronchial aspirates sample. In preferred embodiments, the biological sample is a plasma or serum sample comprising cell-free DNA.

In several embodiments, the disclosed methods can be used to diagnose or prognose an individual with a particular type of cancer, such as lung cancer, stomach cancer, colon cancer, breast cancer, uterine cancer, bladder, head and neck, kidney, liver, ovarian, pancreas, prostate, or rectum cancer.

In additional embodiments, computer-implemented methods, computer systems, and computer readable media are provided.

The foregoing and other features and advantages of this disclosure will become more apparent from the following detailed description of several embodiments which proceeds with reference to the accompanying figures.

BRIEF DESCRIPTION OF THE DRAWINGS

FIGS. 3A-3C show a set of graphs illustrating a comparison of CpG methylation (mCpG) levels in tumor and normal endometrial samples, as determined by bisulfite-amplicon sequencing. A: Box plots of percentage of mCpG at each CpG position within the amplicon in normal (empty black) and tumor (shaded gray) samples. Samples contained a minimum of 1000 aligned reads. B: Scatterplot of tumor (T) methylation levels measured with Illumina methylation arrays at probe cg21790626 (x axis) versus amplicon sequencing at the corresponding genomic position, chr19: 58220494 (y axis), in the same samples. C: Scatterplot of the mean percentage of methylation across all amplicon CpG positions for each normal (N) sample, plotted against duplicate values.

FIGS. 4A-4D show a set of graphs illustrating the distribution of individual CpG methylation (mCpG) levels in lung (4A), stomach (4B), colon (4C), and breast (4D) tumor and normal tissue samples. Box plots of the mean percentage of methylation are shown, determined from bisulfite sequencing, at each CpG position within the amplicon in normal (empty black) and tumor (shaded gray) samples. Samples contained ≥1000 aligned reads. Also shown are scatterplots of the mean percentage of methylation across all amplicon CpG positions for tumor (T) and normal (N) samples are plotted against duplicate values, when both duplicates have at least 1000 aligned reads.

FIGS. 7A-7D show a set of graphs distinguishing tumor samples from normal tissue based on DNA methylation in endometrial, colon, stomach, lung, and breast samples. Cumulative distribution functions (CDFs) (top panel) and receiver operating characteristic (ROC) curves (bottom panel) are shown. CDFs of normal and tumor samples are in black and gray, respectively, plotted against a logarithmic x axis. ROC curves reveal the point of the maximal sum of sensitivity and specificity (gray dot). Each column contains CDFs and ROC curves corresponding to a different sample measurement, scaled to vary between 0 and 1. A: Mean fraction (percentage per 100) of methylated CpGs per sample, m. B-D: The results for the x, y, and z ratios, respectively, defined in the text. FPR, false-positive rate (ie, 1—specificity); TPR, true-positive rate (ie, sensitivity).

FIGS. 9A-9D show a set of graphs illustrating a simulation distinguishing endometrial, colon, stomach, lung, and breast tumors from normal samples when tumor signal is diluted. The graphs are arranged as in FIG. 7. Tumor signal characteristics (gray CDFs) were simulated by mixing 1% tumor signal with 99% randomly picked normal signal. Normal samples are the same as in FIG. 7 (black CDFs). A: Diluted tumors were practically indistinguishable from normal samples when relying on m, with an area under the receiver operating characteristic curve (AUC) of 0.54. B-D: By contrast, the capacity for classification persisted over dilutions for the other signal measures, x, y, and z (AUCs of 0.73, 0.75, and 0.63, from left to right). As an example of the use of the convex hull (gray off-diagonal line), C shows an increase in the AUC from 0.75 to 0.79. CDF, cumulative distribution function; FPR, false-positive rate (ie, 1—specificity); TPR, true-positive rate (ie, sensitivity).

FIGS. 12A-12D show a set of graphs illustrating the distribution of mean methylation levels in lung, stomach, colon, and breast tumor subtypes and in normal samples. The number of samples in each category is shown above the box plots.

Figures 14E, 14F:
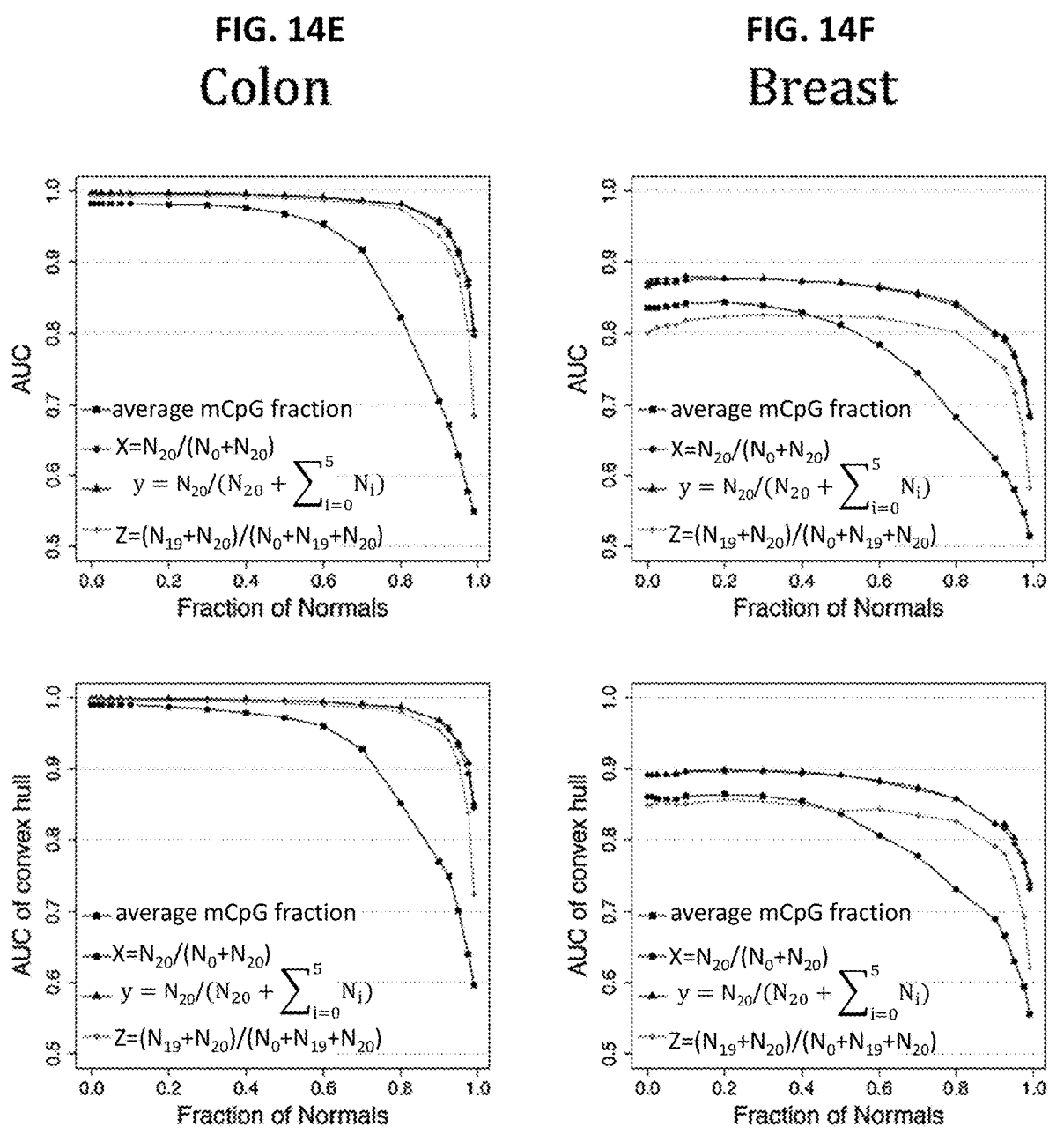

FIGS. 14A-14F show a set of graphs illustrating the performance of the four selected predictors (m, x, y, and z) in distinguishing endometrial (14B), lung (14C), stomach (14D), colon (14E), and breast (14F) tumors from normal tissues at different dilution levels. The top row shows raw areas under the receiver operating characteristic curves (AUCs), whereas the bottom row shows AUCs of the convex hulls (see FIG. 9). FIG. 14A shows all tumors pooled together, such that the top plot is identical to FIG. 8. The other columns show performance when considering endometrial, lung, stomach, colon, or breast tumors individually. The same pooled set of normal samples is used in all plots. Interestingly, the breast tumor AUC values based on all four features (m, x, y, and z) increased with dilution until approximately 20%; this was unexpected but is possible likely because of a relatively high proportion of undiluted breast tumors with methylation signals below those of pooled normal tissue samples.

FIGS. 15A-15C show a set of graphs illustrating true-positive rates (TPRs) and false-positive rates (FPRs) using k-nearest neighbors (KNN) and support vector machine (SVM) leave-one-out cross-validations to classify endometrial, colon, stomach, lung, and breast tumors versus normal tissues. Different data transformations are indicated by different symbols. Identical symbols on the same plot indicate different choices of nearest neighbors for the KNN algorithm (grey) and different cost values for the SVM algorithm (black). 15A: Results using a vector of 20 methylation values across individual CpGs for each sample (FIGS. 3 and 4). 15B: Results using methylation pattern fractions for each sample and the values derived from hierarchical clustering (FIG. 5). 15C: Results using frequency of aligned reads with different numbers of methylated CpGs, $n_k$ (FIG. 6). B also displays the values derived from hierarchical clustering (black square; cf. FIG. 5B).

FIGS. 17A-17C show a set of graphs illustrating an analysis using only the 15 leftmost CpGs (starting from the 5' end of the amplicon) of the 20 in the ZNF154 amplicon. Frequencies of aligned reads, $n_k$, with different numbers of methylated CpGs, k, from 0 to 15, in normal tissue (17A) and tumors (17B). 17C: Performance of the four selected predictors, m, x, y, and z, in tumor versus normal tissue classification. The performance of the x, y, and z-based classifications decreased substantially at greater dilutions (ie, greater fractions of normal DNA) compared with using all 20 CpGs (FIG. 8). The mean methylation CpG (mCpG) fraction-based classification did not change appreciably when compared with the analysis using all 20 CpGs but remained the worst performer among the four predictors. Note that the $n_k$ for this assay is not the same as the $n_k$ for assays involving analysis of all 20 CpG sites because truncated patterns group differently.

FIG. 21 shows a graph illustrating a bioinformatic analysis of whole genome bisulfite plasma sequencing data using the disclosed methods and showing elevated methylation in solid tumors and cancer patient plasma compared to controls

SEQUENCE LISTING

Figure 1A:
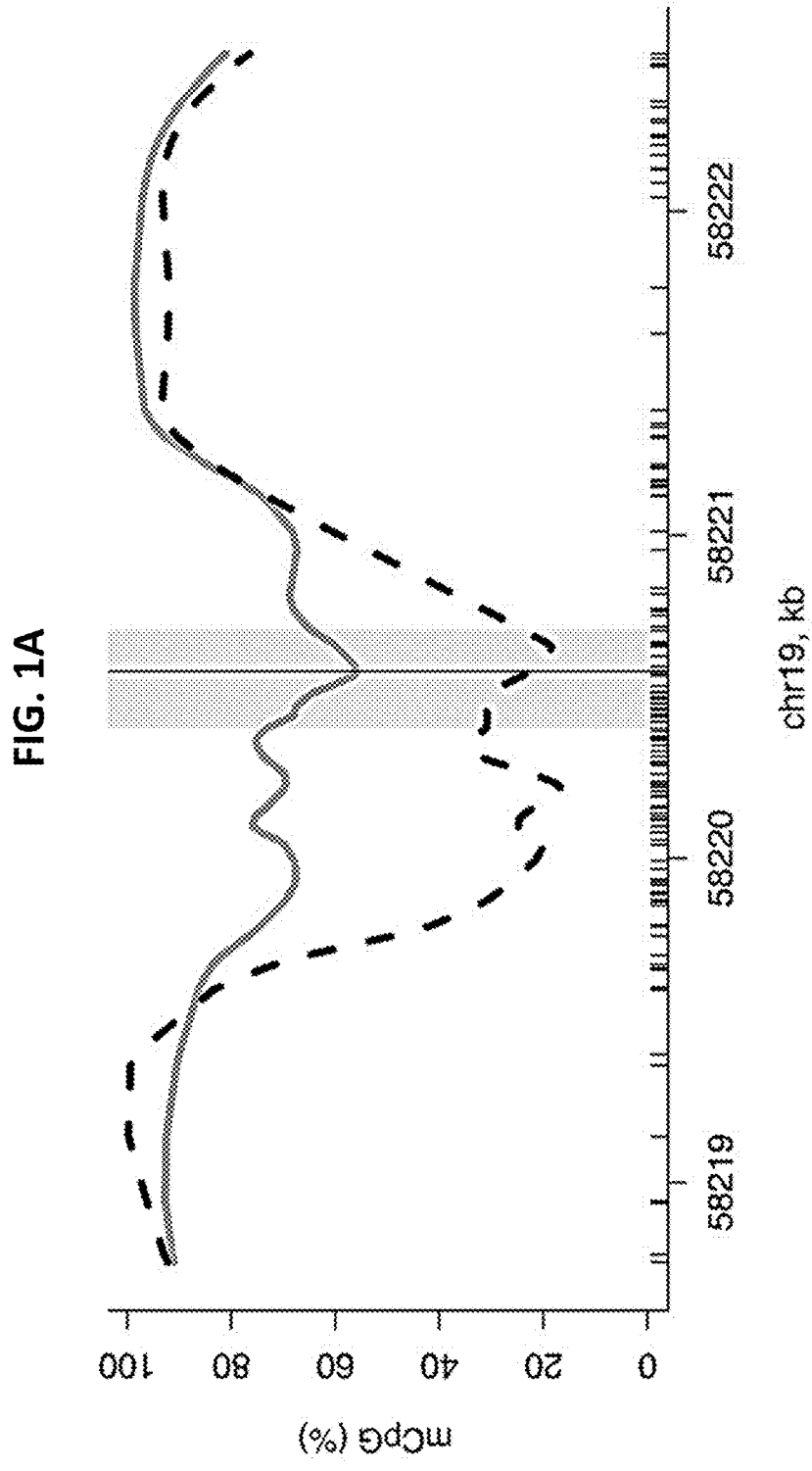
FIGS. 1A-1C show a graph and set of diagrams illustrating the DNA methylation profile around the transcription start site (TSS) of ZNF154. 1A and 1B: A smoothed CpG methylation (mCpG) profile in a colon tumor sample (gray line) and adjacent normal tissue (dashed black line), obtained from whole-genome bisulfite sequencing data (A). The rug plot illustrated along the bottom of the panel marks all CpG positions (A). The TSS (vertical line, A) and the amplicon interval (gray rectangle, A) correspond to the region of the UCSC Human Genome Browser (black rectangle, B). C: Genomic positions of 20 CpGs in the 302-bp ZNF154 amplicon: enlarged view of the TSS region and partial overlap with the annotated CpG island. The genomic coordinates shown are relative to human genome version hg19 (GRCh37).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~4 kb), which was created on Jan. 4, 2021, which is incorporated by reference herein. In the accompanying sequence listing:

DETAILED DESCRIPTION

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine,* published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Plus or minus 5% from a set amount. For example, "about 5" refers to 4.75 to 5.25. A ratio of "about 5:1" refers to a ratio of from 4.75:1 to 5.25:1.

Amplicon: The nucleic acid products resulting from the amplification of a target nucleic acid sequence. Amplification is often performed by PCR. Amplicons can range in size from 20 base pairs to 15000 base pairs in the case of long range PCR, but are more commonly 100-1000 base pairs for bisulfite-treated DNA used for methylation analysis.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The product of amplification can be characterized by such techniques as electrophoresis, restriction endonuclease cleavage patterns, oligonucleotide hybridization or ligation, and/or nucleic acid sequencing. In some embodiments, the methods provided herein can include a step of producing an amplified nucleic acid under isothermal or thermal variable conditions.

As used herein the term "selectively," when used in reference to "amplifying" (or grammatical equivalents), refers to preferentially amplifying a first nucleic acid in a sample compared to one or more other nucleic acids in the sample. The term can refer to producing one or more copies of the first nucleic acid and substantially no copies of the other nucleic acids. The term can also refer to producing a detectable amount of copies of the first nucleic acid and an undetectable (or insignificant) amount of copies of the other nucleic acids under a particular detection condition used.

Area under the curve (AUC): The area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., cancer samples and normal or control samples). ROC curves are useful for plotting the performance of a particular feature (e.g., methylation state) in distinguishing between two populations (e.g., cases having cancer and controls without cancer). Typically, the feature data across the entire population (e.g., the cases and controls) are sorted in ascending order based on the value of a single feature. Then, for each value for that feature, the true positive and false positive rates for the data are calculated.

The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

Biological Sample: A sample obtained from an individual. As used herein, biological samples include all clinical samples containing genomic DNA (such as cell-free genomic DNA) useful for cancer diagnosis and prognosis, including, but not limited to, cells, tissues, and bodily fluids, such as: blood, derivatives and fractions of blood (such as serum or plasma), buccal epithelium, saliva, urine, stools, bronchial aspirates, sputum, biopsy (such as tumor biopsy), and CVS samples. A "biological sample" obtained or derived from an individual includes any such sample that has been processed in any suitable manner (for example, processed to isolate genomic DNA for bisulfite treatment) after being obtained from the individual.

Bisulfite treatment: The treatment of DNA with bisulfite or a salt thereof, such as sodium bisulfite ($NaHSO_3$). Bisulfite reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by polymerases and amplification will result in an adenine-thymine base pair instead of a cytosine-guanine base pair.

Cancer: A cancer is a biological condition in which a malignant tumor or other neoplasm has undergone characteristic anaplasia with loss of differentiation, increased rate of growth, invasion of surrounding tissue, and which is capable of metastasis. A neoplasm is a new and abnormal growth, particularly a new growth of tissue or cells in which the growth is uncontrolled and progressive. A tumor is an example of a neoplasm. Non-limiting examples of types of cancer include lung cancer, stomach cancer, colon cancer, breast cancer, uterine cancer, bladder, head and neck, kidney, liver, ovarian, pancreas, prostate, and rectum cancer.

Cell-free DNA: DNA which is no longer fully contained within an intact cell, for example DNA found in plasma or serum.

Consists of or consists essentially of: With regard to a polynucleotide (such as primers, a target nucleic acid molecule, or an amplicon), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Control: A "control" refers to a sample or standard used for comparison with an experimental sample. In some embodiments, the control is a sample obtained from a healthy individual (such as an individual without cancer) or a non-tumor tissue sample obtained from a patient diagnosed with cancer. In some embodiments, the control is a historical control or standard reference value or range of values (such as a previously tested control sample, such as a group of cancer patients with poor prognosis, or group of samples that represent baseline or normal values, such as the level of methylation of a target nucleic acid (for example nucleotides 58,220,424 to 58,220,670 of chromosome 19 in non-tumor tissue).

CpG Site: A di-nucleotide DNA sequence comprising a cytosine followed by a guanine in the 5' to 3' direction. The cytosine nucleotides of CpG sites in genomic DNA are the target of intracellular methytransferases and can have a methylation status of methylated or not methylated. Reference to "methylated CpG site" or similar language refers to a CpG site in genomic DNA having a 5-methylcytosine nucleotide.

Detecting: To identify the existence, presence, or fact of something. General methods of detecting are known to the skilled artisan and may be supplemented with the protocols and reagents disclosed herein. Detecting can include determining if a particular nucleotide, for example a cytosine, guanine, or methylated cytosine, is present or absent in a sequence.

Diagnosis: The process of identifying a disease (such as cancer) by its signs, symptoms and results of various tests. In several embodiments a diagnosis of the presence of cancer in an individual (or an increased likelihood of the presence of the cancer in the individual) can be made based on the methylation of nucleotides 58,220,424 to 58,220,670 of chromosome 19 on genomic DNA from a sample from the individual, as described herein. The conclusion reached through that process is also called "a diagnosis." Forms of testing performed include blood tests, stool tests, medical imaging, urinalysis, endoscopy, biopsy, and epigenetic characterization of genomic DNA.

DNA (deoxyribonucleic acid): DNA is a long chain polymer which comprises the genetic material of most living organisms. The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, for instance, it is appropriate to generate probes or primers from the reverse complement sequence of the disclosed nucleic acid molecules.

Individual: A test subject or patient. The individual can be a mammal or a non-mammal In various embodiments, the individual is a mammal. A mammalian individual can be a human or non-human In various embodiments, the individual is a human A healthy or normal individual is an individual in which the disease or condition of interest (including, for example, any type of cancer) is not detectable by conventional diagnostic methods.

Label: A detectable molecule that is conjugated directly or indirectly to a second molecule, such as an oligonucleotide primer, to facilitate detection, purification, or analysis of the second molecule. The labels used herein for labeling nucleic acid molecules (such as oligonucleotide primers) are conventional. Specific, non-limiting examples of labels that can be used to label oligonucleotide primers include fluorophores and additional nucleotide sequences linked to the 5'end of the primer (for example, bar codes and adaptor sequences to facilitate sequencing reactions).

Methylation: The addition of a methyl group ($—CH_3$) to cytosine nucleotides of CpG sites in DNA. DNA methylation, the addition of a methyl group onto a nucleotide, is a post-replicative covalent modification of DNA that is catalyzed by a DNA methyltransferase enzyme. In biological systems, DNA methylation can serve as a mechanism for changing the structure of DNA without altering its coding function or its sequence.

Hypermethylation refers to significantly increased methylation in a tumor sample versus a normal sample (e.g., methylation of several cytosines in the ZNF 154 promoter comprising nucleotides 58,220,424 to 58,220,670 of chromosome 19). Hypermethylation of the ZNF 154 promoter includes but is not limited to methylation of 10-20 CpG sites (such as 15-20 or 18-20 CpG sites) within nucleotides 58,220,424 to 58,220,670 of chromosome 19. In some embodiments, hypermethylation of the ZNF154 promoter includes but is not limited to methylation of 19 or more CpG sites, 18 or more CpG sites, 17 or more CpG sites, 16 or more CpG sites, 15 or more CpG sites, 14 or more CpG sites, 13 or more CpG sites, 12 or more CpG sites, 11 or more CpG sites, or 10 or more CpG sites, of the 20 CpG sites located within nucleotides 58,220,424 to 58,220,670 of chromosome 19.

Methylation status: The state of methylation (methylated or not methylated) of the cytosine nucleotide of one or more CpG sites within a genomic sequence.

Primers: Primers are nucleic acid molecules, usually DNA oligonucleotides of about 10-50 nucleotides in length (longer lengths are also possible). Typically, primers are at least about 15 nucleotides in length, such as at least about 20, 25, 30, or 40 nucleotides in length. For example, a primer can be about 10-50 nucleotides in length, such as, 10-30, 15-20, 15-25, 15-30, or 20-30 nucleotides in length. Primers can also be of a maximum length, for example no more than 25, 30, 40, or 50 nucleotides in length. Forward and reverse primers may be annealed to a complementary target DNA strand by nucleic acid hybridization to form hybrids between the primers and the target DNA strand, and then extended along the target DNA strand by a DNA polymerase enzyme to form an amplicon. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, forward and reverse primers are used in combination in a bisulfite amplicon sequencing assay.

Prognosis: A prediction of the course of a disease, such as cancer. The prediction can include determining the likelihood of an individual to develop aggressive, recurrent disease, to develop one or more metastases, to survive a particular amount of time (e.g., determine the likelihood that an individual will survive 1, 2, 3, 4, 5, or more years), to respond to a particular therapy (e.g., chemotherapy), or combinations thereof. The prediction can also include determining whether an individual has a malignant or a benign tumor.

Sensitivity and specificity: Statistical measurements of the performance of a binary classification test. Sensitivity measures the proportion of actual positives which are correctly. Specificity measures the proportion of negatives which are correctly identified.

Sequence Read: A sequence (e.g., of about 300 bp) of contiguous base pairs of a nucleic acid molecule. The sequence read may be represented symbolically by the base pair sequence (in ATCG) of the sample portion. It may be stored in a memory device and processed as appropriate to determine whether it matches a reference sequence or meets other criteria. A sequence read may be obtained directly from a sequencing apparatus or indirectly from stored sequence information concerning a sample.

Target nucleic acid molecule: A nucleic acid molecule whose detection, amplification, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule of which the amplification and/or evaluation of methylation status is intended. Purification or isolation of the target nucleic acid molecule, if needed, can be conducted by methods known to those in the art, such as by using a commercially available purification kit or the like.

Tumor: An abnormal growth of cells, which can be benign or malignant. Cancer is a malignant tumor, which is characterized by abnormal or uncontrolled cell growth.

Features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

An "established" or "existing" tumor is an existing tumor that can be discerned by diagnostic tests. In some embodiments, and established tumor can be palpated. In some embodiments, and "established tumor" is at least 500 mm$^3$, such as at least 600 mm$^3$, at least 700 mm$^3$, or at least 800 mm$^3$ in size. In other embodiments, the tumor is at least 1 cm long. With regard to a solid tumor, and established tumor generally has a robust blood supply, and has induced Tregs and myeloid derived suppressor cells (MDSC).

II. Detecting Cancer

The present disclosure relates to diagnosis and prognosis of cancer using DNA methylation of a region of the promoter of the ZNF154 gene on chromosome 19 as a biomarker. Having identified this region as a highly sensitive and specific cancer marker, methods of detecting, diagnosing or prognosing cancer, or a predilection to cancer, in an individual are disclosed. As disclosed herein, the methylation status of nucleotides 58,220,424 to 58,220,670 of chromosome 19 can be used as a biomarker for diagnosis and prognosis of many different types of cancer, including but not limited to lung cancer, stomach cancer, colon cancer, breast cancer, uterine cancer, bladder, head and neck, kidney, liver, ovarian, pancreas, prostate, and rectum cancer.

Unless context indicated otherwise, reference to nucleotides 58,220,424 to 58,220,670 of chromosome 19 refers to the corresponding nucleotides on chromosome 19 of the human genome version GRCh37/hg19. The DNA sequence of the forward strand of this region of chromosome 19 in human genome version GRCh37/hg19 is set forth as nucleotides 21-267 of SEQ ID NO: 5:

```
CGTGGGTCCCCCAGGGCGGCGTCGCCAAGGCTTAGACGCTTTCGTGCAGG

AGGGACGACGACTCCCCTCACGCCTTCGTGGCCCCAACTCGGCGCTCTGC

TATCTCTGATCCGGTGAACACACCTCAGAGAAGCTAAAATGGCCGCCACG

AAGAGGCCCCCCCAAAAGTCCCGTCCTTTCTTTTTGTGACTCTCAAGGAA

AGTCGGTTTTCTGAGCTCTTACTGGCTTAGTAGCGTGGCGTTCAACG
```

Unless context indicated otherwise, reference to a particular CpG site position refers the position of the cytosine nucleotide of the CpG site in the forward strand of chromosome 19 of the human genome version GRCh37/hg19. There are 20 CpG sites located on each strand (forward and reverse) of nucleotides 58,220,424 to 58,220,670 of chromosome 19 (nucleotides 21-267 of SEQ ID NO: 5). The cytosines of the CpG sites on the forward strand are located at nucleotides 58220424, 58220440, 58220443, 58220446, 58220460, 58220466, 58220479, 58220482, 58220494, 58220500, 58220513, 58220516, 58220535, 58220567, 58220572, 58220595, 58220627, 58220657, 58220662, and 58220669 of chromosome 19. These positions correspond to nucleotides 21, 37, 40, 43, 57, 63, 76, 79, 91, 97, 110, 113, 132, 134, 169, 192, 224, 254, 259, and 266 of SEQ ID NO: 5. As disclosed herein, the methylation status of these cytosines can be used as a biomarker for diagnosis and prognosis of many different types of cancer, including but not limited to lung cancer, stomach cancer, colon cancer, breast cancer, uterine cancer, bladder, head and neck, kidney, liver, ovarian, pancreas, prostate, and rectum cancer.

It should be noted that CpG sites are symmetric in the forward (+) and reverse (−) strands of DNA (as C pairs to G and G to C). Therefore, the methods and systems provided herein for analysis of the methylation status of CpG sites in nucleotides 58,220,424 to 58,220,670 of chromosome 19 can be applied to either or both of the forward and reverse strands of this region of the human genome. In the context of the reverse strand, the genome position of the cytosine of a CpG site is in an n+1 position. In some embodiments, the methylation status of CpG sites in the forward strand of nucleotides 58,220,424 to 58,220,670 of chromosome 19 are analyzed according to the methods and systems provided herein. In some embodiments, the methylation status of CpG sites in the reverse strand of nucleotides 58,220,424 to 58,220,670 of chromosome 19 are analyzed according to the methods and systems provided herein. In some embodiments, the methylation status of CpG sites in the forward and reverse strands of nucleotides 58,220,424 to 58,220,670 of chromosome 19 are analyzed according to the methods and systems provided herein.

Detecting cancer in an individual can include obtaining a biological sample from the individual. The sample can be any sample that includes genomic DNA. Such samples include, but are not limited to, tissue from biopsies (including formalin-fixed paraffin-embedded tissue), autopsies, and pathology specimens; sections of tissues (such as frozen sections or paraffin-embedded sections taken for histological purposes); body fluids, such as blood, sputum, serum, ejaculate, or urine, or fractions of any of these; and so forth. In one particular example, the sample from the individual is a tissue biopsy sample. In another specific example, the sample from the individual is urine. In some embodiments the biological sample is a plasma or serum sample comprising cell-free DNA. In several embodiments, the biological sample is from an individual suspected of having a cancer, such as stomach cancer, colon cancer, breast cancer, uterine cancer, bladder, head and neck, kidney, liver, ovarian, pancreas, prostate, or rectum cancer. In some embodiments, the biological sample is a tumor sample or a suspected tumor sample. For example, the sample can be a biopsy sample from at or near or just beyond the perceived leading edge of a tumor in an individual. Testing of the sample using the methods provided herein can be used to confirm the location of the leading edge of the tumor in the individual. This information can be used, for example, to determine if further surgical removal of tumor tissue is appropriate.

In some embodiments, an amplicon generated from cell-free DNA derived from blood (or a portion thereof, such as plasma or serum) can be used to detect the methylation of circulating tumor DNA (ctDNA). There are many studies detecting and assessing the fraction of ctDNA based on mutations. However, mutation-based detection is only specific to the tumors harboring those mutations and without a detailed understanding of normal samples it is not always clear what levels of ctDNA should be considered abnormal and warrant intervention. Conversely, methylation within nucleotides 58,220,424 to 58,220,670 of chromosome 19 of the genomic DNA may be similar throughout different tumor types and may complement mutation markers for better diagnosis.

In some embodiments, the disclosed methods include detecting methylation of CpG sites within nucleotides 58,220,424 to 58,220,670 of chromosome 19 (such as the presence of methylation or an increase in methylation compared to a control) in a sample from an individual. In some examples, hypermethylation of CpG sites within nucleotides 58,220,424 to 58,220,670 of chromosome 19 in the sample (for example as compared to a control) detects cancer in the individual or diagnoses the individual with cancer. In particular examples, hypermethylation of CpG sites within nucleotides 58,220,424 to 58,220,670 of chromosome 19 includes an increase in methylation of the target sequence by at least 10% (such as at least about 25%, 50%, 75%, 2-fold, 3-fold, 5-fold, 10-fold, or more) as compared to a control, such as a non-tumor sample.

In several embodiments, methylation of CpG sites within nucleotides 58,220,424 to 58,220,670 of chromosome 19 is detected using bisulfite-amplicon sequencing (see, e.g., Frommer, et al., *Proc Natl Acad Sci USA* 89(5): 1827-31, 1992; Feil, et al., *Nucleic Acids Res.* 22(4): 695-6, 1994). Bisulfite-amplicon sequencing involves treating genomic DNA from a sample with bisulfite to convert unmethylated cytosine to uracil followed by amplification (such as PCR amplification) of a target nucleic acid (such as a target nucleic acid comprising or consisting of nucleotides 58,220, 424 to 58,220,670 of chromosome 19) within the treated genomic DNA, and sequencing of the resulting amplicon. Sequencing produces reads that can be aligned to a genomic reference sequence that can be used to quantitate methylation levels of all the sequential CpGs within an amplicon. Cytosines in non-CpG context can be used to track bisulfite conversion efficiency for each individual sample. The procedure is both time and cost-effective, as multiple samples can be sequenced in parallel using a 96 well plate, and generates reproducible measurements of methylation when assayed in independent experiments.

The amplicon selected for the bisulfite-amplicon sequencing assay preferentially covers nucleotides 58,220,424 to 58,220,670 of chromosome 19. In some embodiments, the amplicon can be limited to this region, for example, the amplicon can consist essentially of nucleotides 21-267 of SEQ ID NO: 5. In some embodiments, the amplicon includes nucleotides 58,220,424 to 58,220,670 of chromosome 19, and from 0-500 nucleotides of the genome on either end (5' and 3') of nucleotides 58,220,424 to 58,220, 670, that is, the 5' end of the amplicon can be a nucleotide from nucleotides 558, 219, 924 to 8,220,424, and the 3' end of the amplicon can be a nucleotide from nucleotides 58,220,670 to 58,221,170. In some embodiments, the amplicon includes nucleotides 58,220,424 to 58,220,670 of chromosome 19, and from 0-200 nucleotides of the genome on either end (5' and 3') of nucleotides 58,220,424 to 58,220, 670, that is, the 5' end of the amplicon can be a nucleotide from nucleotides 558, 220, 224 to 8,220,424, and the 3' end of the amplicon can be a nucleotide from nucleotides 58,220,670 to 58,221,870.

In some embodiments, the amplicon comprises, consists essentially of, or consists of nucleotides 58,220,404 to 58,220,705 of chromosome 19. In the human genome version GRCh37/hg19, these sequence of these nucleotides is set forth as SEQ ID NO: 5:

GGTCCCTATCCCAGGCCTGACGTGGGTCCCCCAGGGCGGCGTCGCCAAGG

CTTAGACGCTTTCGTGCAGGAGGGACGACGACTCCCCTCACGCCTTCGTG

GCCCCAACTCGGCGCTCTGCTATCTCTGATCCGGTGAACACACCTCAGAG

AAGCTAAAATGGCCGCCACGAAGAGGCCCCCCCAAAAGTCCCGTCCTTTC

TTTTTGTGACTCTCAAGGAAAGTCGGTTTTCTGAGCTCTTACTGGCTTAG

TAGCGTGGCGTTCAACGCAGAGCATTCTAGGTAATGTAGTTTTCATAGAT

CC

An appropriate primer pair for amplifying the amplicon is selected. In some embodiments, the forward primer comprises, consists essentially of, or consists of SEQ ID NO: 1, and the reverse primer comprises, consists essentially of, or consists of SEQ ID NO: 2 or SEQ ID NO: 6. The primers can have a maximum length, such as no more than 75 nucleotides in length (for example, no more than 50 nucleotides in length). In several embodiments, the forward and/or reverse primers can be labeled (for example, with adapter sequences or barcode sequences) to facilitate sequencing or purification of the amplicons.

The sequence reads produced from the bisulfite-amplicon sequencing of the genomic DNA from the sample from the individual are analyzed to determine the methylation of nucleotides 58,220,424 to 58,220,670 of chromosome 19. For example, the methylation of CpG sites can be determined for each sequenced and properly aligned read (DNA fragment) by counting the number, k, of methylated CpGs in the region of the amplicon corresponding to nucleotides 58,220,424 to 58,220,670 of chromosome 19 (k will be between 0 and 20). In several embodiments, reads with identical k are grouped together and the frequency of each group, $n_k$, is calculated ($n_k$ is the frequency of reads with exactly k methylated CpGs). Thus each sample is characterized by a set/collection of frequencies, $\{n_k\}$, with k ranging from 0 to 20.

The frequencies of the numbers of methylated CpG from the sequence reads can be used as an indicator of whether or not the individual has cancer. As discussed in the examples, the two sequence read groups with the strongest differential representation are the fully unmethylated and fully methylated reads. Focusing on just these two groups, a ratio $X=N_{20}/(N_0+N_{20})$ can be used to provide an indication as to whether or not the individual has cancer, that is, to distinguish tumor from normal tissue samples. In ratio X, $N_0$ and $N_{20}$ are frequencies of sequence reads in the plurality where 0 or 20 of the 20 CpG sites within the nucleotides 58,220,424 to 58,220,670 of chromosome 19 of the genomic DNA are methylated, respectively. An increase in the ratio X as compared with a control (such as a threshold value of corresponding non-tumor samples) is indicative of cancer in the individual. In some embodiments, the increase can be a 50% increase, such as a 100% increase, or more, compared to an appropriate control. In some embodiments, a finding of no increase in the ratio X as compared with a control (such as a threshold value of corresponding non-tumor samples) indicates that the individual does not have cancer.

In additional embodiments, sequence reads with low methylation (for example, five or fewer methylated CpGs) are combined with fully unmethylated reads to provide an indication as to whether or not the individual has cancer, that is, to distinguish tumor from normal tissue samples. In some such embodiments, a ratio $Y=N_{20}/(N_0+N_1+N_2+N_3+N_4+N_5+N_{20})$ can be used to provide an indication as to whether or not the individual has cancer, that is, to distinguish tumor from normal tissue samples. In ratio Y, $N_0$, $N_1$, $N_2$, $N_3$, $N_4$, $N_5$, and $N_{20}$, are frequencies of sequence reads in the plurality where 0, 1, 2, 3, 4, 5 or 20 of the 20 CpG sites within nucleotides 58,220,424 to 58,220,670 of chromosome 19 of the genomic DNA are methylated, respectively. An increase in the ratio Y as compared with a control (such as a threshold value of corresponding non-tumor samples) is indicative of cancer in the individual. In some embodiments, the increase can be a 50% increase, such as a 100% increase, or more, compared to an appropriate control. In some embodiments, a finding of no increase in the ratio Y as compared with a control (such as a threshold value of corresponding non-tumor samples) indicates that the individual does not have cancer.

In additional embodiments, sequence reads with almost-fully methylated reads are combined with fully methylated reads to provide an indication as to whether or not the individual has cancer, that is to distinguish tumor from normal tissue samples. In some such embodiments, a ratio $Z=(N_{19}+N_{20})/(N_0+N_{19}+N_{20})$ can be used to provide an indication as to whether or not the individual has cancer, that is to distinguish tumor from normal tissue samples. In ratio Z, $N_0$, $N_{19}$, and $N_{20}$, are frequencies of sequence reads in the plurality where 0, 19, or 20 of the 20 CpG sites within nucleotides 58,220,424 to 58,220,670 of chromosome 19 of the genomic DNA are methylated, respectively. An increase in the ratio Z as compared with a control (such as a threshold value of corresponding non-tumor samples) is indicative of cancer in the individual. In some embodiments, the increase can be a 50% increase, such as a 100% increase, or more, compared to an appropriate control. In some embodiments, a finding of no increase in the ratio Z as compared with a control (such as a threshold value of corresponding non-tumor samples) indicates that the individual does not have cancer.

In another aspect, there are many ways methylation within nucleotides 58,220,424 to 58,220,670 of chromosome 19 of genomic DNA may be further utilized to improve its use as a biomarker for cancer. While direct measurement of the methylation signal from body fluid samples is a preferred method, addition of multiple genomic loci may increase diagnostic power. A panel of regions of interest may facilitate a pan-cancer biomarker's ability to detect the presence of tumor DNA and determine subtypes. Another factor that may potentially help in distinguishing tumors from normals is spiking in internal DNA standards to quantify DNA concentration in blood. That information can be used to quantify the number of fully methylated reads in unit volume of blood, which might serve as a useful additional discriminative tumor signature. Other absolute quantification methods, like ddPCR (digital droplet PCR), might be used as well.

In one aspect, the present disclosure provides a methodology for detecting the presence of cancer in an individual by detecting the frequency of signal of modified DNA molecules that correlates with the presence of cancer in an individual, more specifically a hypermethylation signal of nucleotides 58,220,424 to 58,220,670 of chromosome 19 in circulating tumor DNA.

Bisulfite-amplicon sequencing potentially recovers all read patterns present in the sample and allows a more detailed analysis of methylation. Using this approach, hypermethylation of nucleotides 58,220,424 to 58,220,670 of chromosome 19 may be utilized as a pan-cancer biomarker for ctDNA in methods for diagnosing tumors and/or to track effectiveness of chemotherapy from the blood.

The disclosed methods also include determining the prognosis of an individual with cancer, such as predicting the outcome (for example, likelihood of aggressive disease, recurrence, metastasis, or chance of survival) of the individual. The method includes determining the presence or absence and/or absolute or relative amount of methylation of one or more target nucleic acids (e.g., nucleotides 58,220, 424 to 58,220,670 of chromosome 19) in the sample, for example, utilizing the methods described above. In some examples, presence of hypomethylation of a target sequence indicates a good prognosis (for example, a diagnosis of no cancer or increased chance of survival in the individual). In an example, an increased chance of survival includes a survival time of at least 60 months from time of diagnosis, such as 60 months, 80 months, 100 months, or more from time of diagnosis or first treatment. In other examples, a good prognosis includes a lower Gleason score (such as a score of 7 or less).

Alternative methods to assay the methylation status of CpG sites can also be used. Numerous DNA methylation detection methods are known in the art, including but not limited to: methylation-specific enzyme digestion (Singer-Sam, et al., *Nucleic Acids Res.* 18(3): 687, 1990; Taylor, et al., *Leukemia* 15(4): 583-9, 2001), methylation-specific PCR (MSP or MSPCR) (Herman, et al., *Proc Natl Acad Sci USA* 93(18): 9821-6, 1996), methylation-sensitive single nucleotide primer extension (MS-SnuPE) (Gonzalgo, et al., *Nucleic Acids Res.* 25(12): 2529-31, 1997), restriction landmark genomic scanning (RLGS) (Kawai, *Mol Cell Biol.* 14(11): 7421-7, 1994; Akama, et al., *Cancer Res.* 57(15): 3294-9, 1997), and differential methylation hybridization (DMH) (Huang, et al., *Hum Mol Genet.* 8(3): 459-70, 1999). See also the following issued U.S. Pat. Nos. 7,229,759; 7,144,701; b 7,125,857; 7,118,868; 6,960,436; 6,905,669; 6,605,432; 6,265,171; 5,786,146; 6,017,704; and 6,200,756; each of which is incorporated herein by reference.

Any suitable amplification methodology can be utilized to selectively or non-selectively amplify one or more nucleic acid molecules from a sample according to the methods and systems presented herein. It will be appreciated that any of the amplification methodologies described herein or generally known in the art can be utilized with target-specific primers to selectively amplify a nucleic acid molecule of interest. Suitable methods for selective amplification include, but are not limited to, the polymerase chain reaction (PCR), strand displacement amplification (SDA), transcription mediated amplification (TMA) and nucleic acid sequence based amplification (NASBA), degenerate oligonucleotide primed polymerase chain reaction (DOP-PCR), primer-extension preamplification polymerase chain reaction (PEP-PCR). The above amplification methods can be employed to selectively amplify one or more nucleic acids of interest. For example, PCR, including multiplex PCR, SDA, TMA, NASBA, DOP-PCR, PEP-PCR, and the like can be utilized to selectively amplify one or more nucleic acids of interest. In such embodiments, primers directed specifically to the nucleic acid of interest are included in the amplification reaction. In some embodiments, selectively amplifying can include one or more non-selective amplification steps. For example, an amplification process using random or degenerate primers can be followed by one or more cycles of amplification using target-specific primers.

In some examples, methylation of CpG sites within nucleotides 58,220,424 to 58,220,670 of chromosome 19 is detected by methylation-specific polymerase chain reaction (MSPCR). In a specific example, DNA is isolated from a sample from an individual, bisulfite treated, converting all unmethylated, but not methylated, cytosines to uracil, and a target nucleic acid molecule comprising nucleotides 58,220, 424 to 58,220,670 of chromosome 19 is amplified with primers that specifically amplify methylated DNA and/or a region of the nucleotides 58,220,424 to 58,220,670 of chromosome 19 is amplified with primers that specifically amplify unmethylated DNA, thereby detecting methylation (or methylation status) of nucleotides 58,220,424 to 58,220, 670 of chromosome 19.

In other examples, methylation of CpG sites within nucleotides 58,220,424 to 58,220,670 of chromosome 19 is detected by hybridization (for example using a microarray), such as hybridization of a methylation-specific probe. In a specific example, DNA is isolated from a sample from an individual and is hybridized with a nucleic acid probe specific for a potentially methylated cytosine residue within the target.

In further examples, methylation of CpG sites within nucleotides 58,220,424 to 58,220,670 of chromosome 19 is detected using one or more methylation specific restriction endonucleases (such as MspI, HpaII or BssHII). In a particular example, DNA is isolated from a sample from an individual and treated with a restriction endonuclease that recognizes a restriction site within nucleotides 58,220,424 to 58,220,670 of chromosome 19 and which does not cleave at the restriction site when a cytosine in the restriction site is methylated. In some examples, the method also includes carrying out an amplification reaction (for instance, a PCR amplification reaction) of at least a portion of the target nucleic acid molecule using the resulting treated DNA as a template, wherein the portion of the target nucleic acid contains the restriction site and is amplified only when the restriction site has not been cleaved by the restriction endonuclease.

In some embodiments presented herein, the methods comprise carrying out one or more sequencing reactions to generate sequence reads of at least a portion of a nucleic acid such as an amplified nucleic acid molecule (e.g. an amplicon or copy of a template nucleic acid). The identity of nucleic acid molecules can be determined based on the sequencing information.

Paired-end sequencing allows the determination of two reads of sequence from two places on a single polynucleotide template. One advantage of the paired-end approach is that although a sequencing read may not be long enough to sequence an entire target nucleic acid, significant information can be gained from sequencing two stretches from each end of a single template.

In some embodiments, each sequencing read is of sufficient length to sequence the portion of the amplicon comprising nucleotides 58,220,424 to 58,220,670 of chromosome 19. In other embodiments, two paired sequence reads that cover the portion of the amplicon comprising nucleotides 58,220,424 to 58,220,670 of chromosome 19 are used to obtain the sequence of the comprising nucleotides 58,220, 424 to 58,220,670 of chromosome 19.

In some embodiments of the methods provided herein, one or more copies of the amplified nucleic acid molecule, such as an amplicon of nucleotides 58,220,424 to 58,220, 670 of chromosome 19 from bisulfite treated genomic DNA is sequenced a plurality of times. It can be advantageous to perform repeated sequencing of an amplified nucleic acid molecule in order to ensure a redundancy sufficient to overcome low accuracy base calls. Because sequencing error rates often become higher with longer read lengths, redundancy of sequencing any given nucleotide can enhance sequencing accuracy. Thus, in some embodiments, sequencing reads of the amplicon of nucleotides 58,220,424 to 58,220,670 of chromosome 19 from bisulfite treated genomic DNA are performed multiple times.

The number of sequencing reads of a nucleotide or nucleic acid is referred to as sequencing depth. In some embodiments, a sequencing read of at least the first region or second region of the amplified exon pair is performed to a depth of at least 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 900, 950 or at least 1000x. In typical embodiments, the accuracy in determining methylation of a genomic DNA sample increases proportionally with the number of reads.

The sequencing reads described herein may be obtained using any suitable sequencing methodology, such as direct sequencing, including sequencing by synthesis (SBS), sequencing by hybridization, and the like. Exemplary SBS procedures, fluidic systems and detection platforms that can be readily adapted for use with amplicons produced by the methods of the present disclosure are described, for example, in Bentley et al., *Nature* 456:53-59 (2008), WO 04/018497; U.S. Pat. No. 7,057,026; WO 91/06678; WO 07/123,744; U.S. Pat. Nos. 7,329,492; 7,211,414; 7,315,019; 7,405,281, and US 2008/0108082, each of which is incorporated herein by reference. An exemplary sequencing system for use with the disclosed methods is the Illumina MiSeq platform.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference).

In another aspect, reagents and kits are provided for bisulfite amplicon sequencing of the ZNF154 promoter. The kits include forward and reverse primers to amplify potential methylation sites near the ZNF154 TSS. In some embodiments, the kit can include one or more containers containing forward and/or reverse primers for amplifying a target nucleic acid molecule comprising or consisting of nucleotides 58,220,424 to 58,220,670 of chromosome 19 of genomic DNA. The target nucleic acid molecule can have a maximum length, for example no more than 1000 (such as no more than 750, no more than 500, no more than 400, or no more than 350) nucleotides in length. In some embodiments, the target nucleic acid molecule comprises or consists of the nucleic acid sequence set forth as SEQ ID NO: 5, or nucleotides 21-267 of SEQ ID NO: 5. In some embodiments, the forward primer comprises, consists essentially of, or consists of SEQ ID NO: 1, and the reverse primer comprises, consists essentially of, or consists of SEQ ID NO: 2 or SEQ ID NO: 6. The primers can have a maximum length, such as no more than 75 nucleotides in length (for example, no more than 50 nucleotides in length). In several embodiments, the forward and/or reverse primers in the kit can be labeled. Also included are sodium bisulfite reagents as well as reagents used for amplicon sequencing. The kit may also include adapter sequences for the amplicon.

In several embodiments, the disclosed methods for detecting, diagnosing or prognosing cancer involve classifying the methylation status of a cancer biomarker in a sample of genomic DNA from a subject. Accordingly, in some embodiments a method is provided comprising classifying the methylation status of a cancer biomarker in a sample of genomic DNA from a subject. The cancer biomarker comprises the methylation status of CpG sites within nucleotides 58,220,424 to 58,220,670 of chromosome 19 of genomic DNA. In some embodiments, the method comprises detecting the methylation status of 20 CpG sites with nucleotides 58,220,424 to 58,220,670 of chromosome 19 of the genomic DNA. The detection step can involve a bisulfite-amplicon sequencing assay to detect cytosines in the CpG sites of the cancer biomarker that are methylated (or not) in the genomic DNA from the sample. In several embodiments, detection of hypermethylation of the CpG sites in the indicated region of chromosome 19 can be used to classify the cancer biomarker as hypermethylated or not hypermethylated. Hypermethylation can be detected, for example, if an average of 18 or more of the CpG sites in the indicated region of chromosome 19 are methylated. In some embodiments detecting the methylation status of the 20 CpG sites within nucleotides 58,220,424 to 58,220,670 comprises calculating a ratio X: $X=N_{20}/(N_0+N_{20})$, wherein $N_0$ and $N_{20}$ are frequencies of sequence reads in the plurality where 0 or 20 of the 20 CpG sites within the nucleotides 58,220,424 to 58,220,670 of chromosome 19 of the genomic DNA are methylated, respectively. The ratio X is compared to a control to classify the methylation status of the cancer biomarker. In some embodiments detecting the methylation status of the 20 CpG sites within nucleotides 58,220,424 to 58,220,670 comprises calculating a ratio Y: $Y=N_{20}/(N_0+N_1+N_2+N_3+N_4+N_5+N_{20})$, wherein $N_0$, $N_1$, $N_2$, $N_3$, $N_4$, $N_5$, and $N_{20}$, are frequencies of sequence reads in the plurality where 0, 1, 2, 3, 4, 5 or 20 of the 20 CpG sites within nucleotides 58,220,424 to 58,220, 670 of chromosome 19 of the genomic DNA are methylated, respectively. The ratio Y is compared to a control to classify the methylation status of the cancer biomarker. The cytosines of the 20 CpG sites are located at nucleotides 58220424, 58220440, 58220443, 58220446, 58220460, 58220466, 58220479, 58220482, 58220494, 58220500, 58220513, 58220516, 58220535, 58220567, 58220572, 58220595, 58220627, 58220657, 58220662, and 58220669 of chromosome 19. In some embodiments, the biological sample is a plasma or serum sample comprising cell-free DNA. In other embodiments, the biological sample comprises whole blood, serum, plasma, buccal epithelium, saliva, urine, stools, ascites, cervical pap smears, or bronchial aspirates, or a tumor sample. In several embodiment, classification of the methylation status of the cancer biomarker provides an indication of whether or not the biological sample is from an individual with cancer, such as lung cancer, stomach cancer, colon cancer, breast cancer, uterine cancer, bladder, head and neck, kidney, liver, ovarian, pancreas, prostate, or rectum cancer.

III. Computer Implemented Embodiments

The analytic methods described herein can be implemented by use of computer systems. For example, any of the steps described above for evaluating sequence reads to determine methylation status of a CpG site may be performed by means of software components loaded into a computer or other information appliance or digital device. When so enabled, the computer, appliance or device may then perform all or some of the above-described steps to assist the analysis of values associated with the methylation of a one or more CpG sites, or for comparing such associated values. The above features embodied in one or more computer programs may be performed by one or more computers running such programs.

Aspects of the disclosed methods for identifying a subject with cancer can be implemented using computer-based calculations and tools. For example, a methylation status for a CpG site can be assigned by a computer based on an underlying sequence read of an amplicon from a bisulfite amplicon sequencing assay. In another example, a methylation value for a DNA region or portion thereof can be compared by a computer to a threshold value, as described herein. The tools are advantageously provided in the form of computer programs that are executable by a general purpose computer system (for example, as described in the following section) of conventional design.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages. The host computer system advantageously provides an interface via which the user controls operation of the tools.

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages. Any of the methods described herein can be implemented by computer-executable instructions stored in one or more computer-readable storage devices (e.g., memory, magnetic storage, optical storage, or the like). Such instructions can cause a computer to perform the method.

Some embodiments include a computer implemented method comprising receiving a plurality of sequence reads from a bisulfite-amplicon sequencing assay to detect methylation of CpG sites within genomic DNA from a biological sample from an individual. The sequence reads comprise sequences of amplicons produced by amplification of a target nucleic acid sequence comprising nucleotides 58,220,424 to 58,220,670 of chromosome 19 of the genomic DNA. The method includes identifying the methylation status of 20 CpG sites within the nucleotides 58,220,424 to 58,220,670 of chromosome 19 of the genomic DNA from the sequence reads. In several embodiments, the cytosines of the 20 CpG sites are located at nucleotides 58220424, 58220440, 58220443, 58220446, 58220460, 58220466, 58220479, 58220482, 58220494,58220500,58220513,58220516, 58220535,58220567,58220572,58220595,58220627, 58220657, 58220662, and 58220669 of chromosome 19. In some embodiments, software loaded onto the computer system (or accessed through the cloud) can be used to determine nucleotides present in a sequence read in positions where CpG sites are located in the corresponding genomic DNA. The software can assign a methylation status to each CpG site of interest based on the nucleotide present in the sequence read. The software can then provide a classification of the DNA methylation of nucleotides 58,220, 424 to 58,220,670 of chromosome 19 of the genomic DNA based on the identified methylation status of the 20 CpG sites. In a non-limiting example, the methylation of this cancer biomarker can be classified as hypermethylated relative to a control (such as a threshold value).

In several embodiments, classifying DNA methylation of the cancer biomarker based on the identified methylation status of the 20 CpG sites comprises, using a computer, identifying frequencies of sequence reads in a plurality of sequence reads from a bisulfite amplicon sequencing assay where 0 or 20 of the 20 CpG sites within the nucleotides 58,220,424 to 58,220,670 of chromosome 19 of the genomic DNA are methylated CpG sites. The method further include calculating a ratio X:

$$X = N_{20} / (N_0 + N_{20})$$

wherein $N_0$ and $N_{20}$ are the frequencies of sequence reads in the plurality where 0 or 20 of the 20 CpG sites within the nucleotides 58,220,424 to 58,220,670 of chromosome 19 of the genomic DNA are methylated, respectively. If an increase in the ratio X as compared with a control is detected, the cancer biomarker as classified as hypermethylated.

In several embodiments, classifying DNA methylation of the cancer biomarker based on the identified methylation status of the 20 CpG sites comprises, using a computer, identifying frequencies of sequence reads in a plurality of sequence reads from a bisulfite amplicon sequencing assay where 0, 1, 2, 3, 4, 5, or 20 of the 20 CpG sites within the nucleotides 58,220,424 to 58,220,670 of chromosome 19 of the genomic DNA are methylated CpG sites. The method further include calculating a ratio Y:

$$Y = N_{20} / (N_0 + N_1 + N_2 + N_3 + N_4 + N_5 + N_{20})$$

wherein $N_0$, $N_1$, $N_2$, $N_3$, $N_4$, $N_5$, and $N_{20}$, are the frequencies of sequence reads in the plurality where 0, 1, 2, 3, 4, 5 or 20 of the 20 CpG sites within the nucleotides 58,220,424 to 58,220,670 of chromosome 19 of the genomic DNA are methylated, respectively. If an increase in the ratio Y as compared with a control is detected, the cancer biomarker as classified as hypermethylated.

In several embodiments, classifying DNA methylation of the cancer biomarker based on the identified methylation status of the 20 CpG sites comprises, using a computer, identifying frequencies of sequence reads in a plurality of sequence reads from a bisulfite amplicon sequencing assay where 0, 19, or 20 of the 20 CpG sites within the nucleotides 58,220,424 to 58,220,670 of chromosome 19 of the genomic DNA are methylated CpG sites. The method further include calculating a ratio Z:

$$Z = (N_{19} + N_{20}) / (N_0 + N_{19} + N_{20})$$

wherein $N_0$, $N_{19}$, and $N_{20}$, are the frequencies of sequence reads in the plurality where 0, 19, or 20 of the 20 CpG sites within the nucleotides 58,220,424 to 58,220,670 of chromosome 19 of the genomic DNA are methylated, respectively. If an increase in the ratio Z as compared with a control is detected, the cancer biomarker as classified as hypermethylated.

Example Computing System

Figure 24:
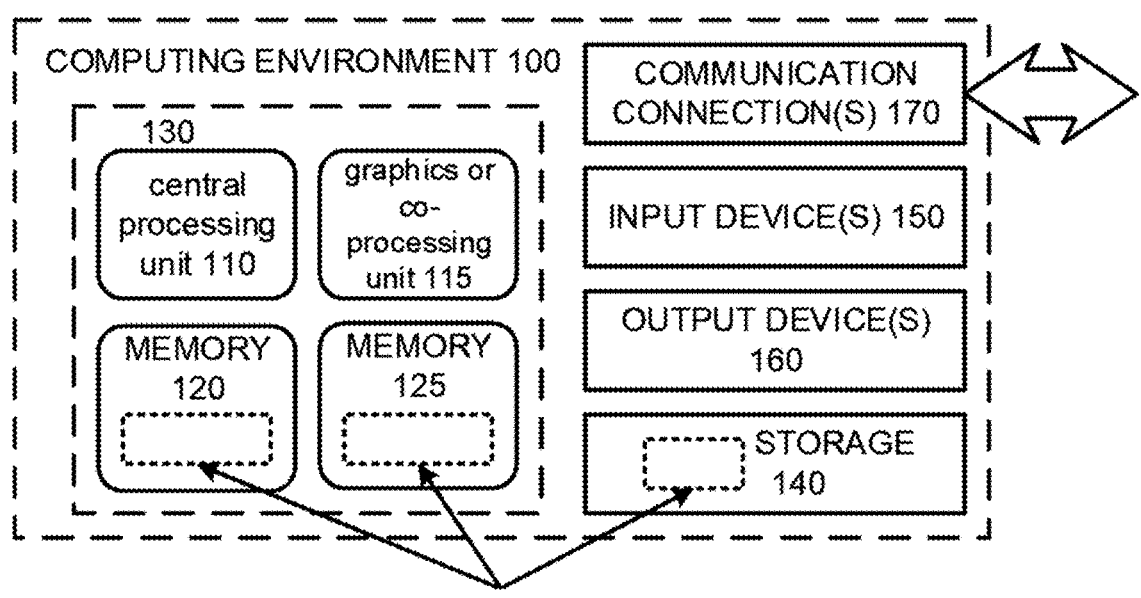
FIG. 24 shows a diagram of an example computing system in which described embodiments can be implemented.

FIG. 24 illustrates a generalized example of a suitable computing system 100 in which several of the described innovations may be implemented. The computing system 100 is not intended to suggest any limitation as to scope of use or functionality, as the innovations may be implemented in diverse computing systems, including special-purpose computing systems. In practice, a computing system can comprise multiple networked instances of the illustrated computing system.

With reference to FIG. 24, the computing system 100 includes one or more processing units 110, 115 and memory 120, 125. In FIG. 24, this basic configuration 130 is included within a dashed line. The processing units 110, 115 execute computer-executable instructions. A processing unit can be a central processing unit (CPU), processor in an application-specific integrated circuit (ASIC), or any other type of processor. In a multi-processing system, multiple processing units execute computer-executable instructions to increase processing power. For example, FIG. 24 shows a central processing unit 110 as well as a graphics processing unit or co-processing unit 115. The tangible memory 120, 125 may be volatile memory (e.g., registers, cache, RAM), non-volatile memory (e.g., ROM, EEPROM, flash memory, etc.), or some combination of the two, accessible by the processing unit(s). The memory 120, 125 stores software 180 implementing one or more innovations described herein, in the form of computer-executable instructions suitable for execution by the processing unit(s).

A computing system may have additional features. For example, the computing system 100 includes storage 140, one or more input devices 150, one or more output devices 160, and one or more communication connections 170. An interconnection mechanism (not shown) such as a bus, controller, or network interconnects the components of the computing system 100. Typically, operating system software (not shown) provides an operating environment for other software executing in the computing system 2600, and coordinates activities of the components of the computing system 100.

The tangible storage 140 may be removable or non-removable, and includes magnetic disks, magnetic tapes or cassettes, CD-ROMs, DVDs, or any other medium which can be used to store information in a non-transitory way and which can be accessed within the computing system 100. The storage 140 stores instructions for the software 180 implementing one or more innovations described herein.

The input device(s) 150 may be a touch input device such as a keyboard, mouse, pen, or trackball, a voice input device, a scanning device, or another device that provides input to the computing system 100. For video encoding, the input device(s) 150 may be a camera, video card, TV tuner card, or similar device that accepts video input in analog or digital form, or a CD-ROM or CD-RW that reads video samples into the computing system 100. The output device(s) 160 may be a display, printer, speaker, CD-writer, or another device that provides output from the computing system 100.

The communication connection(s) 170 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Computer-Readable Media

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing device to perform the method. The technologies described herein can be implemented in a variety of programming languages.

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

IV. Additional Description of Exemplary Embodiments

The present disclosure provides methods for measuring the methylation signal in methods of cancer detection. In one embodiment, bisulfite-amplicon sequencing is employed to detect methylation by relying on the conversion of unmethylated cytosines to uracils upon sodium bisulfite treatment followed by PCR amplification causing uracils to be replaced by thymines and sequencing of the region of interest.

The methods of the present disclosure provide a means to detect a strong, discriminatory hypermethylation signal in solid tumors which is readily reproducible. Further, the methods of the present disclosure are fully applicable to detection of epigenetic cancer biomarkers in circulating tumor DNA with valuable application to clinical diagnostics for cancer detection, particularly early stage cancer detection.

The provided methods further encompass varied combinations of methylated bases within sequenced reads which enable identification of features most optimal to distinguish tumor from normal samples.

In one aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein detection of hypermethylation of the ZNF154 promoter region is indicative of cancer.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein detection of hypermethylation of the ZNF154 promoter region is indicative of cancer, wherein the sample comprises cell-free DNA circulating in the bloodstream of the individual.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein discriminative information for tumor versus normal classification is provided by hypermethylation of about 18 or more CpG sites within the ZNF154 promoter region.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein discriminative information for tumor versus normal classification is provided by hypermethylation of about 16 or more CpG sites within the ZNF154 promoter region.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein discriminative information for tumor versus normal classification is not provided by hypermethylation of about 10 or less CpG sites within the ZNF154 promoter region.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein discriminative information for tumor versus normal classification is not provided by hypermethylation of about 4 or less CpG sites within the ZNF154 promoter region.

In a further aspect, a method is provided for detecting the presence of cancer in an individual, the method comprising:

(a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein the cancer is selected from lung cancer, stomach cancer, colon cancer, breast cancer, uterine cancer, bladder, head and neck, kidney, liver, ovarian, pancreas, prostate, and rectum cancer.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein determining the methylation state of the ZNF154 promoter region in step (D) comprises $X = N_{20}/(N_0 + N_{20})$.

In a further aspect, a method is provided for detecting the presence of cancer in an individual, the method comprising: (a) treating with bisulfite a sample selected from the group consisting of whole blood, serum or plasma, buccal epithelium, saliva, urine, stools, and bronchial aspirates, comprising DNA of the individual; (b) PCR amplifying in said DNA at least a portion of the promoter region of the ZNF154 gene comprising about 20 CpG sites; (c) sequencing the amplified ZNF154 promoter region; and (d) determining the methylation state of the ZNF154 promoter region, wherein determining the methylation state of the ZNF154 promoter region in step (D) comprises $Y = N_{20}/(N_0 + N_1 + N_2 + N_3 + N_4 + N_5 + N_{20})$.

In a further aspect, a computer-implemented method is provided for detecting the presence of cancer in an individual, the method comprising: retrieving on a computer information on the methylation state of the ZNF154 promoter region in a sample of whole blood, plasma or serum from said individual comprising DNA of the individual; performing with the computer a classification of the methylation state of the ZNF154 promoter region; and determining whether said individual has cancer based upon hypermethylation of the ZNF154 promoter region.

In a further aspect, a computer program product is provided for detecting the presence of cancer in an individual, the computer program product comprising: a computer readable medium embodying program code executable by a processor of a computing device or system, the program code comprising: code that retrieves data attributed to a sample of whole blood, plasma or serum from an individual, wherein the data comprises information on the methylation state of the ZNF154 promoter region in said sample; and code that executes a classification method that indicates whether said individual has cancer based upon hypermethylation of the ZNF154 promoter region.

Clause 1. A method for detecting the presence of cancer in an individual, the method comprising:
    (a) treating with bisulfite a sample selected from the group consisting of whole blood, serum or plasma, buccal epithelium, saliva, urine, stools, and bronchial aspirates, comprising DNA of the individual;
    (b) PCR amplifying in said DNA at least a portion of the promoter region of the ZNF154 gene comprising about 20 CpG sites;

(c) sequencing the amplified ZNF154 promoter region; and (d) determining the methylation state of the ZNF154 promoter region, wherein detection of hypermethylation of the ZNF154 promoter region is indicative of cancer.

Clause 2. The method of clause 1, wherein the sample comprises cell-free DNA circulating in the bloodstream of the individual.

Clause 3. The method of clause 1, wherein discriminative information for tumor versus normal classification is provided by hypermethylation of about 18 or more CpG sites within the ZNF154 promoter region.

Clause 4. The method of clause 1, wherein discriminative information for tumor versus normal classification is provided by hypermethylation of about 16 or more CpG sites within the ZNF154 promoter region.

Clause 5. The method of clause 1, wherein the cancer is selected from lung cancer, stomach cancer, colon cancer, breast cancer, uterine cancer, bladder, head and neck, kidney, liver, ovarian, pancreas, prostate, and rectum cancer.

Clause 6. The method of clause 1, wherein determining the methylation state of the ZNF154 promoter region in step (D) comprises $X=N_{20}/(N_0+N_{20})$.

Clause 7. The method of clause 1, wherein determining the methylation state of the ZNF154 promoter region in step (D) comprises $Y=N_{20}/(N_0+N_1+N_2+N_3+N_4+N_5+N_{20})$.

Clause 8. A computer-implemented method for detecting the presence of cancer in an individual, the method comprising:

retrieving on a computer information on the methylation state of the ZNF 154 promoter region in a sample of whole blood, plasma or serum from said individual comprising DNA of the individual; performing with the computer a classification of the methylation state of the ZNF 154 promoter region; and determining whether said individual has cancer based upon hypermethylation of the ZNF 154 promoter region.

Clause 9. A computer program product for detecting the presence of cancer in an individual, the computer program product comprising:

a computer readable medium embodying program code executable by a processor of a computing device or system, the program code comprising:

code that retrieves data attributed to a sample of whole blood, plasma or serum from an individual, wherein the data comprises information on the methylation state of the ZNF 154 promoter region in said sample; and code that executes a classification method that indicates whether said individual has cancer based upon hypermethylation of the ZNF 154 promoter region.

Clause 10. A method for classifying DNA methylation of a cancer biomarker, comprising:

detecting the methylation status of CpG sites within nucleotides 58,220,424 to 58,220,670 of chromosome 19 of genomic DNA from a biological sample from an individual, wherein the genomic DNA has been treated with bisulfite to detect methylation of CpG sites.

Clause 11. The method of clause 10, wherein detecting the methylation status of the CpG sites comprises detecting the methylation status of 20 CpG sites with nucleotides 58,220, 424 to 58,220,670 of chromosome 19 of the genomic DNA Clause 12. The method of clause 10 or clause 11, wherein detecting the methylation of the CpG sites comprises:

amplifying a target nucleic acid molecule comprising the nucleotides 58,220,424 to 58,220,670 of chromosome 19 from the bisulfite-treated genomic DNA to produce amplicons, sequencing the amplicons to produce a plurality of sequence reads; and detecting the methylation status of 20 CpG sites within the nucleotides 58,220,424 to 58,220,670 of chromosome 19 of the genomic DNA based on the plurality of sequence reads.

Clause 13. The method of clause 12, wherein amplifying the target nucleic acid molecule comprises PCR amplification.

Clause 14. The method of clause 12 or clause 13, wherein genomic DNA corresponding to the amplicons comprises or consists the nucleotide sequence set forth as SEQ ID NO: 5.

Clause 15. The method of any of clauses 10-14, comprising comparing the methylation status of the CpG sites within nucleotides 58,220,424 to 58,220,670 of chromosome 19 to a control to determine if the CpG sites are hypermethylated.

Clause 16. The method of clause 15, wherein the hypermethylation of the CpG sites comprises methylation of 18 or more CpG sites.

Clause 17. The method of any of clauses 11-15, wherein detecting the methylation status of the 20 CpG sites comprises:

calculating a ratio X:

$$X = N_{20}/(N_0 + N_{20})$$

wherein $N_0$ and $N_{20}$ are frequencies of sequence reads in the plurality where 0 or 20 of the 20 CpG sites within the nucleotides 58,220,424 to 58,220,670 of chromosome 19 of the genomic DNA are methylated, respectively.

Clause 18. The method of any of clause 11-15, wherein detecting the methylation status of the 20 CpG sites comprises:

calculating a ratio Y:

$$Y = N_{20}/(N_0 + N_1 + N_2 + N_3 + N_4 + N_5 + N_{20})$$

wherein $N_0$, $N_1$, $N_2$, $N_3$, $N_4$, $N_5$, and $N_{20}$, are frequencies of sequence reads in the plurality where 0, 1, 2, 3, 4, 5 or 20 of the 20 CpG sites within nucleotides 58,220,424 to 58,220,670 of chromosome 19 of the genomic DNA are methylated, respectively.

Clause 19. The method of any of clauses 11-18, wherein the cytosines of the 20 CpG sites are located at nucleotides 58220424, 58220440, 58220443, 58220446, 58220460, 58220466, 58220479, 58220482, 58220494, 58220500, 58220513, 58220516, 58220535, 58220567, 58220572, 58220595, 58220627, 58220657, 58220662, and 58220669 of chromosome 19.

Clause 20. The method of any of clauses 11-19, wherein the biological sample comprises whole blood, serum, plasma, buccal epithelium, saliva, urine, stools, ascites, cervical pap smears, or bronchial aspirates.

Clause 21. The method of any of clauses 11-19, wherein the biological sample is a plasma or serum sample comprising cell-free DNA.

Clause 22. The method of any of clauses 11-19, wherein the biological sample is a tumor sample.

Clause 23. The method of any of clauses 15-22, wherein detection of hypermethylation of the CpG sites compared to a control is indicative of the presence of cancer in the individual.

Clause 24. The method of any of clauses 17-23, wherein an increase in the ratio X or the ratio Y as compared with a control is indicative of cancer in the individual.

Clause 25. The method of any of clauses 23-24, wherein the cancer is selected from lung cancer, stomach cancer, colon cancer, breast cancer, uterine cancer, bladder, head and neck, kidney, liver, ovarian, pancreas, prostate, and rectum cancer.

Clause 26. The method of any of clauses 15-258, wherein the control is a threshold value that distinguishes between individuals with and without cancer.

EXAMPLES

The following examples are provided to illustrate particular features of certain embodiments, but the scope of the claims is not limited to those features exemplified.

Example 1

Sample Preparation and Analysis

This example describes the sample preparation and analysis techniques used in Examples 2-6.

GM12878 and K562 cell lines. GM12878 and K562 cell lines were used to extract genomic DNA and do serial dilution for technical and biological replicates. GM12878 is a lymphoblastoid cell line. This cell line has a relatively normal karyotype and low DNA methylation level. Cells were obtained from the Coriell Institute for Medical Research [coriell.org] (Catalog ID GM12878). K562 is an immortalized cell line from chronic myelogenous leukemia (CML) sample. It has high methylation level compared to the normal cell line. K562 cells were obtained from the America Type Culture Collection (ATCC) [atcc.org] (ATCC Number CCL-243).

Sample Preparation for GM12878 and K562 cell lines. Harvesting genomic DNA from GM12878 cells and K562 cells was done in triplicate and genomic DNA from each replicate was serially diluted: 100 ng, 50 ng, and 20 ng. Each dilution was treated with EZ DNA METHYLATION-DIRECT KIT (ZYMO RESEARCH, catalog #D5020 for single sample or D5023 for the plate) for bisulfite conversion, PCR amplified, and sequenced.

Gynecological samples. The Cooperative Human Tissue Network, funded by the National Cancer Institute, provided eight normal endometrial tissue samples. DNA was extracted using the QiaAmp DNA Mini Kit (catalog no. 51304; Qiagen, Hilden, Germany), DNA quality was assessed using the 260:280 ratio measured with a NanoDrop spectrophotometer, and DNA was quantified with a Qubit fluorometer (Invitrogen, Carlsbad, Calif.). Samples consisted of atrophic endometrium obtained from routine hysterectomy or pelvic resection for nonendometrial cancers in postmenopausal individuals. In addition, 42 endometrial tumor samples were obtained from the Cooperative Human Tissue Network. They included 20 endometrioid carcinomas (EECs), 11 serous tumors, and 11 clear cell tumors. Tissues were snap frozen after surgery and stored at −80° C. Genomic DNA was isolated using the Puregene Blood Kit (Qiagen) following the manufacturer's instructions. DNA quality and concentration were assessed using a SmartSpec Plus spectrophotometer (BioRad, Hercules, Calif.).

Lung, Stomach, Colon, and Breast Tumor Panels. Plates containing genomic DNA from tumor and normal samples for each tissue type were purchased from AMSBIO. They extracted genomic DNA from a variety of frozen samples using a modified guanidine thiocyanate technique and dissolved it in 1× TE (10 mM Tris pH=8.0, 1 mM EDTA) Buffer. Each plate had 40 tumor samples and 8 normal samples in technical duplicates. Normal DNAs on the plates were from pathological normal donors i.e. not isolated from normal adjacent tissues from donors with tumors, and so there are no matched samples present on the plates. Each well had 5 µl genomic DNA at about 4 ng/µL, yielding 20 ng (+/−3 ng) of genomic DNA per sample.

Regional view of DNA methylation. Analysis of DNA methylation data from the TCGA Consortium showed that the ZNF154 transcription start site (TSS) exhibits baseline methylation in normal tissues compared to hypermethylation in 15 different solid epithelial tumor types. While the data examined all available probe sites from the ILLUMINA 450K INFINIUM methylation array across the genome, the sparsity of distributed ILLUMINA methylation probes across this locus prohibited analysis of the breadth of the hypermethylated region (HMR). It was only possible to estimate that the HMR was between ~750 bp and 11,700 bp long. This question was addressed by assessing whole genome bisulfite sequencing (WGBS) studies. For example, data published in the Gene Expression Omnibus, GSE46644 for individual matched tumor and normal colorectal samples display a 1.5-2 kb region of hypermethylation in the tumor sample, in which the ZNF154 TSS is centrally located (FIG. 1(A)), and other samples show a similar HMR.

Figures 1B, 1C:
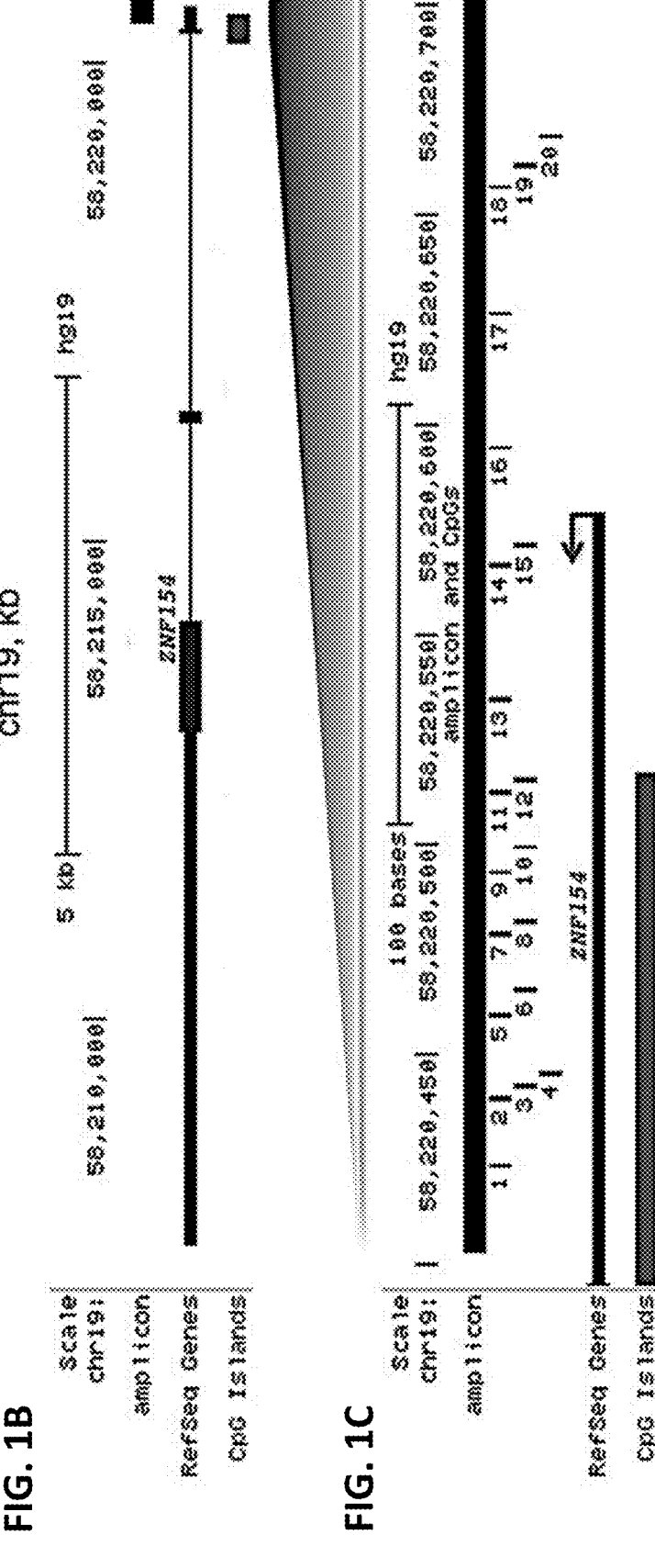

Based on these data, a PCR amplicon region was designed to cover part of the HMR of the ZNF154 locus identified, including the TSS and a part of the associated CpG island (FIGS. 1(B)-(C)). Additionally the amplicon is positioned centrally in the region of tumor-specific hypermethylation, which should be optimal for the purposes of distinguishing tumor from normal samples.

Human Methylation Array. Gynecologic samples were analyzed with the HumanMethylation Illumina BeadChip. The hybridization reaction was performed according to the manufacturer protocol, and samples were scanned using the Illumina iScan System.

Amplicon Generation. To generate a 302-bp PCR product from ZNF154, we used forward (5'-GGTTTTTATTT-TAGGTTTGA-3'; SEQ ID NO: 1) and reverse (5'-AAATC-TATAAAAACTACATTACCTAAAATACTCTA-3'; SEQ ID NO: 2) primers. The primers contained different adapters at their 5' ends: forward adapter: 5'-ACACTCTTTCCCTA-CACGACGCTCTTCCGATCT-3' (SEQ ID NO: 3), reverse adapter: 5'-GTGACTGGAGTTCA-GACGTGTGCTCTTCCGATCT-3' (SEQ ID NO: 4). A shorter primer can be used in place of SEQ ID NO: 2, having a sequence: (5'-ACTACATTACCTAAAATACT-3'; SEQ ID NO: 6) The primer design assumed all non-CpG Cs are converted with sodium bisulfite to Ts. The primers annealed to regions in the genomic DNA sequence devoid of any cytosines in a CpG context. PCR reactions contained 0.25 µL of 5-U/µL TaKaRa EpiTaq HS DNA Polymerase (for bisulfite-treated DNA) with 10× EpiTaq PCR Buffer, 5 µL of 25 mmol/L MgCl2, 6 µL of 2.5 mmol/L dNTP mix (catalog no. R110A; TaKaRa Bio Inc., Kusatsu, Japan), and 1 µL each primer at 12.5 µmol/L in 50-µL total volume. Cycling conditions were 95° C. for 10 minutes, 45 cycles of 95° C. for 30 seconds, 48° C. for 30 seconds, and 72° C. for 60 seconds, and 72° C. for a 7-minute final extension. PCR products were verified by electrophoresis on a 2% agarose gel.

After PCR, one or two rounds of product cleanup were performed by adding 37.5 μL of Agencourt Ampure XP PCR Purification Beads [catalog no. A63881; Beckman Coulter Genomics (formerly Agencourt), Danvers, Mass.] to the 50-μL PCR mixture. PCR products were verified by electrophoresis on a 2% agarose gel. Following cleanup, barcodes (Illumina Amplicon Indexing Oligos) were added in a second round of PCR, using 25 μL of 2× Phusion Master Mix (catalog no. M0531L; New England Biolabs Inc., Ipswich, Mass.) and 1 μL each bar-coded primer at 25 μmol/L in 50-μL total volume. Cycling conditions were 98° C. for 30 seconds, 8 cycles of 98° C. for 10 seconds, 65° C. for 30 seconds, and 72° C. for 30 seconds, and 72° C. for a 5-minute final extension. A final round of XP PCR purification bead cleanup was applied, as before, to remove excess bar-coding oligonucleotides.

Amplicon Sequencing. PCR products were sequenced at the NIH Intramural Sequencing Center using the Illumina MiSeq platform with reagent kit version 3 (Illumina Inc.) to generate paired-end, 300-bp reads (200 bp for the lung plate). Briefly, agarose gel analysis was performed for each well in the 96-well amplicon plate. On the basis of the intensity of the product bands, the relative concentration of each sample was estimated. Using these values, a pool was created that adjusted for relative differences. The concentration of this pool was determined using the Illumina/ Universal Library Quantification Kit (Kapa Biosystems Inc., Wilmington, Mass.). An aliquot of the pool was run on a MiSeq (Illumina Inc.) using a MiSeq Reagent Nano kit version 3. This quality control run consisted of 25 cycles followed by a 6-cycle index read, which provided an accurate profile of the representation of the samples in the pool. If necessary, an additional volume of poorly represented amplicons was added to the pool. The final pool was then sequenced on the MiSeq. Both MiSeq runs were spiked with a PhiX control library to improve base diversity. The PhiX library typically accounted for 30% to 50% of reads. Postrun processing of data were performed using RTA version 1.18.42 and CASAVA software version 1.8.2 (Illumina Inc.).

Presentation of Changes in Methylation. Methylation levels are reported in percentages or fractions (percentage per 100). To avoid possible confusion, when a methylation difference of X % is noted, we refer to an absolute difference of X units (0 to 100), not a relative X % change from the current methylation level. For example, if the reference methylation level is 30%, then a 10% difference from the reference level indicates 20% or 40% methylation, not 27% or 33%.

Alignment of Sequencing Data. Samples were sequenced on the ILLUMINA MISEQ platform. All sample plates except lung were run in 300PE mode (300 bp paired-end reads). The lung plate was run in 200PE mode. It was observed that the base quality deteriorates substantially in the second half of the paired-end sequence reads, especially the second reads. Therefore, because the reads were expected to overlap, the first 200 bp from the first read and the first 102 bp from the second read (after reverse-complementing them) were adjoined to produce single fragments of the expected 302-bp length.

The resulting full-length fragments were aligned to the human genome version GRCh37/hg19 using Bismark version 0.7.12. This procedure filtered out nonaligning reads and returned the number of aligned reads and methylation levels at each C, including each of the 20 CpGs in the amplicon and cytosines in non-CpG contexts, and mean methylation across each sample in CpG, CHG, and CHH contexts (where H represents A, C, or T). Non-CpG methylation was used as an internal upper-bound estimate of the inefficiency of bisulfite conversion because little appreciable cytosine methylation occurs outside CpG dinucleotides. Moreover, the alignment files contained the patterns of methylated bases within individual sequence reads.

The mapping efficiency (ie, the percentage of reads aligned to the genome out of total sequenced reads) varied from 0% to 89% (median, 18%) across sample replicates. Most, if not all, of the unaligned reads show clear primer dimer signatures, such as repeated forward and/or reverse primer and adaptor sequences, and typical poly-A artifactual base calls extending beyond the actual fragment size. These fragments were the most likely cause of the additional lower bands observed on our agarose gels; however, genomic alignment effectively filters them from the analysis.

The fraction of cytosine nonconversion in non-CpG contexts calculated by the Bismark application is, in fact, an underestimate because it takes into account the cytosines in the primer regions, which are expected to be always converted due to primer design (the primers hybridize only to Cs that are converted to uracil). To directly estimate nonconversion percentages in the aligned reads, the Cs were examined in a CHG and CHH context. The 302-bp ZNF154 amplicon contains 14 Cs in a CHG context (two within each of the primer regions and 10 between) and 59 Cs in a CHH context (six and four within the forward and reverse primers, respectively, and 49 between). Therefore, Bismark estimates were corrected by factors of 14/10=1.40 and 59/49=1.20 for CHG and CHH contexts, respectively. Indeed, when nonconversion percentages in the aligned reads were directly analyzed, excluding cytosines within primer regions, the slopes in linear regressions of our direct estimates versus Bismark estimates closely agreed with these factors: 1.35 and 1.22 for CHG and CHH contexts, respectively.

The nonconversion percentage in non-CpG context was used as an upper limit of the inefficiency of sodium bisulfite treatment. Assuming a similar effect at all cytosines, the reported CpG methylation levels can be corrected. In this way, a true percentage of methylation CpG was calculated as $mt=100 (mo-e)/(100-e)$, where mo is the observed percentage of mCpG, and e is the nonconversion percentage of unmethylated cytosines. Hence, the difference between the observed and true levels is $mo-mt=(100-mo) e/(100-e)$.

Taking the maximum of the four estimates of non-CpG methylation/nonconversion for each sample as e (ie, two direct estimates for CHG and CHH contexts, as described above, and two estimates from Bismark), the median correction in percentage of mCpG, or the median of mo–mt, was 0.4, and the maximum was 2.8 (on a scale of 0 to 100). Given such a small effect, the uncorrected values were kept.

Sample Reproducibility. Comparison of sample duplicates in the four 96-well tumor plates revealed that duplicates with >1000 aligned reads closely agreed, in accord with recent reports. However, two outlier samples on the colon plate had duplicate methylation signals of 60% and 20% (with >1000 aligned reads in each duplicate), indicating that duplicates from the two samples had been inadvertently swapped. These samples were removed from the analysis. To maximize the number of samples retained for further analysis, reads from both duplicates were summed for each sample. A sample was retained if there were >1000 aligned reads in total unless the following two conditions occurred: each duplicate had >250 aligned reads, and mean CpG methylation differed by >0.2 (20%) between duplicates. The last condition excluded the two suspicious colon samples (but nothing else).

Analysis of clinical data. Most of the post-alignment analysis was done using R language for statistical computing (version 3.1.1). ANOVA was used (R functions 'lm' and 'anova') to regress average sample methylation on age, gender and tumor diagnostic (subtype and differentiation level/grade) as provided with the four sample plates. Both full and shortened diagnostics versions were used—shortened versions excluded tumor differentiation levels (not available for stomach) and produced fewer, but larger, categories. Single term deletions were used in the model (R function 'drop1') to estimate significance of predictors (there are no interaction terms in the model).

Extraction of Sequencing Read Methylation Patterns. Most aligned reads (approximately 99.5%) had the expected starting coordinate (chr19:58220404); most of the rest aligned to neighboring bases, with several single-occurrence exceptions. Only reads with 20 CpGs (based on Bismark context calls) that were aligned to the expected starting coordinate were retained, yielding 93% to 98% (median, 96%) of the aligned reads reported by Bismark application. This finding is consistent with a Phred base quality score of approximately 30 (ie, a base call error rate of 0.001). The 20 CpGs translate to 40 bases that can be miscalled, which occur at rates of approximately 0.04, or 4%, of aligned reads. Comparing mean sample methylation between the values reported by Bismark and those based only on the reads we retained, the maximal absolute difference was negligible, 0.6% or 0.006 (the median absolute difference was only 0.13%).

Hierarchical Clustering of Samples Based on the Most Abundant Patterns. The 1000 most frequent methylation patterns in each sample were kept, with their union yielding 57,926 distinct patterns. The union of the 30 most abundant patterns in normal and 30 most abundant patterns in tumor samples yielded 45 distinct patterns that were used in hierarchical clustering. Selection of the most abundant patterns was based on ranking the means of the pattern fractions across tumor and normal tissue samples. On average, at least twice as many single-C read patterns were observed in normal samples than were expected from our estimates of inefficient sodium bisulfite conversion of fully unmethylated reads (P<10$^6$, Wilcoxon signed-rank test), arguing that the single-C patterns are likely to be real events and not artifacts of incomplete conversion.

The fractions of these 45 patterns across 218 samples were log-transformed after replacing any fractions with a value of zero with values represented by one-tenth the minimal nonzero value for that pattern across all samples. To perform hierarchical clustering, we used the R functions heatmap.2 (package gplots) and hclust (package stats) with the ward.D2 agglomerative clustering method and Euclidean distance. Because the data were log-transformed, distance was based on fold changes in pattern fractions.

Calculation of Read Fractions with k Methylated CpGs. As stated previously, only sequence reads with 20 CpGs (based on Bismark context calls) that aligned to the starting coordinate chr19:58220404 were retained. In each sample, sequence reads with equal numbers of methylated CpGs (0 to 20; ie, values of k), were counted together in the read fractions ($n_k$). The sum of all $n_k$ was normalized to 1. Using the set of $n_k$, the following ratios were defined:

$$x = N_{20}/(N_0 + N_{20}), \tag{1}$$

$$y = N_{20}/(N_0 + N_1 + N_2 + N_3 + N_4 + N_5 + N_{20}), \text{ and} \tag{2}$$

$$z = (N_{19} + N_{20})/(N_0 + N_{19} + N_{20}). \tag{3}$$

Note that the mean mCpG fraction per sample can be calculated as follows:

$$m = \left(\sum\nolimits_{k=0}^{20} kn_k\right)\bigg/\left(20\sum\nolimits_{k=0}^{20} n_k\right). \tag{4}$$

ROC Curve Classification. The R package pROC was to calculate area under the receiver operating characteristic (ROC) curve (AUC) CIs (using the default deLong method). The R package ROCR was for convex hull calculation. The P value for the AUC was obtained from a Wilcoxon rank sum test evaluating the hypothesis that the distribution of the ranks in the two groups (normal tissue and tumor samples) is equal (if this hypothesis is correct, the AUC should be 0.5).

Dilution simulations. For each tumor $T_i$ out of the 184 samples, one of the 34 normal samples was randomly matched, $N_j$, and the signals were mixed together at a chosen fraction f yielding an in silico diluted tumor $D_{ij}=(1-f)*T+f*N_j$. Each $T_i$ was randomly matched with one of the normals 100 times, resulting in a set of 18,400 diluted tumors. The fact that same matches can occur multiple times does not affect the ROC analysis. All $T_i$'s and $N_j$'s were represented as vectors containing (normalized) frequencies $\{n_k\}$ of aligned reads with given numbers of methylated CpGs, with k between 0 and 20, as well as methylation levels at each of the 20 CpGs. The fraction f of normals in the mixture went from 0.1 to 0.99 through 0.2, 0.3, 0.4, 0.5, 0.6, 0.7, 0.8, 0.9, 0.925, 0.95 and 0.975. In the ROC analysis, each dilution level (each f) was analyzed in isolation from other levels.

Machine learning classifications. We applied k-nearest neighbors (KNN) and support vector machine (SVM) algorithms, using the three alternative sample representations: i) methylation values at each of the 20 individual CpGs, ii) the 45 most recurrent pattern frequencies, and iii) frequencies of groups of patterns $n_k$ with k methylated CpGs ($0 \leq k \leq 20$). For our computationally diluted data sets we used only the first and third representations.

Each representation was either used as is or log-transformed. To avoid infinities due to log(0) in the latter case, three alternative thresholds were tried: e={1e-5, 1e-3, 0.1} and the data was transformed as log(data+e). k nearest neighbors (KNN) and support vector machine (SVM) algorithms were used. For KNN implementation 'knn.cv' function from R package 'class' with 1, 3, 5, 7 or 9 nearest neighbors was used; even numbers were omitted to avoid randomly resolved draws. For SVM 'svm' function from R package 'e1071' was used and wrote a wrapper code to perform the leave-one-out cross-validation. The svm parameter class.weights was set to be inversely proportional to the class sizes used in training, with mean set to 1, and used five alternative cost values 0.1, 1, 10, 100 or 1000. Other parameters had default values, for example radial kernel was used.

Example 2

Validation of Reproducibility for Bisulfite Amplicon Sequencing Using Cell Line DNA The harsh conditions imposed by bisulfite treatment fragment and damage DNA molecules. It was therefore sought to assess the technical variability of DNA methylation in PCR amplification products potentially affected by a limited sampling of variability among DNA molecules at very low concentration levels.

For this analysis, three dilutions of genomic DNA each from K562 and GM12878 cell lines were sampled at 20 ng, 50 ng, and 100 ng in duplicate from three replicate culture flasks, thus yielding 18 samples per cell line Amplicon products for each sample were generated, barcodes added and sequenced on the ILLUMINA MISEQ platform. The analysis consisted of aligning sequence reads to a converted genomic reference sequence at the target locus (hg19, chr19: 58220404-58220705) using Bismark. For GM12878, 16 out of 18 samples yielded aligned reads, between 1,276 to 120,500 reads at the amplicon locus with a median of 23,460. For K562, 11 out of 18 samples yielded aligned reads, with 1,796 to 237,900 reads per sample and a median number of 26,480.

Figures 2A, 2B:
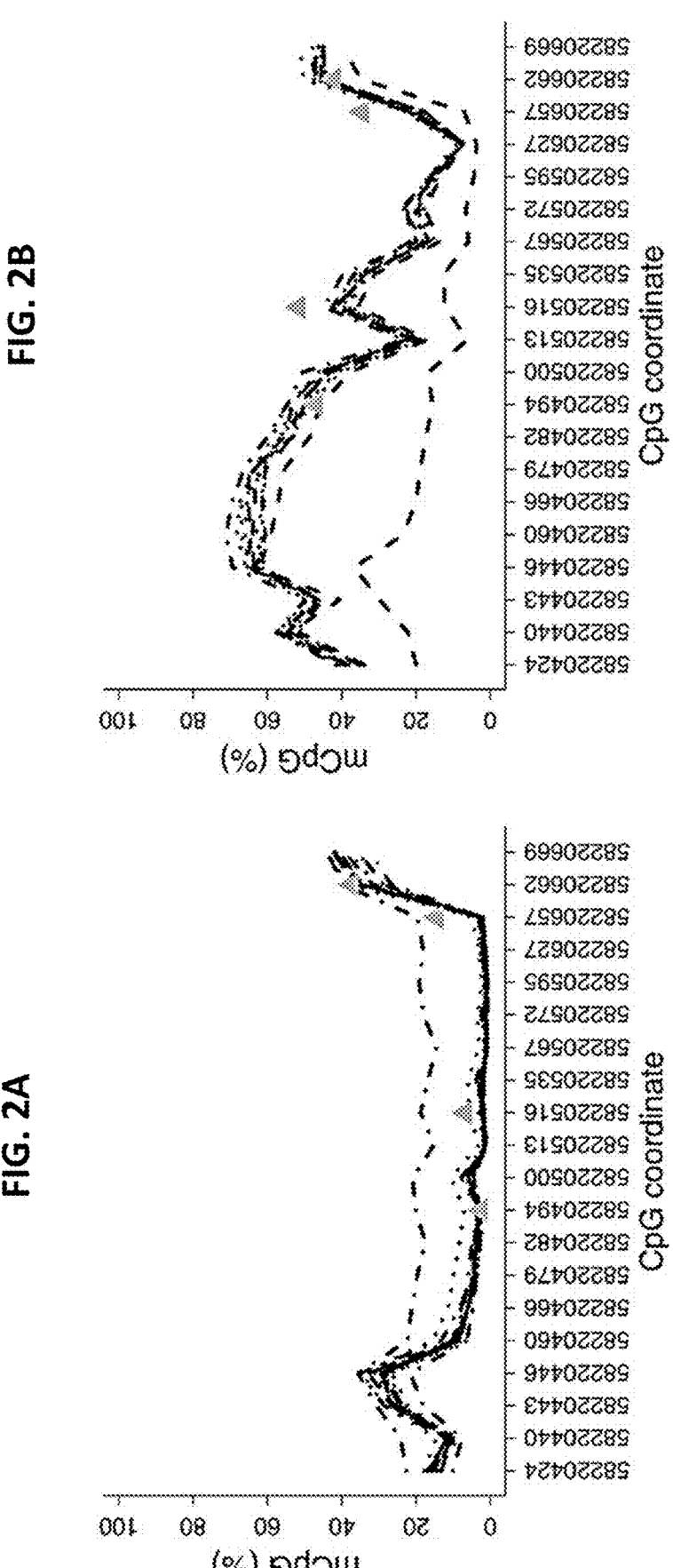
FIGS. 2A and 2B show a set of graphs illustrating the Reproducibility data of amplicon sequencing products from bisulfite-converted cell line DNA. Results are shown for GM12878 (A) and K562 (B) cell lines. Each line represents a different replicate. Gray triangles represent the percentage of CpG methylation (mCpG) at four CpG positions present on the Illumina methylation array data, generated from the same cell types by ENCODE.

The sequencing data across replicates from different starting DNA concentrations show robust methylation signals with minimal variation, both for K562 and GM12878 cell lines (FIGS. 2(A)-(B)). The consensus in the profiles representing methylation levels at each CpG is obvious from an overlap of 15 of the 16 GM12878 replicates and 10 of the 11 K562 replicates. Notably, for each cell line, one replicate falls out of the consensus profile. Excluding these outlier samples, the average percent CpG methylation level (% mCpG) for K562 cells is 40.7% compared to 10.1% for GM128708. The standard deviation in measuring the % mCpG at each of the 20 CpG dinucleotides is small, ranging from 0.5% to 3.4% for GM12878 and 0.6% to 3.8% for K562. Moreover, the methylation trends are similar to the ILLUMINA array methylation data generated by the ENCODE Consortium for K562 and GM12878 cell lines at four probes in this same region (FIGS. 2(A)-(B)).

The data show that from a biological standpoint, methylation at ZNF154 discriminates a tumor-derived cell line, K562, from a nontumor cell line, GM12878, which is derived from transformation of phenotypically normal human lymphoblasts (p=2e-5, Wilcoxon test, even including the outliers). Utilizing as little as 20 ng of genomic DNA, bisulfite amplicon sequencing produced reproducible data with minimal deviation, (~2%) in methylation signal between technical replicates. However, significant deviations are possible when outliers occur, advocating for the use of technical replicates.

Example 3

Bisulfite Amplicon Sequencing in Solid Tumor Gynecological Samples

Bisulfite amplicon sequencing was used to investigate methylation levels at the ZNF154 locus in genomic DNA extracted from 2 endometrial normal samples and 41 endometrial solid tumors comprising a collection of 19 endometroid tumors, 11 serous tumors and 11 clear-cell tumors.

Figure 10:
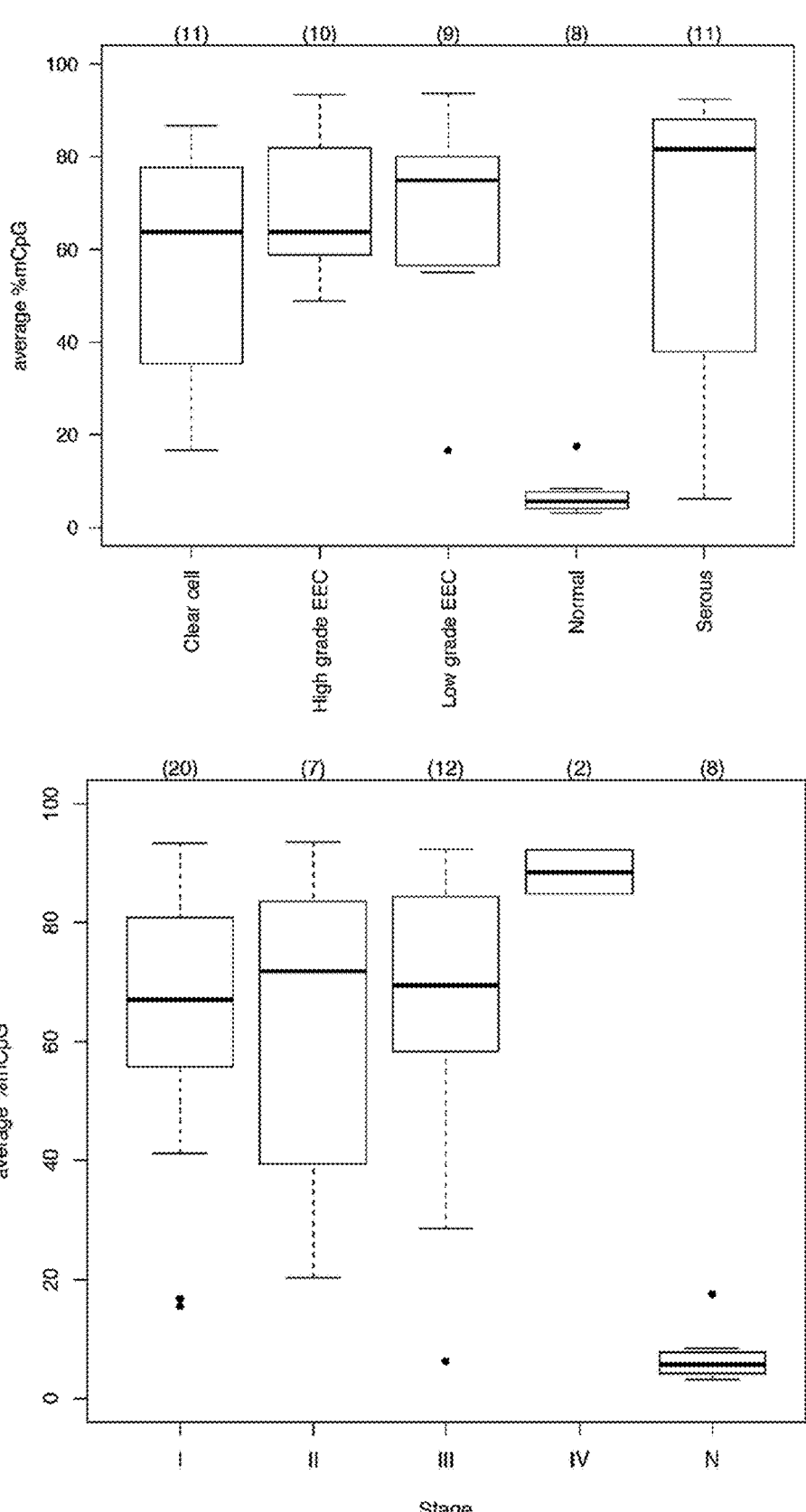
FIG. 10 shows a set of graphs illustrating the distribution of mean methylation levels in endometrial tumor and normal tissue samples, stratified by tumor subtype (top panel) or stage (bottom panel). The number of samples in each category is shown above the box plots.

Each sample was assessed in a single copy and only those with 1000 aligned reads were considered (excluding one low-grade EEC sample with 402 aligned reads). Averaging signal across the amplicon, tumors display a 66% increase in median methylation levels relative to normal tissue (P=2× 10⁻⁵, Wilcoxon rank sum test, FIG. 3A). All tumor stages were hypermethylated relative to normal tissue (P≤0.01, t-test). Stage IV tumors (one serous and one clear cell sample) were hypermethylated relative to each of the lower stages (P≤0.05, t-test) (FIG. 10); however, no significant methylation differences were observed among endometrioid, serous, and clear cell tumor subtypes at this locus.

Figure 3C:
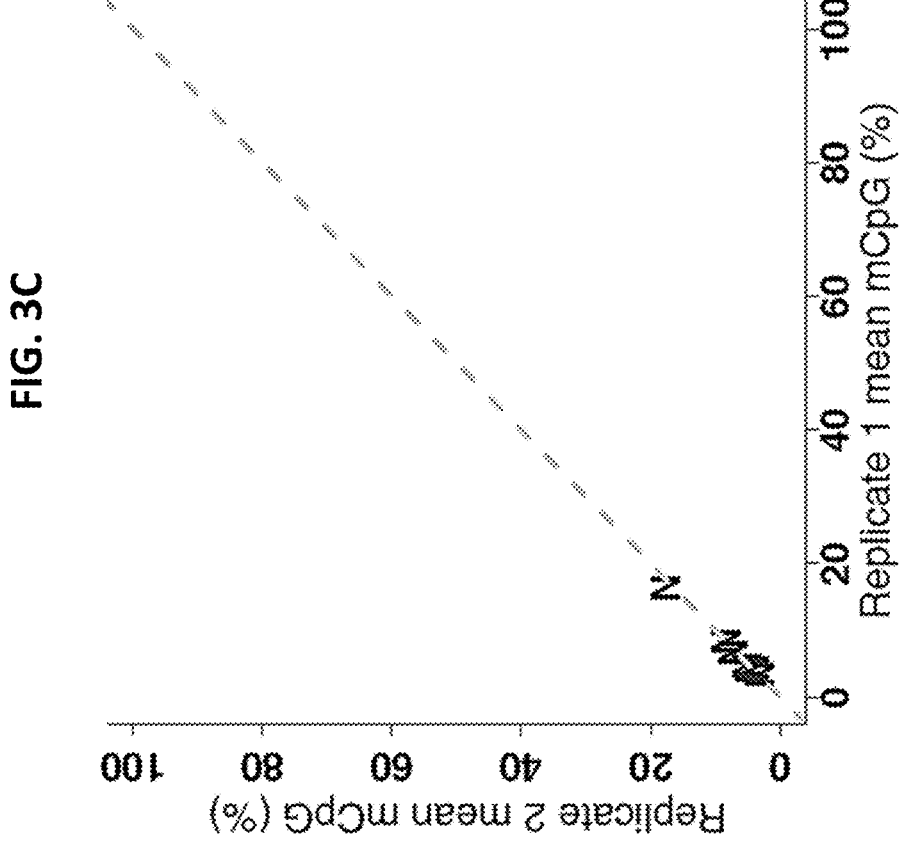
Figure 11:
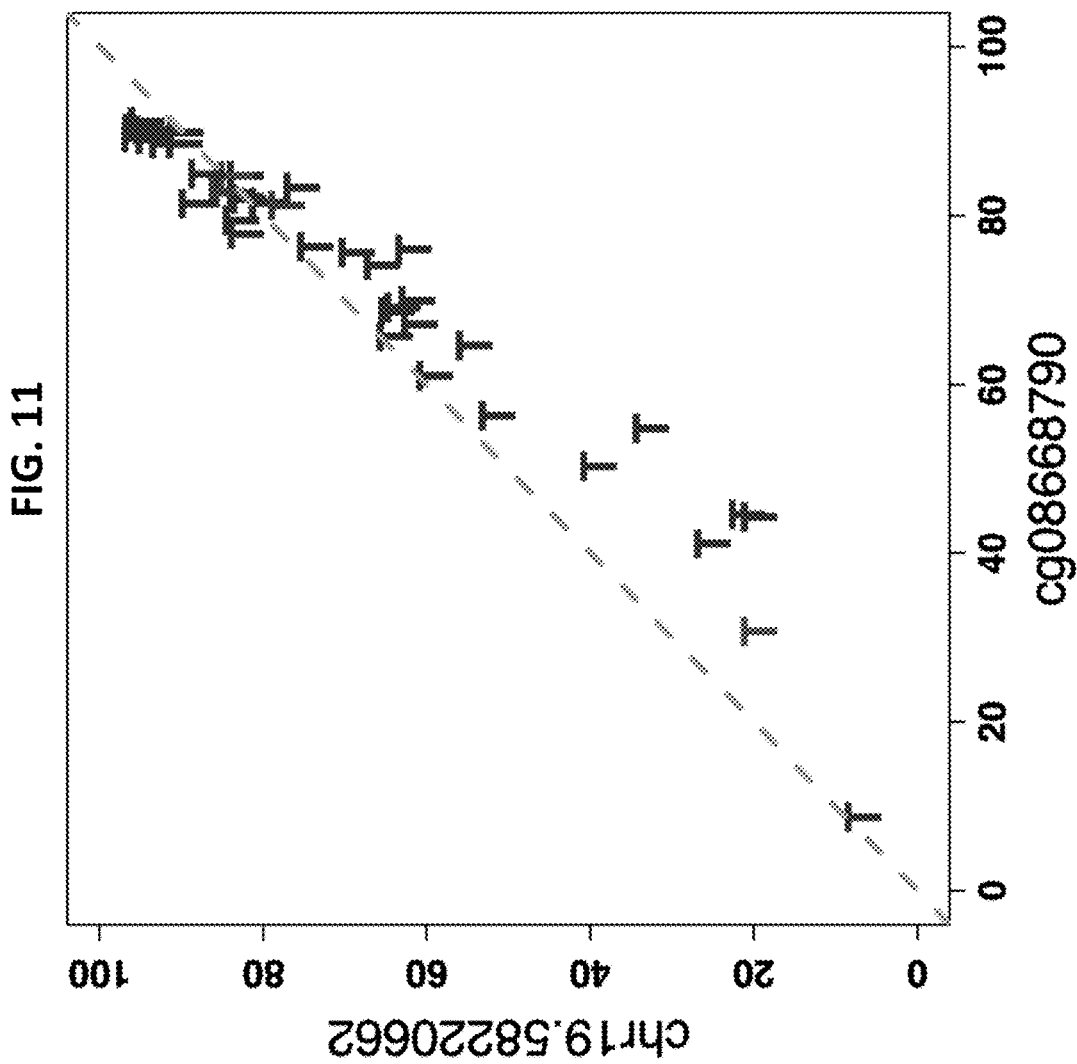
FIG. 11 shows a scatterplot of tumor (T) methylation levels measured with Illumina methylation arrays at probe cg08668790 (x axis) versus amplicon sequencing at the corresponding genomic position, chr19:58220662 (y axis).
Figures 12A, 12B:
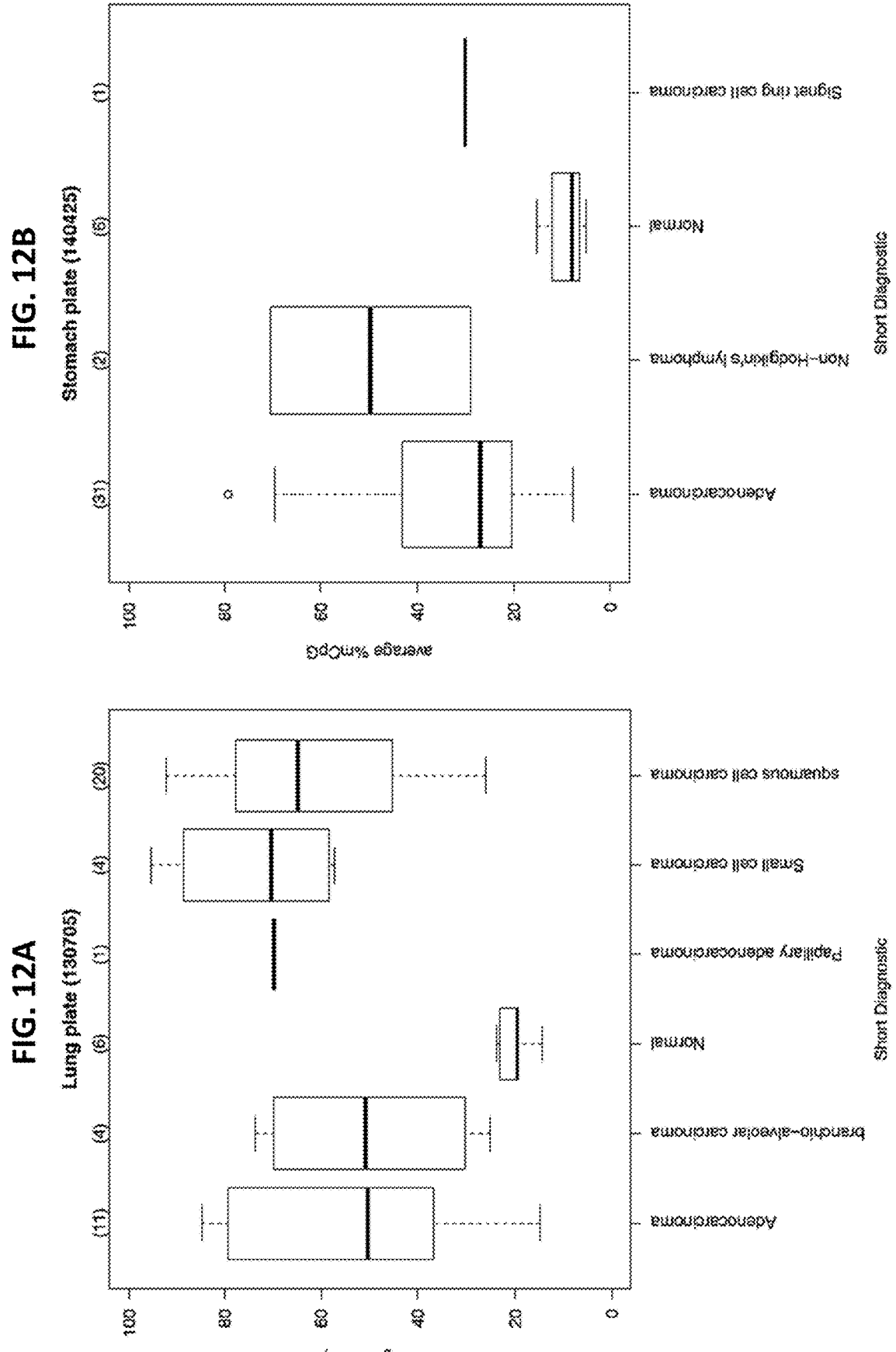

Comparison of ILLUMINA methylation array data and bisulfite sequencing data of the same samples at the two available probes overlapping the amplicon shows consistency (Pearson correlation coefficients 0.95 and 0.96, mean differences only 5.2% and 3.7%) (FIG. 3B and FIG. 11). The agreement between the sequencing and the array methylation values was strongest at very high methylation levels and more variable at lower methylation levels. An advantage of amplicon sequencing compared to INFINIUM arrays is an ability to assess bisulfite conversion of unmethylated cytosines within the amplicon, which create a false positive signal for methylation when conversion is incomplete. For these samples, all Cs in non-CpG contexts were examined within the sequencing data and showed minimal non-conversion (between 0.3% and 6.4% per sample, with a median of 2.6%).

Through the use of bisulfite amplicon sequencing several characteristics about the data not accessible from methylation array data were observed. For example, a slight drop occurs in median methylation in both normals and tumors across four CpGs that surround the ZNF154 TSS (chr19: 58220579) (FIG. 3A), suggesting the position is more resistant to DNA methylation than surrounding regions. Also, the variability in percent methylation is greater at each CpG position in tumors than normals. Although low variance in normal samples is expected due to lowered heterogeneity compared to tumor samples, the small number of normal samples may also contribute to this difference. It was also shown that some tumors carry methylation below that observed for normal samples, which is consistent with reports from TCGA showing that some tumors lack DNA hypermethylation profiles. Taken together, these data confirm that methylation levels at this amplicon separate the majority of the uterine tumor samples from normal samples.

Example 4

Methylation Measurements in Lung, Stomach, Colon and Breast Tumors and Normal DNA methylation patterns were assessed in a larger set of tumor samples of non-gynecological origin. These tumor panels covered a larger sample size of 40 tumors and 8 normals each and represented four different tumor types: lung, stomach, colon, and breast. All samples were examined in duplicate to estimate the measurement accuracy. Samples were used that had more than 1000 aligned sequenced reads, resulting in informative sample sizes of 46 for lung cancer (40 tumor and six normal tissue samples), 40 for stomach cancer (34 tumor and six normal tissue samples), 36 for colon cancer (30 tumor and six normal tissue samples), and 47 for breast cancer (39 tumor and eight normal tissue samples).

Figures 4A, 4B:
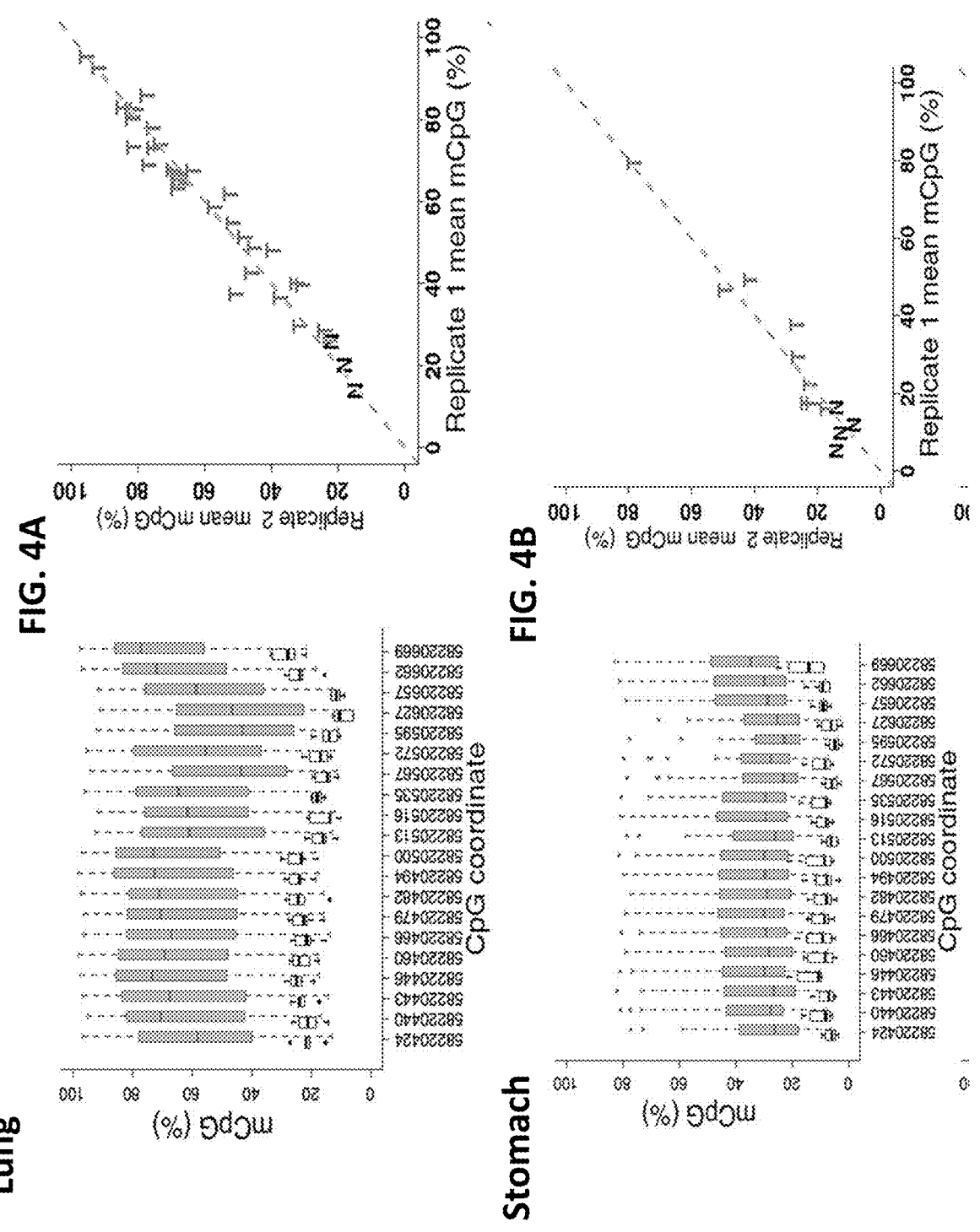

In each of these cases the average methylation within the amplicon region was greater in tumors than normals. The median percent methylation (% mCpG) was 20%, 8%, 19% and 4% in the normal tissues of lung, stomach, colon and breast, respectively. In stomach and breast tumors, a 20% and 31% increase was found, respectively, in the median methylation in tumors relative to normals (p=3.0e-4, p=2.1e-4, Wilcoxon test) (FIG. 4A). Colon and lung tissue showed greater increases of 44% and 45%, respectively, (p=3.9e-4, p=4.1e-6, Wilcoxon test). Thus the four tumor types consistently showed significant hypermethylation compared to normal samples at this locus. Consistent measurements between duplicates having more than 1000 aligned reads (FIG. 4B) were found, including a strong correlation between replicates for lung, stomach, and breast (Pearson correlation coefficients ≥0.966). In the colon plate, removal of two pairs of outlier duplicates rendered the Pearson correlation coefficient at 0.966. Each replicate in these pairs had a methylation signal, of 60% and 20%, suggesting an inadvertent swap occurred among these two samples and highlighting the importance of replicate samples.

The median methylation around the ZNF154 TSS (chr19: 58220579) showed a divot, whereas higher methylation levels existed in the CpG island to the left and its south shore to the right. Greater variance in tumor samples relative to normal samples was also recorded. Moreover, as seen previously, all four tumor types have a subset of samples with methylation levels comparable to, or even below that observed for the normal, consistent with model of tumors that do not show aberrant DNA methylation reported by TCGA studies. A quality control assessment of the samples was also performed and it was concluded that non-conversion rates of cytosines to thymines in all non-CpG contexts were extremely low indicating a low false methylation rate generated by bisulfite nonconversion events (between 0.2% and 1.2%, all medians ≤0.6%).

Figures 13A, 13B, 13C:
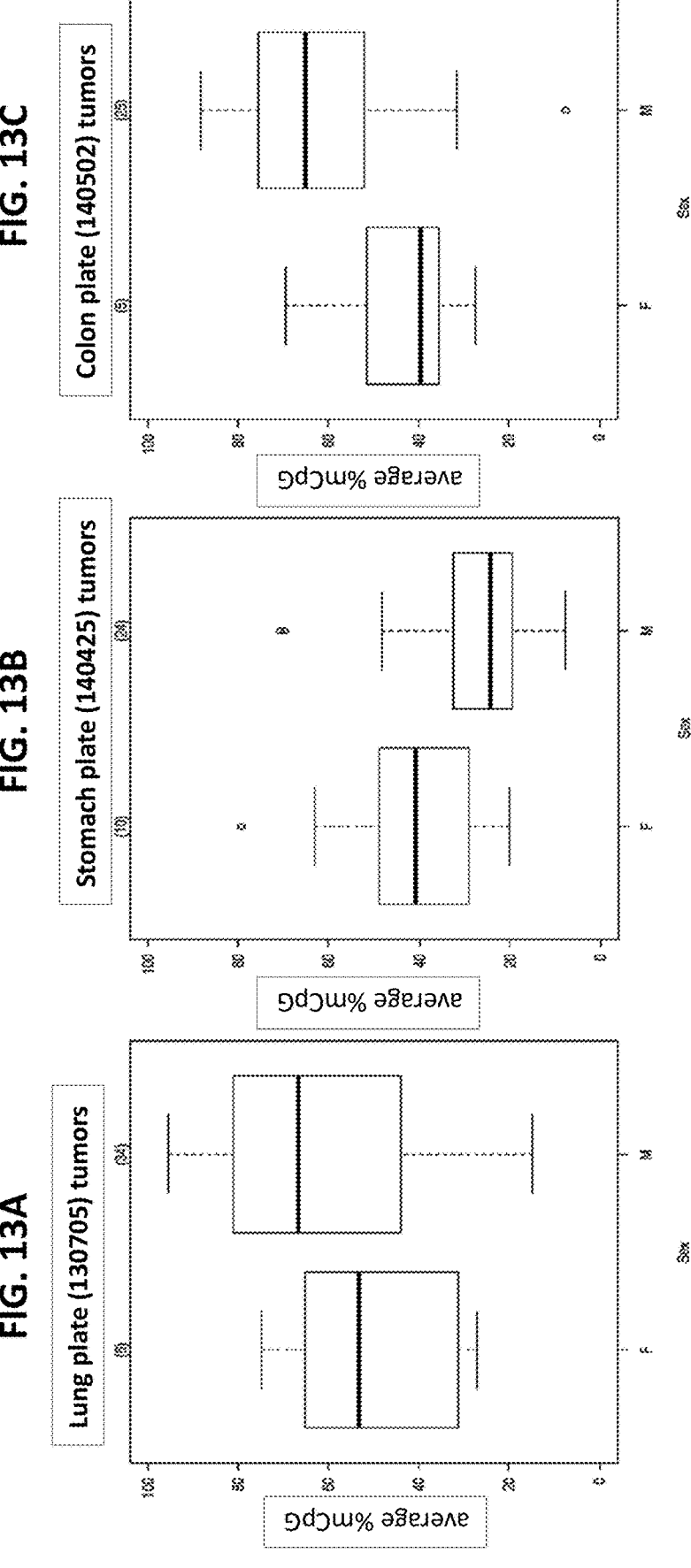
FIGS. 13A-13C show a set of graphs illustrating the distribution of mean methylation levels in lung, stomach, and colon tumors as a function of sex (female or male). The number of samples in each category is shown above the box plots.

Each tumor panel in the analysis provided tumor subtype and relative grade (differentiation level) information, as well as patient age and gender. Using a linear regression model it was assessed whether average sample methylation level was predicted as a function of subtype (with or without grade), age and gender. All tumor types showed hypermethylation compared to normals (P<0.05; (FIGS. 12(A)-(D)), however no statistically significant differences appeared between tumor subtypes on each plate, after correcting for age and gender. In contrast, gender showed a correlation with methylation levels in stomach and colon tumors, with marginally significant p-values (0.055 for stomach and 0.051/0.016 for colon, using subtype and grade/subtype) (FIG. 13(A)-(C)). While the samples sizes were quite small, between subtypes and stages, some differences were found in median methylation levels. For example, of four subtypes of lung tumors: adenocarcinoma, branchio-alveolar carcinoma, small cell carcinoma, and squamous cell carcinoma, the small cell carcinomas and squamous cell carcinomas showed 15% greater median methylation than the others. Moreover, 25% greater median methylation was found in colon and lung adenocarcinomas relative to stomach adenocarcinomas.

Adenocarcinomas represented a large proportion of the subtypes in the endometrial (41/41), lung (11/40), stomach (31/34), colon (30/30), and breast (39/39) tumors. This is not surprising because adenocarcinoma is the most commonly diagnosed tumor subtype for each of these tissues. When analyzing only adenocarcinomas, tumors had a mean of 30% hypermethylation in the lung and colon tumors relative to normal tissue and >20% in breast and stomach tumors relative to normal. In lung tissue, squamous cell and small cell carcinomas are associated with a history of tobacco use and are considered aggressive tumors; they found even higher median methylation levels in our data set. Breast tumors in our study were predominantly represented by invasive ductal carcinomas (33/39), which have a median methylation level of 34% compared with just 4% in normal breast tissue.

Thus, it is shown that within the amplicon region, hypermethylation is present in lung, stomach, colon and breast tumors relative to normals. Furthermore this amplicon region detects hypermethylation in the majority of examined tumors regardless of subtype, stage of differentiation, age, and gender.

Example 5

Classification of Tumor and Normal Samples by Methylation Patterns

As seen above, by focusing on the methylation levels at individual amplicon CpGs, and on their average, a robust hypermethylation signal was observed in each type of cancer tested. Nevertheless, towards the goal of elucidating this region as a pan-cancer biomarker, a feature or a set of features in the methylation data was looked for to better distinguish tumors from normal samples. To do so the gynecological, colon, stomach, lung, and breast samples totaling 34 normal samples and 184 tumors were pooled. This allowed for testing of the best discriminating features within the methylation profiles and assessing which classification method performed best.

Starting from the perspective of the methylation status of all CpGs along individual reads, the 20 CpG positions of the amplicon region would provide $2^{20}$, or >1,000,000 possible methylation patterns. It is likely that only some of these patterns are present in each sample and aligned reads provide a record of the most abundant ones. Each pattern can be represented as a string of 20 characters, representing the methylation state of each CpG in the amplicon as a methylated, 'c', or unmethylated, 'c', respectively.

Figure 5A:
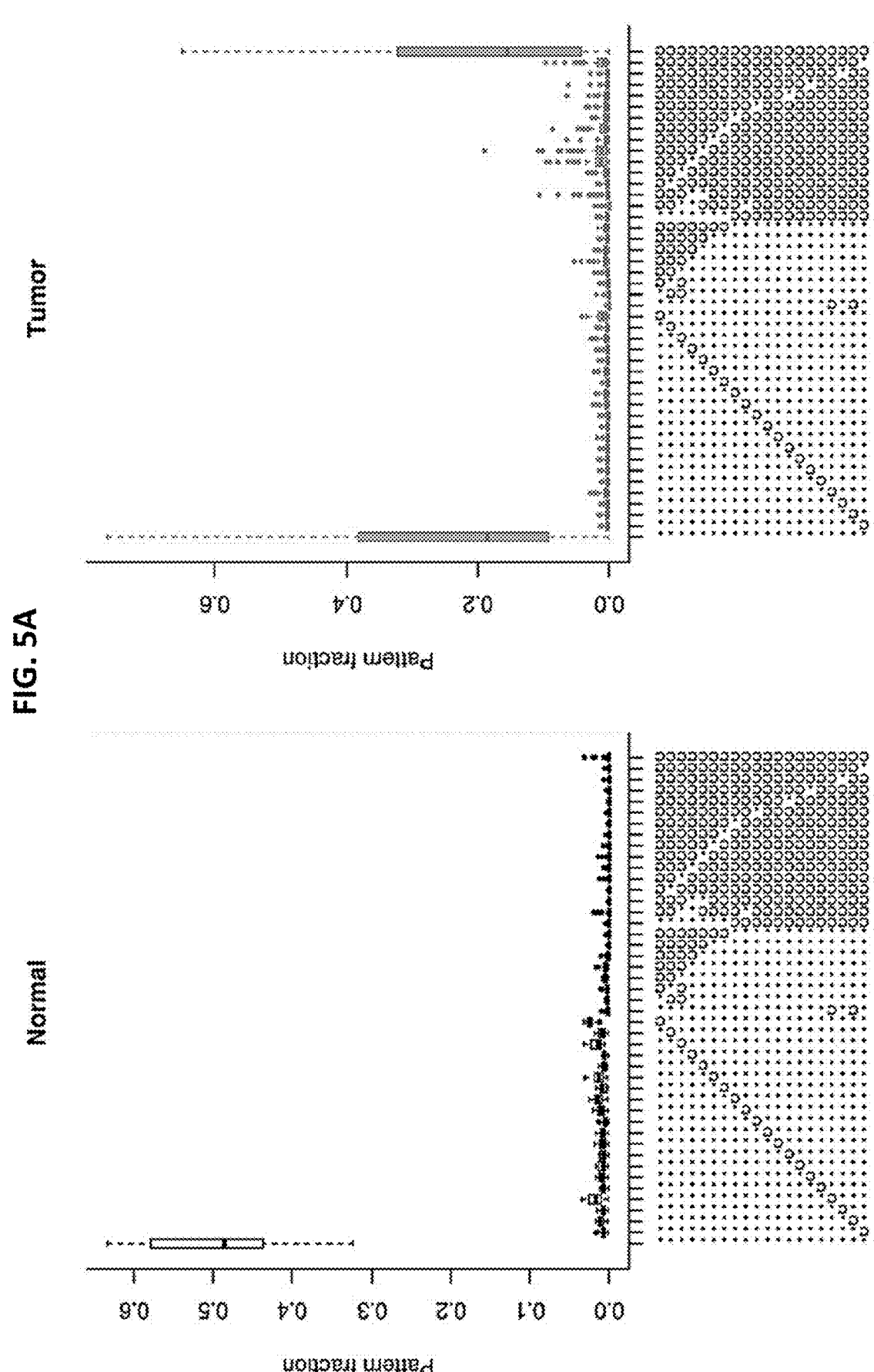
FIGS. 5A and 5B show a set of graphs illustrating the methylation patterns of aligned reads in tumor versus normal endometrial, colon, stomach, lung, and breast tissue samples. 5A: Frequency of the 45 most repeated patterns. Unmethylated cytosines converted to thymines appear as (.), whereas methylated cytosines that were protected from conversion appear as ("c"). Each symbol represents the status of one of the 20 CpG cytosines in the amplicon. 5B: Hierarchical clustering of the samples based on these 45 patterns. Heat map coloring reflects the relative abundance of a given pattern across samples—going from white to black in each row or pattern would correspond to moving from the bottom upward in the merged tumor-and-normal box plot for that same pattern, similar to 5A.

To create a set of features representing each sample, the data was compressed into the 30 most frequent patterns across normal samples and 30 most frequent patterns across tumors; their union yielded forty-four distinct patterns. There are two main groups in these patterns: those with low numbers of methylated reads (patterns with 0 or 1 methylated CpGs) and those with high numbers of methylated reads (18, 19, 20 methylated CpGs) (FIG. 5(A)). The low-methylation reads are frequent in both normals and tumors, whereas the high-methylation reads are primarily present in the tumors. It is unlikely that multiple reads with single methylated CpGs are due to inefficient bisulfite conversion, because there are multiple patterns with single unmethylated CpGs as well.

Figure 5B:
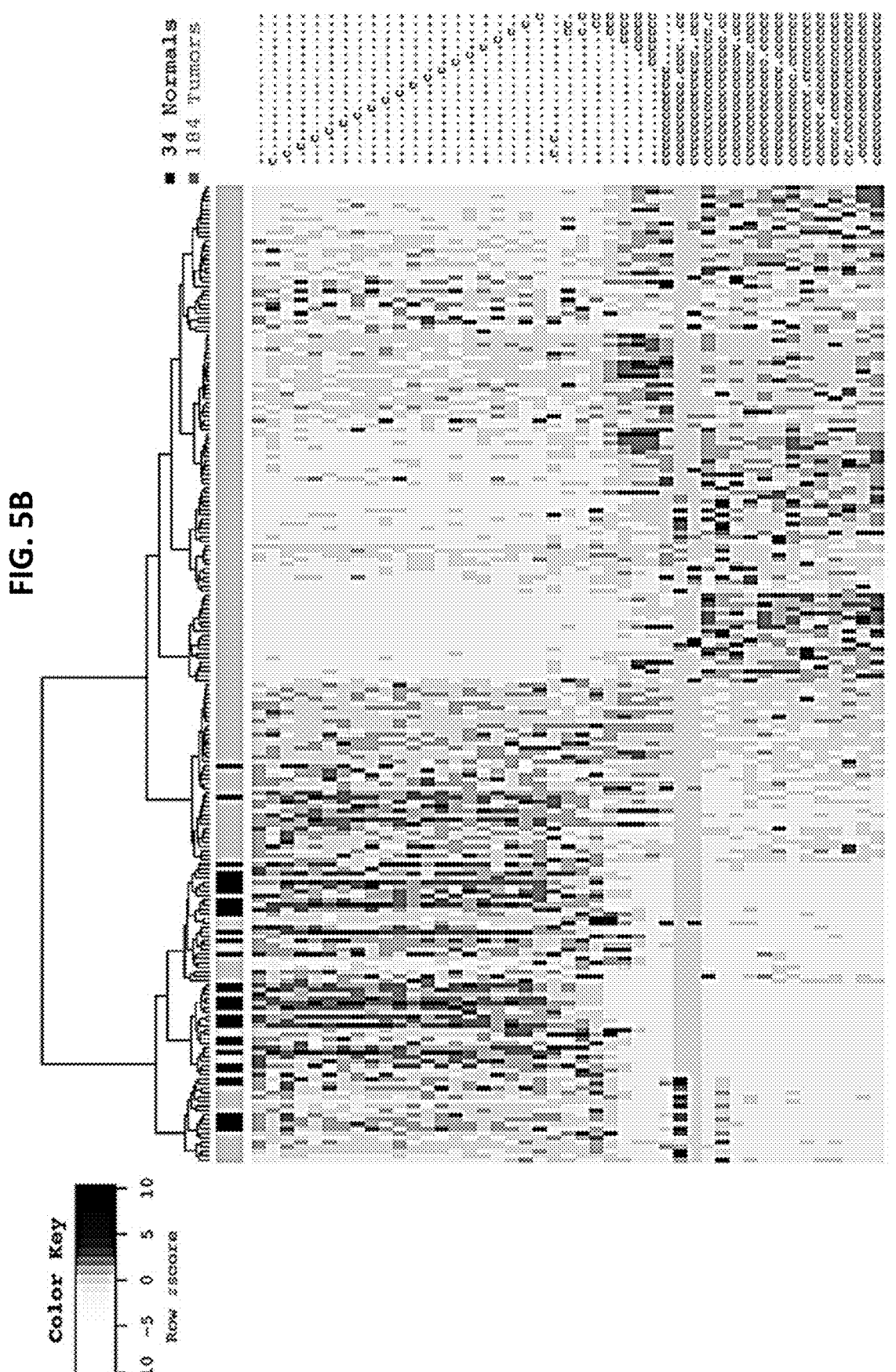

This set of features was used to analyze each sample and to distinguish tumors from normals. In unsupervised hierarchical clustering of samples (FIG. 5(B)) the left topmost branch is designated as a negative or normal sample classification, while the right branch is populated with the positive or tumor sample classification. The true-positive rate of classification was 81%, with a false-positive rate of 6%.

Figure 6B:
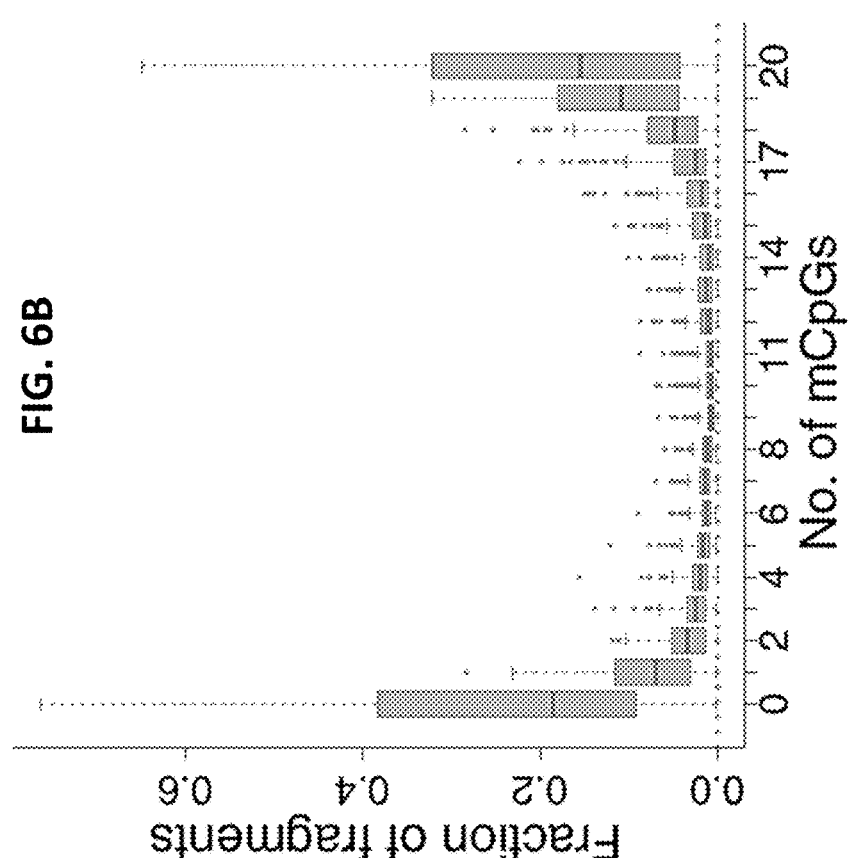
FIGS. 6A and 6B show a set of graphs illustrating the levels of CpG methylation (mCpG) of aligned reads in tumor versus normal endometrial, colon, stomach, lung, and breast tissue samples. Frequency of aligned reads as a function of the number of mCpGs, from 0 to 20, in normal (6A) and tumor (6B) samples. Different patterns with identical numbers of mCpGs have been grouped together.
Figure 6A:
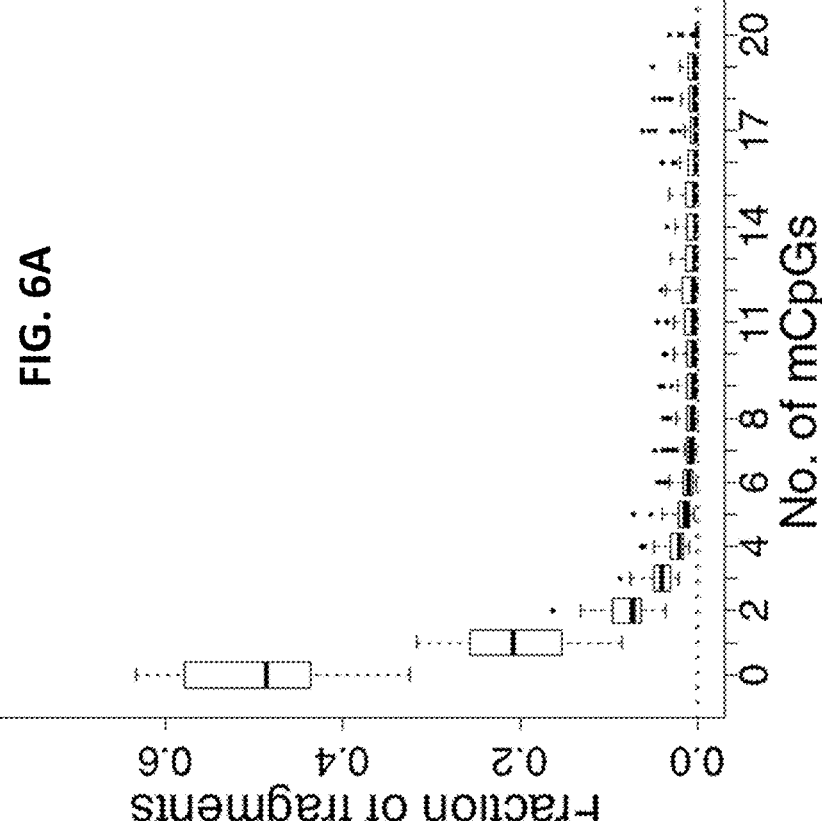

An alternative to treating the distinct patterns separately is to group reads with equal numbers of methylated CpGs together. Thus, each sample will be described by a set of 21 numbers $\{n_k\}$ representing aligned reads having exactly k CpGs methylated, where k ranges from 0 to 20. When normalized, these numbers represent corresponding frequencies or fractions, with all $n_k$ adding up to 1. The distributions of $n_k$ across normal and tumor samples are shown in FIGS. 6(A)-(B). Note that cases of fully unmethylated (k=0) and fully methylated (k=20) aligned reads consist of only one pattern from each sample and therefore are identical in FIGS. 5(A) and 6(A)-(B). In normals, approximately 50% of aligned reads carry no methylation (FIG. 6(A)), and most of the remaining aligned reads contain less than ten methylated CpGs. Note that there is a small contingent of fully methylated reads (median 0.03%) in the normal samples (7 out of 28 normals had no fully methylated reads and the distributions of aligned read numbers for these 7 and the remaining 21 normal samples are not significantly different—t-test and Wilcoxon test p-values are 0.53 and 0.84, respectively). In tumors (FIG. 6(B)) a relative lower presence of fully unmethylated reads were found, 19%, and much higher relative presence of fully methylated reads, 15% (all 184 tumors had fully methylated reads).

Having each sample represented by its set of methylation level fractions $\{n_k\}$, these numbers can be combined in multiple ways to define scalar features and assess the optimal classification approach. For example, the average methylation per sample can be calculated as m=

$$\left(\sum_{k=0}^{20} k n_k\right) / \left(20 \sum_{k=0}^{20} n_k\right).$$

Figures 7A, 7B:
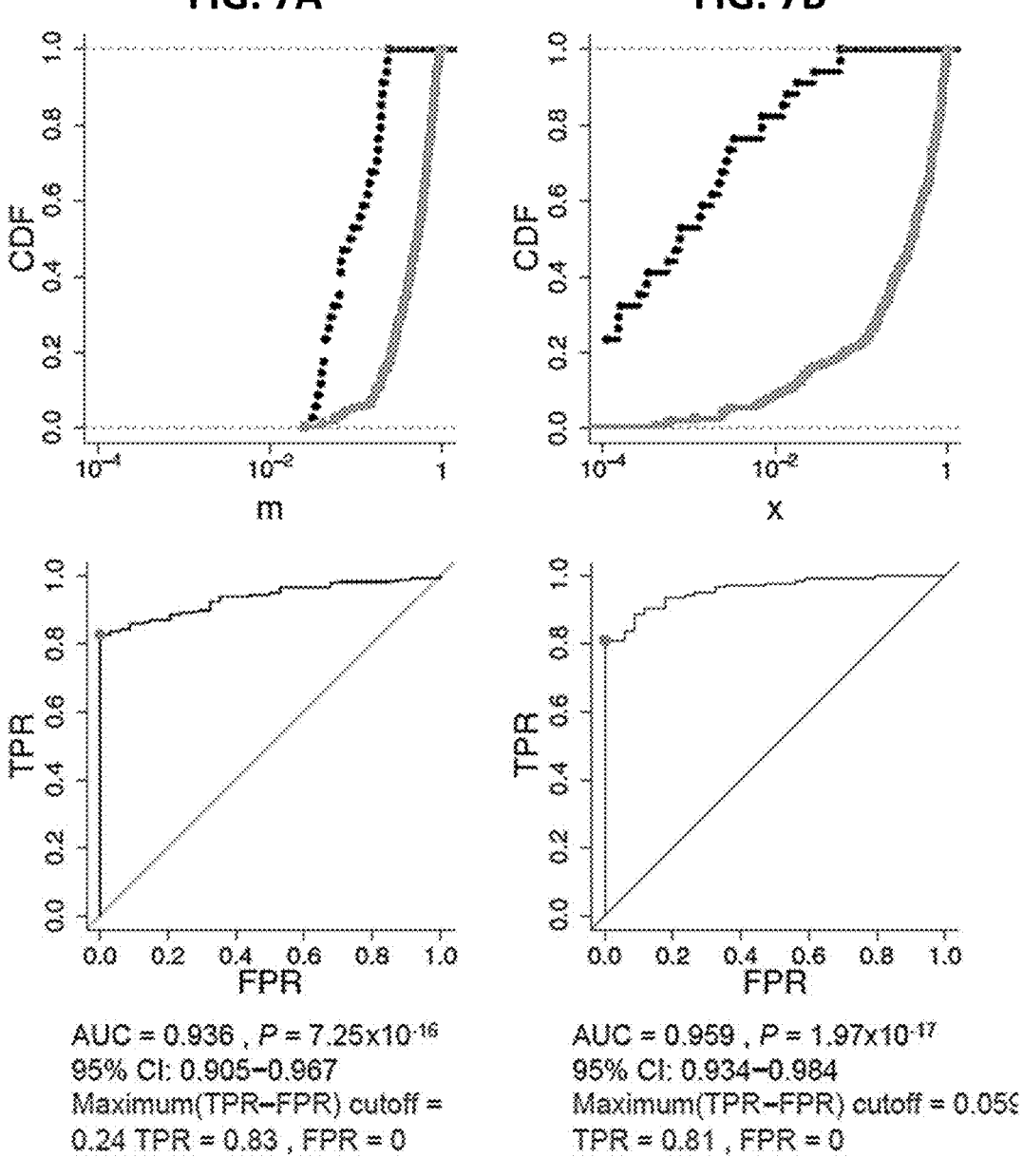
Figure 8:
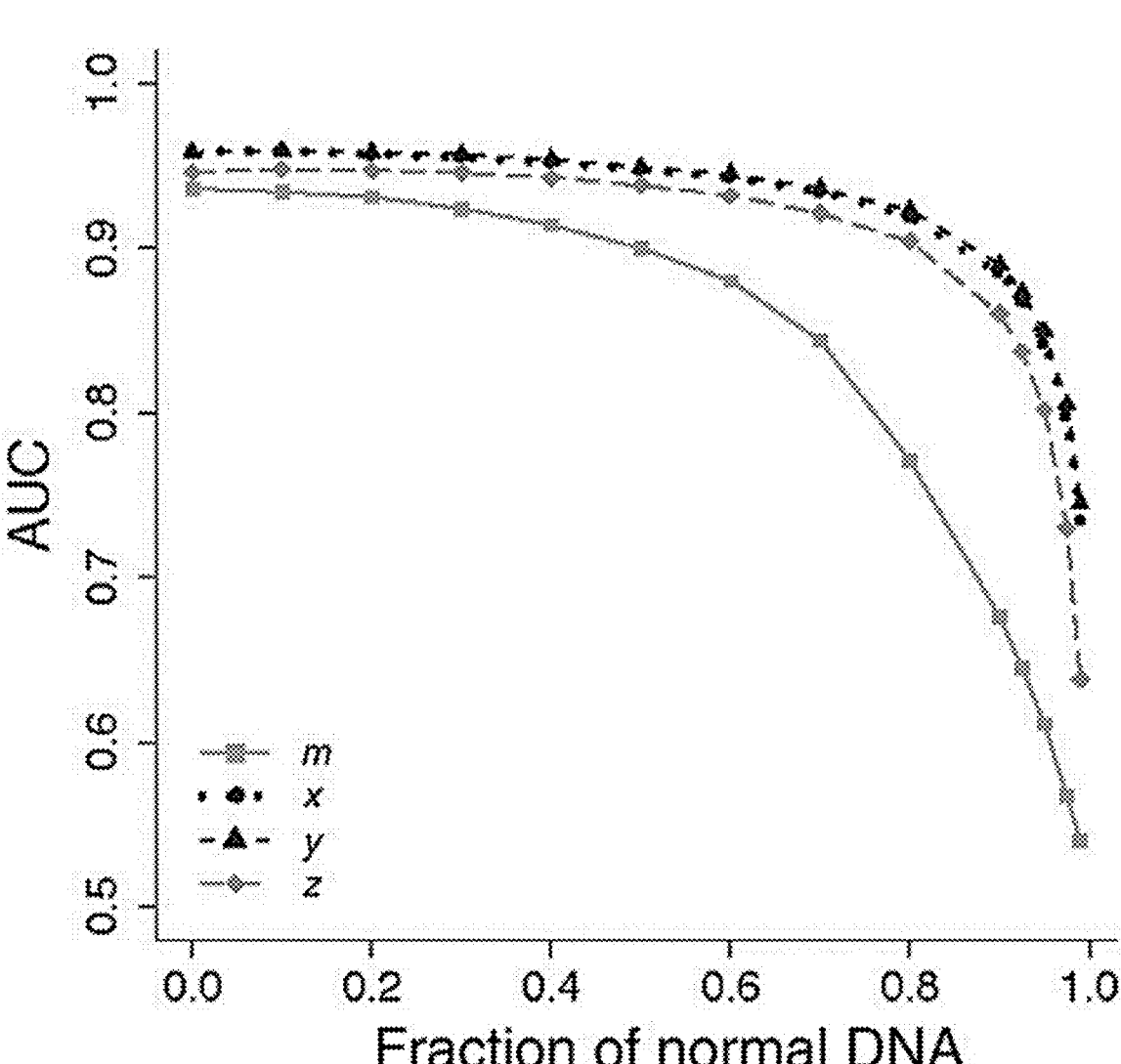
FIG. 8 shows a graph illustrating the performance of the four selected predictors (m, x, y, and z; defined in Examples section) in distinguishing endometrial, colon, stomach, lung, and breast tumors from normal samples at different simulated dilution levels. Area under the receiver operating characteristic curve (AUC) is plotted as a function of simulated tumor DNA dilution. The leftmost AUC values (when fraction of normal DNA is 0) correspond to the data presented in FIG. 7.

Using m, the pooled tumors separate well from normal samples (FIG. 7A (left column)), as shown by an area under the ROC curve (AUC) of 0.915 and a false positive rate (FPR) of 3.6% at a true positive rate (TPR) of 83%. Furthermore, the two groups of patterns that differ the most are k=0 and k=20 (i.e., fully unmethylated and fully methylated reads). Restricting attention to just these two groups, a ratio $x = n_{20}/(n_0 + n_{20})$ is defined and used to distinguish tumors from normals (FIG. 7(B)). In the absence of partially methylated reads, x would represent the average methylation per sample. Moreover, other similar ratios were explored, in order to potentially improve the classification performance by taking the partially methylated reads into account. In particular, the reads with low methylation (five or less mCpGs) were combined with the fully unmethylated reads and defined $$y = n_{20} / \left(n_{20} + \sum_{k=0}^{5} n_k\right)$$

(FIG. 7(C)), and similarly, the almost fully methylated reads were combined with fully methylated reads and defined $z = (n_{19} + n_{20})/(n_0 + n_{19} + n_{20})$ (FIG. 7(D)). However, these three ratios x, y and z (and other similar ratios) performed similarly, with AUCs between 0.926 and 0.94, which are improvements, but marginal, over the value of 0.915 from the average methylation fraction m (seen in FIG. 7(A)). Nevertheless, the same simplicity may not apply to samples generated from circulating tumor DNA where the tumor signal is likely to be diluted in a background of non-tumor signal.

In addition to the classification schemes above, it was investigated how well tumors from normals could be distinguished using more sophisticated machine learning algorithms. k-nearest neighbors (KNN) and support vector machine (SVM) algorithms were applied, utilizing the three alternative sets of features described above: methylation values at each of the 20 individual CpGs, forty-four most recurrent pattern frequencies, and frequencies of groups of patterns $\{n_k\}$ (FIGS. 15(A)-(C)). The performance of the SVM using the most abundant pattern frequencies was somewhat better than the hierarchical clustering performance (FIG. 5(B)), which is based on the same data (i.e., on the frequencies of the most abundant patterns). Overall, KNN and SVM classification performances are similar across the three alternative representations of the samples (FIGS. 15(A)-(C)) and, moreover, are similar to the performances based on scalar ratios defined above (FIGS. 7(A)-(D)).

In summary, the primary sequencing data covering 20 CpG positions elucidate individual methylation patterns whose frequencies can be used to classify samples into tumor and normal categories by several methodologies. The data representing raw abundances of CpG methylation patterns of aligned reads carry the most detail, but can be compressed, for example into methylation levels of individual CpGs (FIGS. 3(A)-(B), 4(A)-(B)) or into patterns grouped by the number of methylated CpGs (FIG. 6(A)-(B)). The average methylation levels were examined (FIG. 7(A)) and the ratios based on the most extreme groups of fully methylated and fully unmethylated reads (FIG. 7(B)) were considered, with some modifications (FIG. 7(C),(D)). Roughly similar performances were found in all the cases (i.e., similar TPRs and correspondingly similar FPRs in FIGS. 7(A)-(D) and FIGS. 13(A)-(C)). The advantages of the scalar predictors m, x, y and z are that they are easy to interpret and work with, which cannot be said about the machine learning algorithms that require much more validation and parameter selection.

Example 6

Detection and Classification of Simulated Dilute Tumor DNA in a Blood Diagnostic Model In Examples 3 and 4, robust detection of the hypermethylation signal from solid tumor surgical resections of different cancer types is demonstrated. This example demonstrates the clinical relevance of the classification methods of the present disclosure to the detection of hypermethylation in circulating tumor DNA, by diluting the signal representing tumor samples into that representing normal samples. 34 normal samples and 184 tumors from the panels comprising five tumor types were used to construct a collection of in silico dilution data. Briefly, for each tumor sample, one of the normal samples was randomly matched, and the signals were mixed together at a chosen proportion. The fraction of normals in the mixture was varied from 0.1 (10%) to 0.99 (99%). Hence, in the case of 99% normal fraction, the tumor contributes 1% to the methylation signal. Each dilution level gave rise to a separate data set (as detailed in Example 1). Sets of tumor dilutions with different fractions of normals were assessed independently.

The low methylation signal observed in the 34 normal tissue samples was assumed to be a suitable approximation of methylation that may be observed in normal blood, in agreement with data from methylation array studies (e.g., Gene Expression Omnibus; data sets GSE64950 with 36 samples from six individuals and GSE55763 with 2711 samples from 2664 individuals). For example, the mean±SD methylation of the four CpGs within the amplicon that are also represented on the methylation arrays (FIG. 2) was 12%±7% in our normal tissue samples, comparable to the BMIQ-normalized measurements of 10%±5% and 6%±3% in the GSE55763 and GSE64950 data sets, respectively.

On each set of tumor dilutions, the same classification analysis was performed as was done on the original, undiluted data set (as seen in FIGS. 7(A)-(D)). The same selection of features was used, including average methylation fraction m and the ratios of methylated pattern group frequencies: x, y and z. From these data, it was found that x and y are the best in terms of yielding the highest AUC values for all dilution levels from 0 (undiluted) to 99% (FIG.

8). The classification based on average methylation is just slightly below that for other predictors for the undiluted case, however, it deteriorates much faster with stronger dilutions. The y ratio, which incorporates aligned reads with one to five methylated CpGs, is slightly, but consistently better than x, which is based solely on the fully methylated and fully unmethylated reads. In addition to x, y and z, a simple classification was considered based on the fraction $n_{20}$ of fully methylated reads out of all reads. The analysis revealed that it performs similar to z at low dilution levels, similar to x at intermediate dilution levels, and becomes very close to y at higher dilution.

Figure 16B:
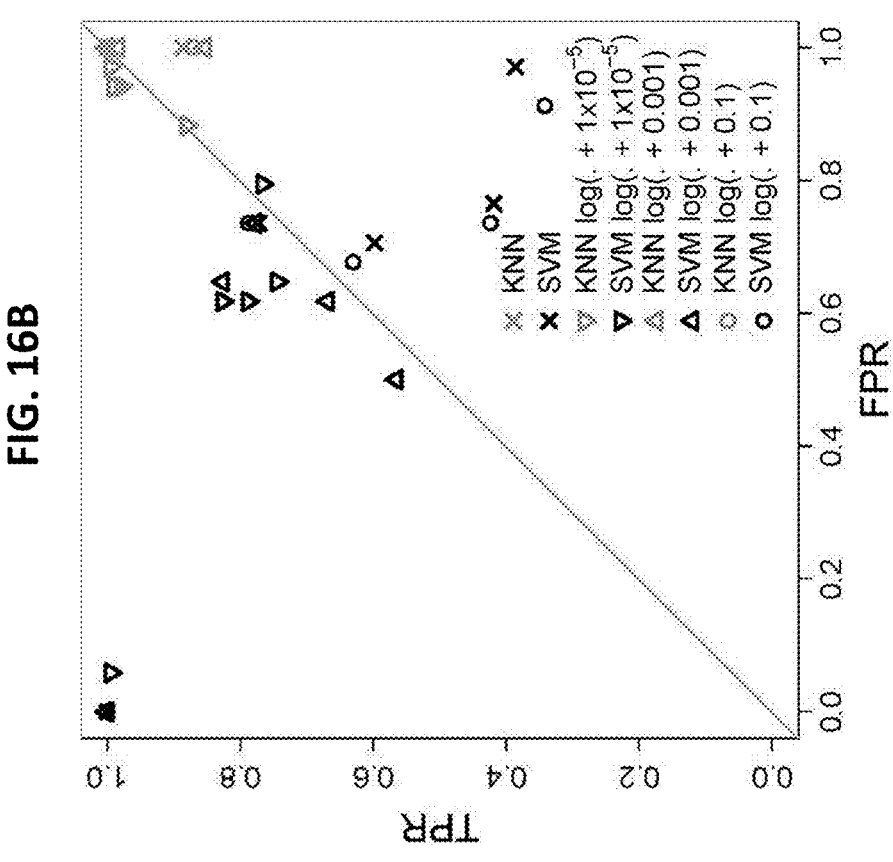
FIGS. 16A-16B show a set of graphs illustrating the true-positive rates (TPR) and false-positive rates (FPR) using k-nearest neighbors (KNN) and support vector machine (SVM) leave-one-out cross-validations to classify endometrial, colon, stomach, lung, and breast tumors versus normal tissue. Different data transformations are indicated by different symbols. Identical symbols on the same plot indicate different choices of nearest neighbors for the KNN algorithm (grey) and different cost values for the SVM algorithm (black). Shown are typical results for tumor dilutions with 90% normal DNA signals (16A) and 99% normal DNA signals (16B), using frequencies of aligned reads with different numbers of methylated CpGs. The cases of apparently perfect or near-perfect SVM classification are actually an artifact of a misleading behavior that occurs with a low value of the cost parameter (0.1); in those leave-one-out cross-validations, when a normal sample is left out, there are 33 normal samples and 184 tumor samples in the training set, and the prediction for any test is always normal. When a tumor sample is left out, there are 34 normal samples and 183 tumor samples in the training set, and the prediction is always tumor. This behavior was validated with randomly generated 21-dimensional sample vectors drawn from a uniform distribution.
Figure 16A:
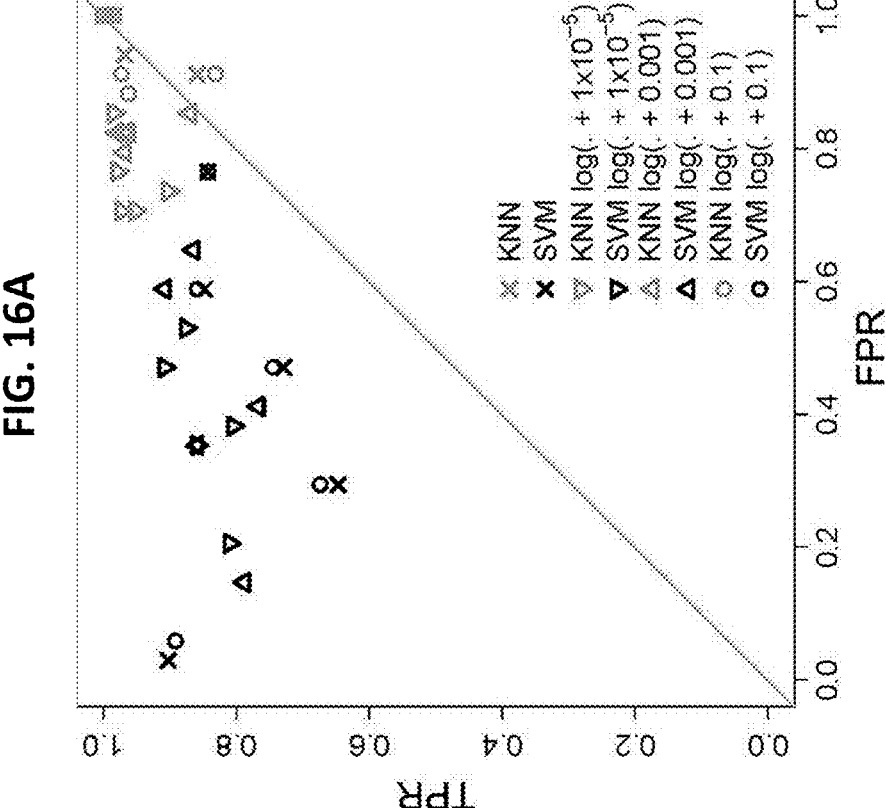
Figure 17C:
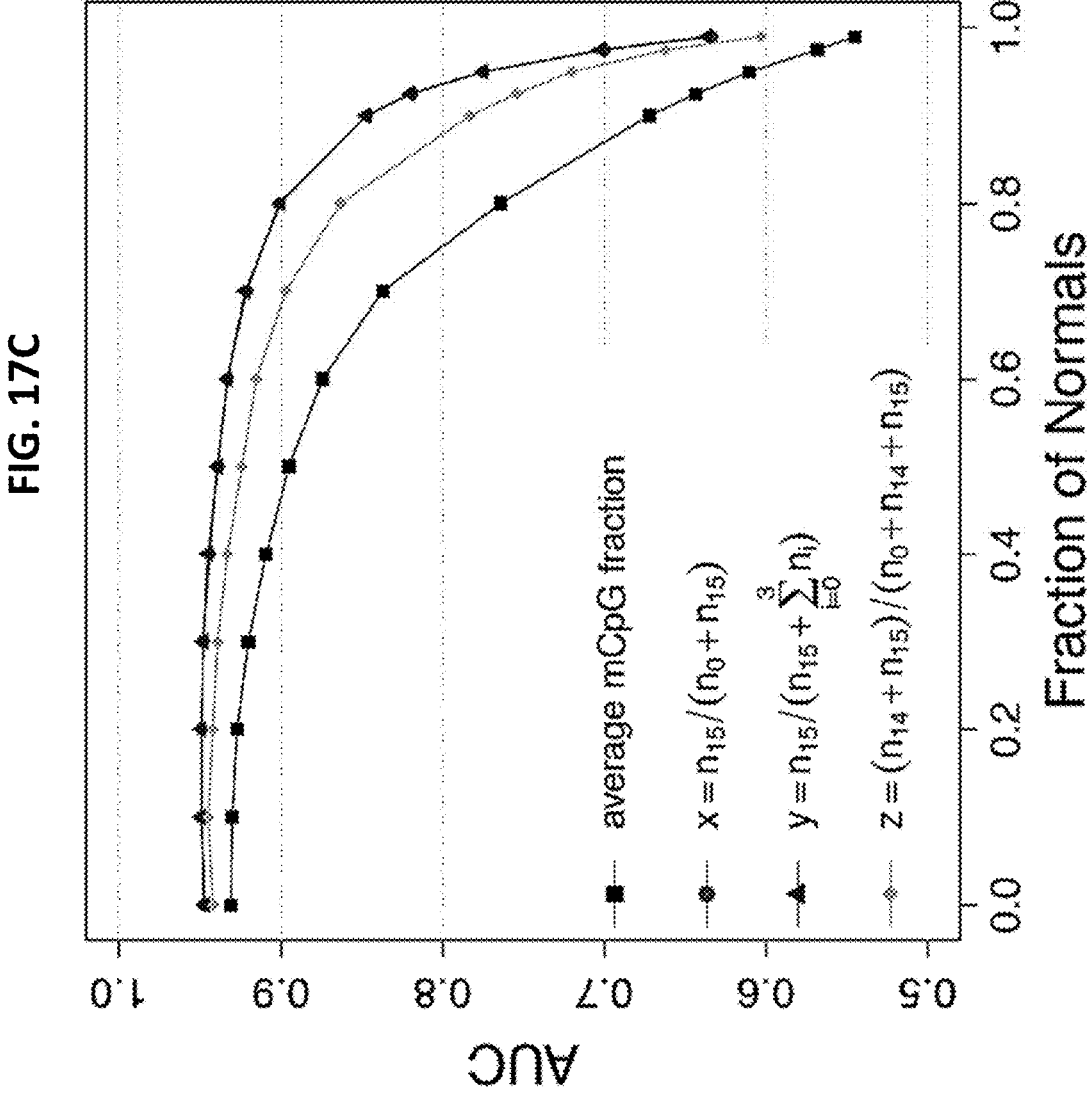
Figure 18:
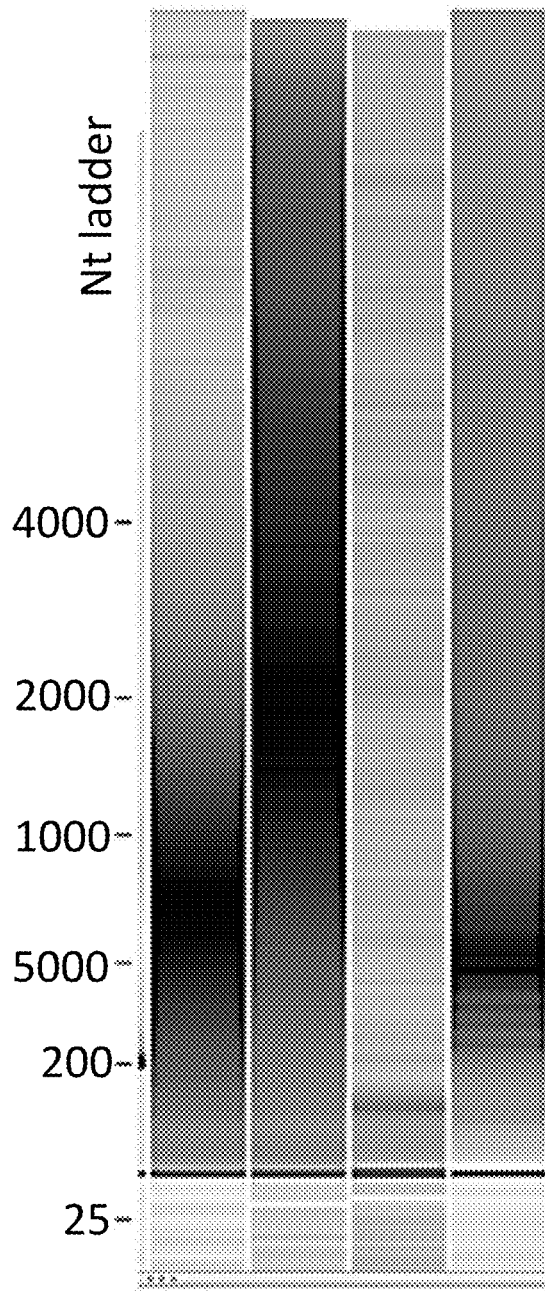
FIG. 18 shows a digital image illustrating that treatment of plasma DNA with bisulfite reduces the average size to 160 bp, compared to genomic DNA, which retains 1000 base average size.
Figure 19:
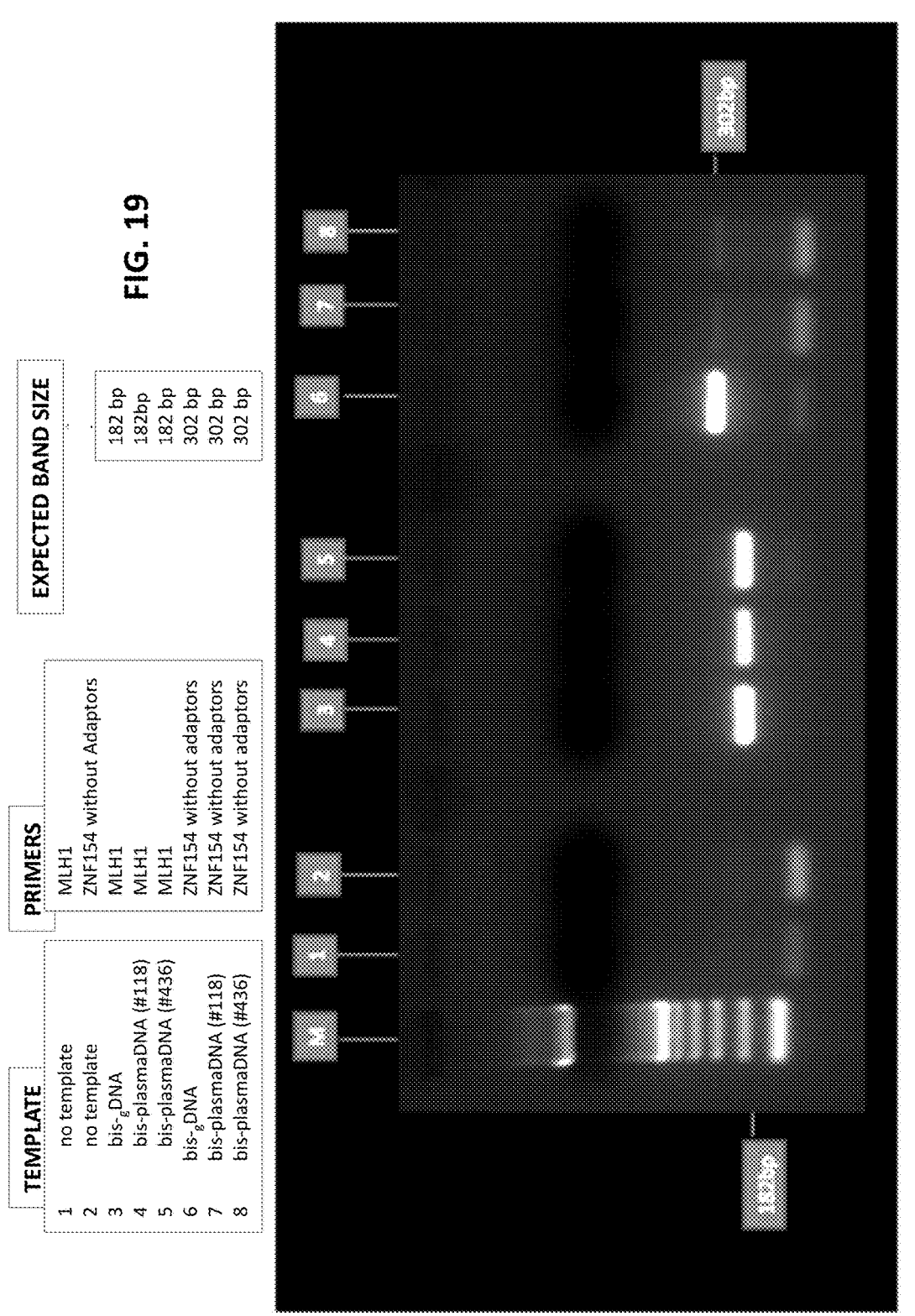
FIG. 19 shows an image of an agarose gel illustrating that the 302 base pair amplicon of SEQ ID NO: 5 can be amplified from patient blood plasma samples. Lane M is a ladder for size measurement of DNA samples. Lanes 1 and 2 are negative controls with primers but no template. Lanes 3-5 show amplification of a 182 base-pair region of MLH1, Lane 3 is a positive control and Lanes 4-5 show amplification from patient blood plasma samples. Lane 6 shows a positive control for amplification of the 302 base pair amplicon. Lanes 7 and 8 show amplification of the 302 base pair amplicon from patient blood plasma samples.

At 90% dilution, the ratios x and y perform well with AUCs around 0.84, while AUC for the averaged methylation-based ROC is much worse at 0.64. Even at the highest considered dilution, 99%, the ratios x and y still demonstrate a substantial ability to discriminate tumors from normals, with AUCs around 0.7 (Wilcoxon p<0.0003, 95% CI 0.57-0.83; FIGS. 9(B),(C)). At this dilution level, the AUC for the averaged methylation-based ROC is only 0.53, which is marginally above the random guessing value of 0.5 (Wilcoxon p=0.57, 95% CI 0.42-0.64; FIG. 9A). When the machine learning approaches were applied, SVM and KNN cross-validations, it was found that they didn't add any performance value at high dilution levels. For example, at 90% dilution their performance was at best comparable to that of x or y-based classification (FIGS. 15(A)-(B)), while at 99% dilution the SVM and KNN predictions were generally worse than a random guess (TPR<FPR) or had severe underfitting (FIG. 16). Thus it was concluded that machine learning classifiers provide no additional benefit over approaches using methylation ratios with respect to the classification of these data. The advantage of the scalar predictors m, x, y, and z is that they are easy to interpret and work with, which cannot be said about the machine learning algorithms, which require much more validation and parameter selection.

Finally, to estimate the classification capacities of the approach of the present disclosure in individual tumor types, dilution simulations were performed similar to those described above but keeping only one tumor type present at a time. The same pooled set of normal samples were used in each case (FIGS. 14(A)-(F)). Endometrial and colon tumors were the easiest to classify, with the best AUCs, >0.95, up to 90% dilution. Breast tumors were the hardest to classify, with all AUCs at <0.90. In lung tumors, the AUC based on m (mean methylation) performed better than the alternatives (x, y, and z) at up to 70% dilution, but it quickly degraded at higher dilutions. Interestingly, the breast tumor AUC values based on all four features (m, x, y and z) grew initially with dilution increasing until ~20%; this was definitely unexpected, but is possible, likely due to a relatively high proportion of (undiluted) tumors showing methylation signals below normals.

Thus, by developing a simulated model of tumor sample dilution, representing dilute signals from circulating tumor DNA, this disclosure demonstrates that the presently disclosed methods have potent clinical potential for diagnostics. Even when tumors contributed just 1% to the total methylation signal, tumors could be discriminated from normal tissue samples using specific methylation patterns at the ZNF154 CGI, with an AUC of 0.74 (FIG. 9, B and C). A mathematical technique, constructing a convex hull, can improve the ROC curve and increase the AUC; this somewhat improved the classification performance to the AUC of 0.79 (FIG. 9C and 14).

Example 7

Brief Summary of Bisulfite Amplicon Sequencing Data Analysis

Sequenced reads in which non-methylated Cs converted to Ts were aligned to the human reference genome using Bismark software. Unaligned reads and reads aligned to the wrong genomic coordinate were excluded from the analysis. Inefficiency of bisulfite conversion was estimated from a fraction of non-converted Cs in a non-CpG context and found sufficiently low.

The methylation level of each sequenced and properly aligned read (DNA fragment) was determined by counting the number, k, of methylated CpGs in the region of the amplicon corresponding to nucleotides 58,220,424 to 58,220,670 of chromosome 19 (k will be between 0 and 20). Reads with identical k are grouped together and the frequency of each group, $n_k$, is calculated ($n_k$ is the frequency of reads with exactly k methylated CpGs). Thus each sample is characterized by a set/collection of frequencies, $\{n_k\}$, with k ranging from 0 to 20.

Examination of the data revealed that the two groups of patterns with the strongest differential representation are the fully unmethylated and fully methylated reads. Focusing on just these two groups, a ratio, $X=N_{20}/(N_0+N_{20})$ is defined, to distinguish tumor from normal tissue samples. Also, reads with low methylation (five or fewer methylated CpGs) are combined with fully unmethylated reads, defining a ratio, $Y=N_{20}/(N_0+N_1+N_2+N_3+N_4+N_5+N_{20})$. Likewise, almost-fully methylated reads are combined with fully methylated reads to define a ratio, $Z=(N_{19}+N_{20})/(N_0+N_{19}+N_{20})$. For comparison, a simple measure is calculated, based on the average level of sample methylation, M.

For each of the X, Y, Z or M as the measure of choice, a receiver operating characteristic (ROC) curve was constructed and an area under it (AUC) was calculated, based on knowledge of each sample status (tumor or normal). AUCs can range between 0.5 and 1 and higher values generally imply better classification performance The three ratios, X, Y, and Z, performed similarly, with areas under the ROC curve (AUCs) between 0.946 and 0.959 on tumor DNA, slightly above M at 0.936, using tumor DNA.

As a proxy for circulating tumor DNA, dilutions of the tumor signal into a background of normal signal were simulated, to mimic low level circulating tumor DNA in blood. Each simulated diluted tumor was produced by computationally mixing a randomly selected actual tumor signal with a randomly selected actual normal signal, at a specified proportion. For example, 90% dilution means 10% tumor signal and 90% normal signal. Normal data remained the same as in the original dataset of undiluted tumors.

For the diluted samples, the same selection of features were used, including the average methylation fraction, M, and the ratios of methylated pattern group frequencies, X, Y, and Z. X and Y yielded the highest AUC values for all dilution levels, from 0 (undiluted) to 99% (Table 1). Although the AUC for classification based on average methylation, M, was just slightly below that for other predictors in the case of undiluted samples, it deteriorated much faster with stronger dilution. The Y ratio, which incorporates aligned reads with one to five methylated CpGs, performed slightly but consistently better than X, which is based solely on fully methylated and fully unmethylated reads.

It was found that when tumor signal was diluted to just 1% of the total methylation signal, the capacity to discriminate cancer samples from normal samples using methylation at the ZNF154 amplicon remained detectable, with an AUC of approximately 0.74. Using mathematical techniques this was further improved to 0.79.

It is believed that such individual read-based analysis has not been performed before in order to characterize amplicon (locus) methylation and compare different samples. Current methods either use array probes or employ Sanger or conventional pyrosequencing. These methods do not provide correlational information along individual DNA fragments and yield only sample-averaged methylation measurement. Another widespread approach, quantitative methylation-sensitive PCR (qMSP) is aimed at quantifying fully methylated and/or unmethylated fragments, but it cannot controllably filter out fragments with intermediate methylation levels. Therefore, it is believed that the presently disclosed NGS sequencing-based analysis is more accurate.

Example using actual data: (1) Using amplicon sequencing of target regions after bisulfite treatment, 20 nucleotide positions are assessed, the AUC would be 0.96 using tumor DNA for the measurement. (2) To simulate the weaker signal and higher background of circulating tumor DNA, each result was diluted to 10% signal strength by adding 90% signal from normal DNA (which is primarily unmethylated). The 90% dilution was calculated and the AUC is reported below for each tumor type (normal samples were pooled from all types to give more data).

TABLE 1

AUC numbers for 90% dilution of the tumor signal using computational simulations.

| Cancer type | | Lung | Gyn | Stomach | Colon | Breast | Pooled types | Average (excluding pooled) |
|---|---|---|---|---|---|---|---|---|
| Bio- | X | 0.837 | 0.947 | 0.896 | 0.956 | 0.798 | 0.885 | 0.887 |
| informatic | Y | 0.842 | 0.951 | 0.903 | 0.959 | 0.801 | 0.890 | 0.891 |
| approaches | Z | 0.825 | 0.921 | 0.862 | 0.937 | 0.762 | 0.860 | 0.861 |
| | M | 0.710 | 0.718 | 0.619 | 0.705 | 0.624 | 0.676 | 0.675 |

Notes: (1) In every case tested, bioinformatics approaches X, Y and Z give a better classification than the average methylation signal, M. Also they improve upon the numbers returned by the ILLUMINA data simulation (see Table 2). (2) For diagnostic purposes, using the ILLUMINA methylation array platform for circulating tumor DNA is not effective because it requires 500 ng of starting material, and examines 450,000 sites per sample. One chip is required per each sample/sold as 24 chips per batch). (3) Circulating tumor DNA is often recovered in amounts less than 500 ng. The average size distribution is extremely small (-160 nt), making it necessary to optimize the treatment conditions to even see a 300 bp fragment. (4) Amplicon sequencing enables a higher throughput where 96 samples can be assessed in one sequencing run, with the cost of roughly $20 per sample.

Comparison to existing data collection methods: Shown in Table 2 is the AUC number for prediction of tumor presence using the ILLUMINA DNA methylation assay—considering only one CpG position on the array—from tumor DNA (derived directly from tumor tissue). Using tumor DNA would give an average AUC of 0.95 if tumor DNA were being used for the predictions. To simulate the weaker signal and higher background of circulating tumor DNA, each result was diluted to 10% signal strength by adding 90% signal from normal DNA (which is primarily unmethylated). These numbers are not directly comparable to Table 1, however, show performance worse than the bioinformatic approaches using amplicon sequencing. It is noted that the data is Table 2 is simulated data which may have limitations in practice in view of minimum thresholds for array detection relating to amounts and sizes of DNA collected.

TABLE 2

Simulated 90% dilution AUC numbers, using data derived from the ILLUMINA platform (calculated from TCGA raw ILLUMINA bead array data)

| Cancer type | breast | Colon | lung | lung | Stomach | uterine | Pooled types | Average (excluding pooled) |
|---|---|---|---|---|---|---|---|---|
| AUC | 0.763 | 0.850 | 0.740 | 0.806 | 0.836 | 0.858 | 0.815 | 0.809 |

Example 8

Determination of DNA Methylation of Plasma Cell Free DNA Using Bisulfite Amplicon Sequencing This example provides a brief description of assays that show that methylation of nucleotides 58,220,424 to 58,220,670 of chromosome 19 of cell-free genomic DNA from plasma samples can be detected using the disclosed bisulfite amplicon sequencing assays, and used to classify tumor from non-tumor samples.

Figure 20:
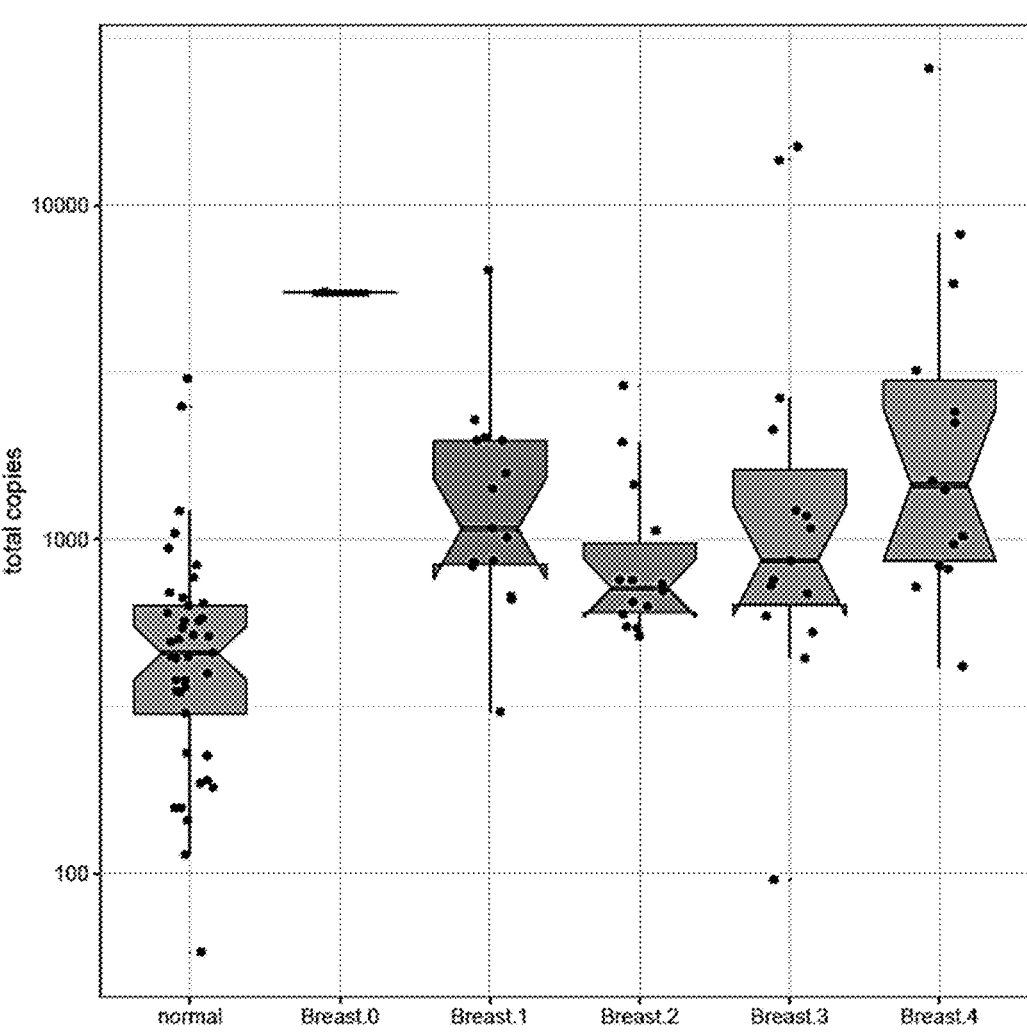
FIG. 20 shows a graph illustrating droplet digital PCR assays of target regions from normal plasma versus breast cancer by stage (0-4).

To show that DNA containing nucleotides 58,220,424 to 58,220,670 of chromosome 19 is detectable in plasma, digital droplet PCR (ddPCR) was used to measure the numbers of amplifiable DNA fragments containing this DNA in normal plasma samples, and different stage breast cancer patients' plasma (14-20 samples each, except one in stage zero) (FIG. 20). Tumor-associated plasma samples show more fragments of interest, but there is a substantial overlap with the normal samples.

Figure 21:
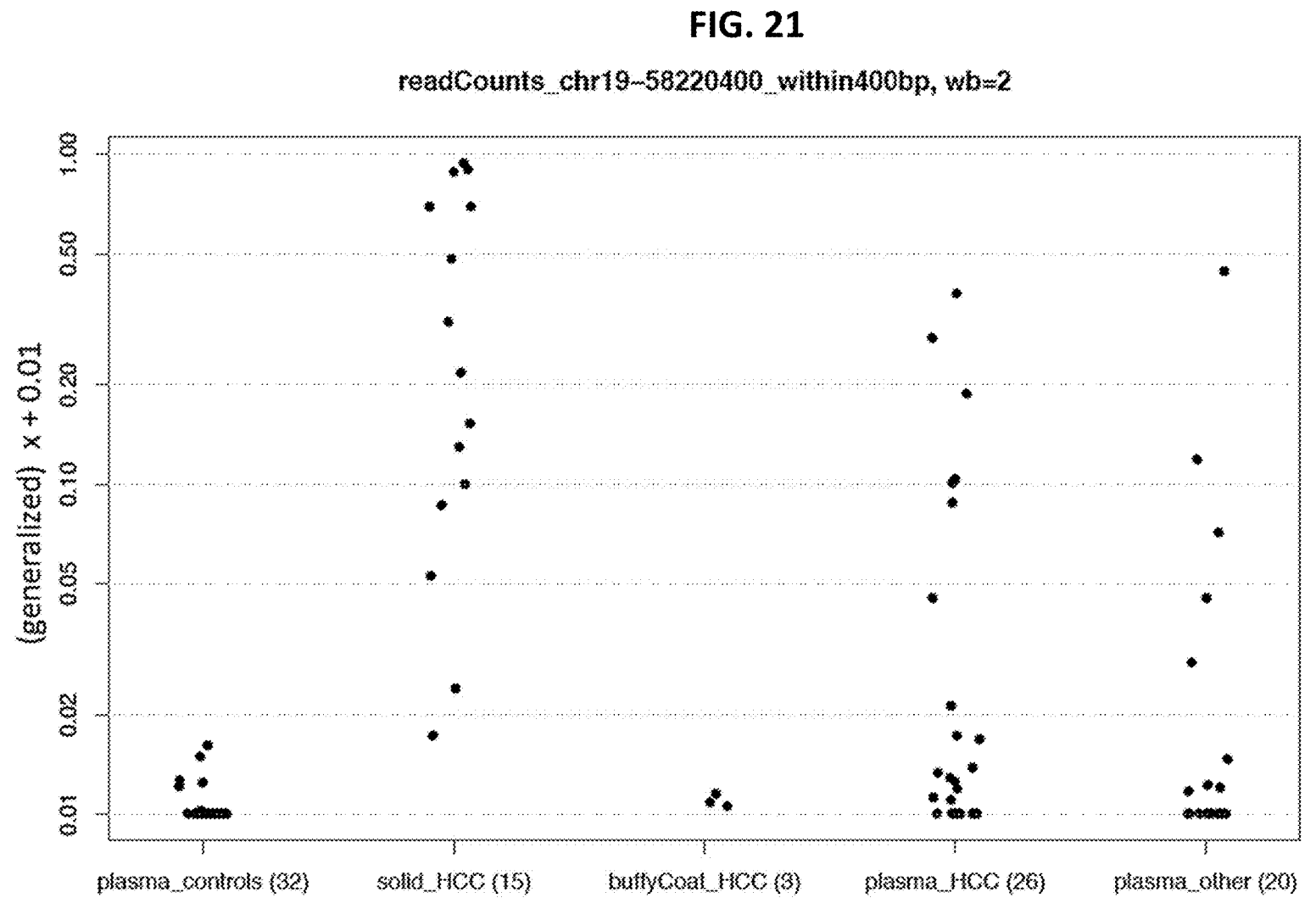

Additionally, plasma samples available from a published whole genome bisulfite sequencing study (using HCC—hepatocellular carcinoma, and several other cancers, Chan et al., Noninvasive detection of cancer-associated genome-wide hypomethylation and copy number aberrations by plasma DNA bisulfite sequencing, Proc Natl Acad Sci U S A. 110(47):18761-8, 2013, incorporated herein by reference) were analyzed (FIG. 21). In this dataset, the number of sequencing reads in the ZNF154 locus of interest is low, the reads are shorter than SEQ ID NO: 5 amplicon, and have variable numbers of CpGs. Nevertheless, this dataset can be used to illustrate and compare the ability to detect tumor hypermethylation signal using either simple average methylation measurements per sample or selectively focusing on fragments with multiple CpGs that are either all methylated or all unmethylated (as a generalization of the x ratio when there is no amplicon data available). Even with all the limitations of this dataset, performing the analysis similar to using the (generalized) x ratio improves tumor detection compared to average methylation analysis. This data shows that there is a notable separation of signal between healthy plasma controls and cancer plasma samples.

To show that the disclosed methodology can be used to classify plasma samples from tumor patients, plasma samples from normal/healthy individuals and plasma samples from one individual with prostate, one with pancreas, one with breast and 3 with colon tumors were analyzed as described herein. Amplicons generated during bisulfite sequencing assays were sequenced on an Illumina MiSeq instrument and analyzed as described above. Specifically, the average percent methylation (% mCpG) across the amplicon was calculated, as well as the x and y ratios, for each sample. Using % mCpGs normal and tumor samples are hardly different (one-sided t-test, p-value=0.24), while tumors show substantially higher x (p-value=0.048) and y (p-value=0.047) values than normal samples. Corresponding results using the x ratio on tumor and normal samples are plotted in FIG. 22 (as "_160328"). These results show that using x and/or y ratios facilitates tumor detection in diluted samples, like blood plasma.

Figure 22:
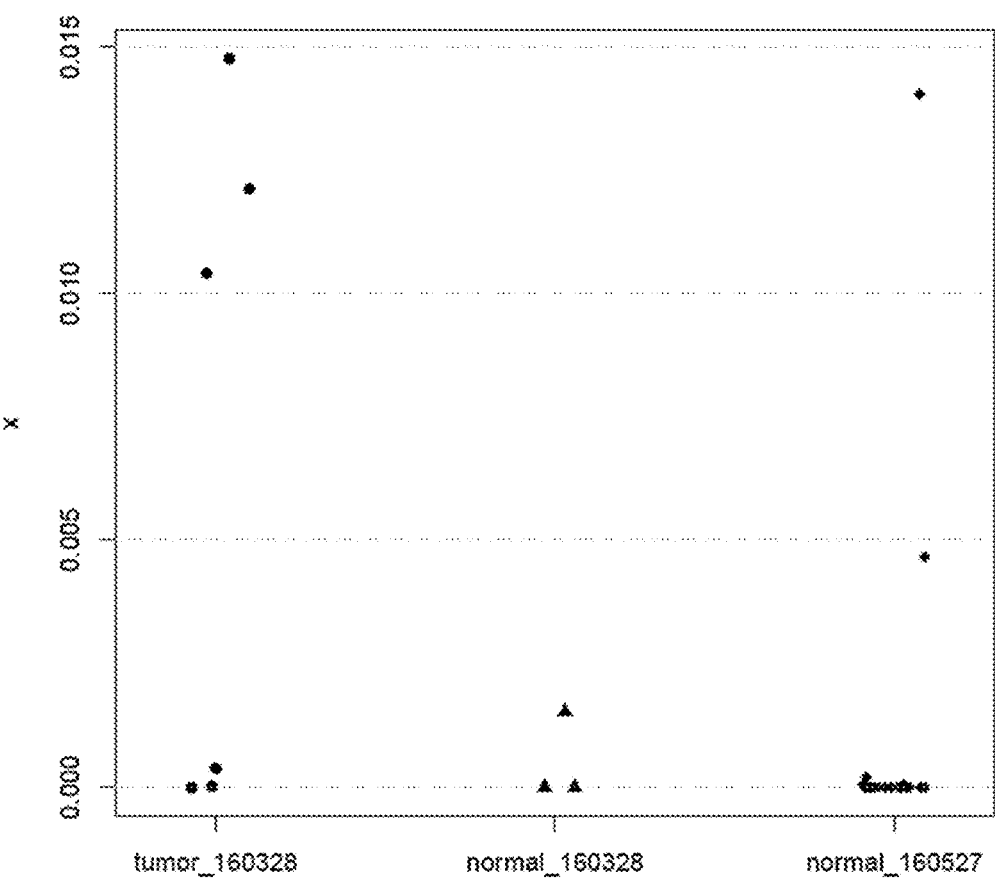
FIG. 22 shows a graph illustrating that the disclosed bisulfite amplicon sequencing assay, using the "x" ratio, shows elevated signal in 3 of 6 plasma samples from tumor patients with compared with an elevated signal in only 1 of 23 plasma sample from healthy control patients without tumors.

Using an additional set of 20 normal plasma samples the separation was clear between normals and tumors (p-values of 0.06 (one-sided t-test) and 0.001 (one-sided Wilcoxon rank sum test)), with only one normal sample measuring high (only equation x is shown) (see FIG. 22, samples "tumor_160328" vs. "normal_160527"). This is reflected in higher areas under the ROC curve (AUC) for x and y (0.88 and 0.87) versus a measure of average percent methylation across the amplicon region (0.80). Although average percent methylation was significantly higher in the tumor samples than the normal samples (one-sided t-test, p-value=0.007; one-sided Wilcoxon rank sum test, p-value=0.01), there still is a problem of a clean separation, leading to the lower AUC. Yet another batch of 21 normal plasma samples was analyzed, and all these samples showed x=y=0, indicating that there is no tumor-associated signal in that batch of normal samples (not shown in FIG. 22).

Figure 23:
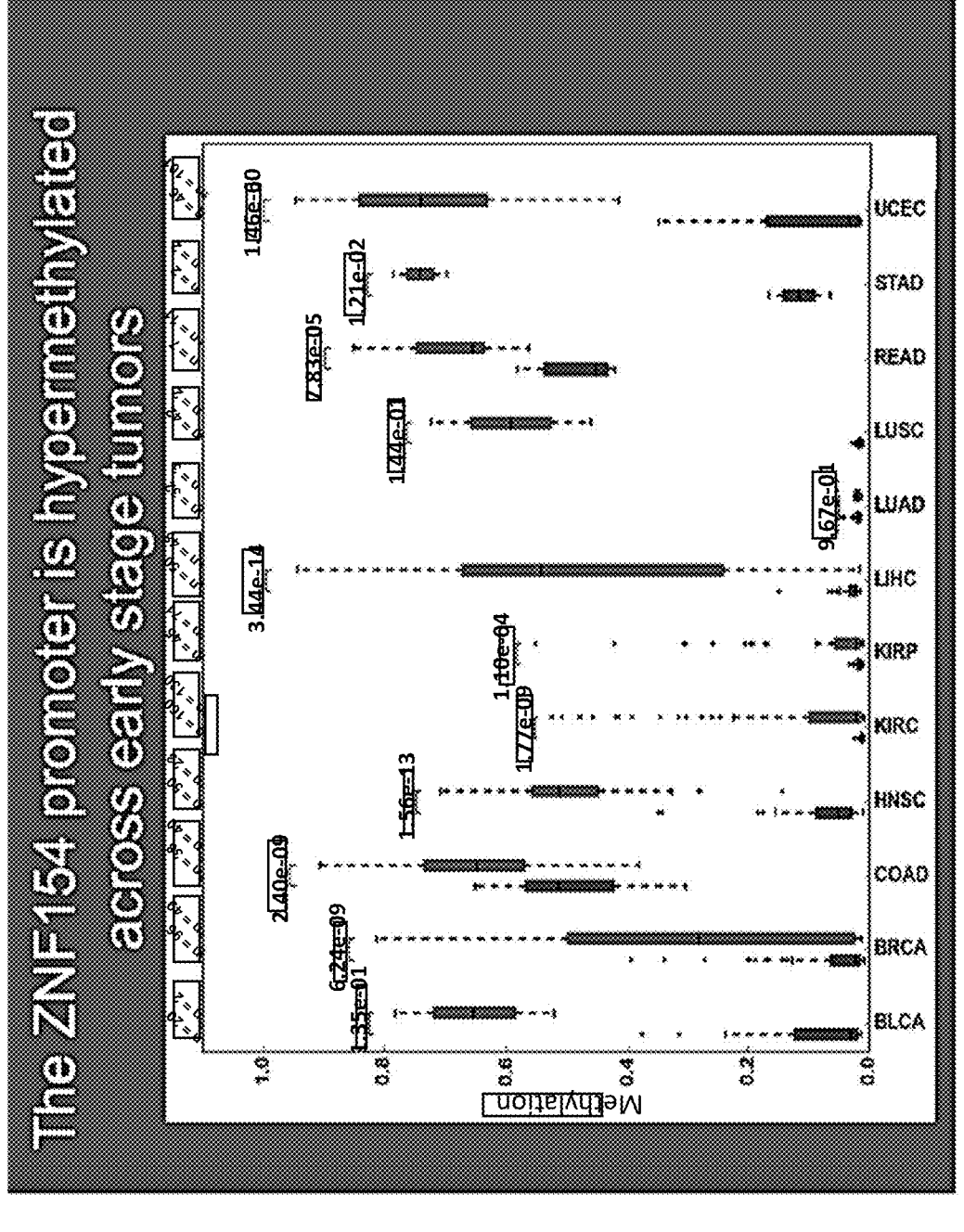
FIG. 23 shows a graph showing early stage tumor samples from TGCA data (boxplots to the right of each tumor type label) (Illumina methylation array data) showing an elevated signal compared to normal (boxplots to the left of each tumor type).

Additionally, early stage tumor samples from TCGA data (Illumina methylation array data) show an elevated signal compared to normals, similar to the elevated signal seen in all tumor stages (FIG. 23). This indicates that the methylation signature in tumors is not limited to a late stage tumor. Left column (box plot) for each condition=normal sample, right column (box plot)=tumor sample.

We claim all subject matter that comes within the scope and spirit of the claims below. Alternatives specifically addressed in these sections are merely exemplary and do not constitute all possible alternatives to the embodiments described herein.

---

The invention claimed is:

1. A method for detecting the presence of cancer in a human individual, comprising:

treating cell free genomic DNA from a plasma sample from the individual with bisulfite to produce bisulfite-treated genomic DNA; and PCR amplification of a target nucleic acid molecule comprising nucleotides 58,220,424 to 58,220,670 of chromosome 19 according to the human genome version GRCh37/hg19 from the bisulfite-treated genomic DNA to produce amplicons, sequencing the amplicons to produce a plurality of sequence reads; and detecting the methylation status of 20 CpG sites within the nucleotides 58,220,424 to 58,220,670 of chromosome 19 of the genomic DNA based on the plurality of sequence reads to identify the 20 CpG sites as hypermethylated or not;

wherein detection of the CpG sites as hypermethylated compared to a control identifies the presence of cancer in the individual; and wherein detection of the CpG sites as not hypermethylated compared to the control identifies the absence of cancer in the individual; and wherein the cancer is selected from lung cancer, stomach cancer, colon cancer, breast cancer, uterine cancer, bladder cancer, head and neck cancer, kidney cancer, liver cancer, ovarian cancer, pancreas cancer, prostate cancer, and rectum cancer.

2. The method of claim 1 wherein genomic DNA corresponding to the amplicons comprises or consists of the nucleotide sequence set forth as SEQ ID NO: 5.

3. The method of claim 1, wherein detecting the methylation status of the 20 CpG sites comprises:

calculating a ratio X:

$$X = N_{20}/(N_0 + N_{20})$$

wherein $N_0$ and $N_{20}$ are frequencies of sequence reads in the plurality where 0 or 20 of the 20 CpG sites within the nucleotides 58,220,424 to 58,220,670 of chromosome 19 of the genomic DNA are methylated, respectively; and wherein an increase in the ratio X as compared with a control is indicative of the presence of cancer in the individual; and wherein no increase in the ratio X as compared with the control is indicative of the absence of cancer in the individual.

4. The method of claim 1 wherein detecting the methylation status of the 20 CpG sites comprises:

calculating a ratio Y:

$$Y = N_{20}/(N_0 + N_1 + N_2 + N_3 + N_4 + N_5 + N_{20})$$

wherein $N_0$, $N_1$, $N_2$, $N_3$, $N_4$, $N_5$, and $N_{20}$, are frequencies of sequence reads in the plurality where 0, 1, 2, 3, 4, 5 or 20 of the 20 CpG sites within nucleotides 58,220,424 to 58,220,670 of chromosome 19 of the genomic DNA are methylated, respectively; and wherein an increase in the ratio Y as compared with a control is indicative of cancer in the individual; and wherein no increase in the ratio Y as compared with the control is indicative of the absence of cancer in the individual.

5. The method of claim 1, wherein the cytosines of the 20 CpG sites are located at nucleotides 58220424, 58220440, 58220443, 58220446, 58220460,58220466, 58220479, 58220482, 58220494, 58220500, 58220513, 58220516, 58220535,58220567, 58220572, 58220595, 58220627, 58220657, 58220662, and 58220669 of chromosome 19.

6. The method of claim 1, wherein the control is a threshold value that distinguishes between individuals with and without cancer.

*     *     *     *     *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggtttttatt ttaggtttga                                                    20

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
aaatctataa aaactacatt acctaaaata ctcta                                   35

<210> SEQ ID NO 3
<211> LENGTH: 33
<212> TYPE: DNA
<213> ORGANISM: Artificial Sequence
<220> FEATURE:
<223> OTHER INFORMATION: adaptor

<400> SEQUENCE: 3
acactctttc cctacacgac gctcttccga tct                                     33

<210> SEQ ID NO 4
<211> LENGTH: 33
<212> TYPE: DNA
<213> ORGANISM: Artificial Sequence
<220> FEATURE:
<223> OTHER INFORMATION: adaptor

<400> SEQUENCE: 4
gtgactggag ttcagacgtg tgctcttccg atc                                     33
```

-continued

```
<210> SEQ ID NO 5
<211> LENGTH: 302
<212> TYPE: DNA
<213> ORGANISM: Homo sapiens

<400> SEQUENCE: 5
ggtccctatc ccaggcctga cgtgggtccc ccagggcggc gtcgccaagg cttagacgct          60
ttcgtgcagg agggacgacg actcccctca cgccttcgtg gccccaactc ggcgctctgc         120
tatctctgat ccggtgaaca cacctcagag aagctaaaat ggccgccacg aagaggcccc        180
cccaaaagtc ccgtcctttc tttttgtgac tctcaaggaa agtcggtttt ctgagctctt        240
actggcttag tagcgtggcg ttcaacgcag agcattctag gtaatgtagt tttcatagat        300
cc                                                                         302

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
actacattac ctaaaatact                                                       20
```